(12) United States Patent
Branstetter et al.

(10) Patent No.: US 8,288,397 B2
(45) Date of Patent: Oct. 16, 2012

(54) IMIDAZOLO-, OXAZOLO-, AND THIAZOLOPYRIMIDINE MODULATORS OF TRPV1

(75) Inventors: Bryan James Branstetter, Carlsbad, CA (US); J. Guy Breitenbucher, Escondido, CA (US); Alec D. Lebsack, San Diego, CA (US); Jing Liu, San Diego, CA (US); Jason C Rech, San Diego, CA (US); Wei Xiao, San Diego, CA (US)

(73) Assignee: Janssen Pharmaceutica NV, Beerse (BE)

( * ) Notice: Subject to any disclaimer, the term of this patent is extended or adjusted under 35 U.S.C. 154(b) by 804 days.

(21) Appl. No.: 12/316,848

(22) Filed: Dec. 16, 2008

(65) Prior Publication Data
US 2009/0156599 A1 Jun. 18, 2009

Related U.S. Application Data

(60) Provisional application No. 61/014,158, filed on Dec. 17, 2007.

(51) Int. Cl.
| | |
|---|---|
| C07D 487/04 | (2006.01) |
| C07D 473/34 | (2006.01) |
| C07D 513/04 | (2006.01) |
| C07D 295/04 | (2006.01) |
| A61K 31/519 | (2006.01) |
| A61K 31/429 | (2006.01) |
| A61K 31/5377 | (2006.01) |
| A61K 31/496 | (2006.01) |
| A61K 31/5355 | (2006.01) |
| C07D 473/18 | (2006.01) |
| C07D 473/16 | (2006.01) |
| C07D 473/24 | (2006.01) |
| C07D 498/04 | (2006.01) |
| A61K 31/52 | (2006.01) |
| A61K 31/424 | (2006.01) |

(52) U.S. Cl. ............ 514/260.1; 544/255; 544/277; 544/276; 514/263.4; 514/263.2; 514/263.22; 514/263.37

(58) Field of Classification Search .......... 544/255; 514/260.1
See application file for complete search history.

(56) References Cited

U.S. PATENT DOCUMENTS

| | | | |
|---|---|---|---|
| 7,105,666 B2 | 9/2006 | Hammarstrom et al. | |
| 2002/0094974 A1 | 7/2002 | Castelhano et al. | |
| 2003/0139427 A1 | 7/2003 | Castelhano et al. | |
| 2003/0191086 A1 | 10/2003 | Hanus et al. | |
| 2004/0157845 A1 | 8/2004 | Doherty et al. | |
| 2005/0049263 A1 | 3/2005 | Kasibhatla et al. | |
| 2006/0223868 A1 | 10/2006 | Besidski et al. | |
| 2007/0142386 A1 | 6/2007 | Nordvall et al. | |
| 2007/0185139 A1 | 8/2007 | Binnun et al. | |
| 2007/0225275 A1 | 9/2007 | Allison et al. | |
| 2007/0259936 A1 | 11/2007 | Player et al. | |
| 2008/0004253 A1 | 1/2008 | Branstetter et al. | |

FOREIGN PATENT DOCUMENTS

| | | |
|---|---|---|
| EP | 1 731 523 A1 | 12/2006 |
| JP | 2001 97979 | 4/2001 |
| WO | WO 2004 096784 A1 | 11/2004 |
| WO | WO 2005 117890 A2 | 12/2005 |
| WO | WO 2006 0630031 A1 | 3/2006 |
| WO | WO 2006 130469 A1 | 12/2006 |
| WO | WO 2007 130780 A2 | 11/2007 |

OTHER PUBLICATIONS

Banker, G.S. et al, "Modern Pharmaceutics, 3ed.", Marcel Dekker, New York, 1996, p. 596.*
Wolff, Manfred E. "Burger's Medicinal Chemistry, 5ed, Part I", John Wiley & Sons, 1995, pp. 975-977.*
International Search Report for Corresponding PCT/US08/13808 Dated Feb. 19, 2009 2 PGS.
Extended European Search Report for Corresponding EP Application No. 08862830.0 Mailed on Jul. 1, 2011.
Agopyan et al. "TRPV1 Receptors Mediate Particulate Matter-Induced Apoptosis" Am J Physiol Lung Cell Mol Physiol 2004 vol. 286 pp. L563-572.
Agopyan et al. "Vanilloid Receptor Activation by 2- and 10-μm Particles Induces Responses Leading to Apoptosis in Human Airway Epithelial Cells" Toxicol Appl Pharmacol 2003 vol. 192 pp. 21-35.
Akiba et al. "Transient Receptor Potential Vanilloid Subfamily 1 Expressed in Pancreatic Islet β Cells Modulates Insulin Secretion in Rats" Biochem Biophys Res Commun 2004 vol. 321 pp. 219-225.
Apostolidis et al. "Capsaicin Receptor TRPV1 in Urothelium of Neurogenic Human Bladders and Effect of Intravesical Resiniferatoxin" Urology 2005 vol. 65 pp. 400-405.

(Continued)

*Primary Examiner* — Susanna Moore
(74) *Attorney, Agent, or Firm* — Michael J. Atkins

(57) ABSTRACT

Certain TRPV1-modulating imidazolo-, oxazolo-, and thiazolopyrimdine compounds are described. The compounds may be used in pharmaceutical compositions and methods for treating disease states, disorders, and conditions mediated by TRPV1 activity, such as pain, arthritis, itch, cough, asthma, or inflammatory bowel disease.

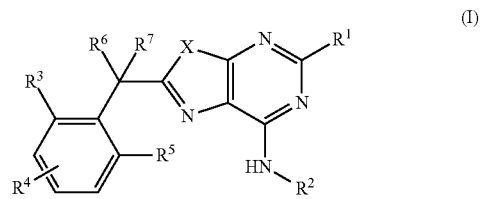

(I)

20 Claims, No Drawings

OTHER PUBLICATIONS

Asai et al. "Heat and Mechanical Hyperalgesia in Mice Model of Cancer Pain" Pain 2005 vol. 117 pp. 19-29.

Bagshawe et al. "Antibody-Directed Enzyme Prodrug Therapy: A Review" Drug Dev Res 1995 vol. 34 pgs. 220-230.

Balaban et al. "Type 1 Vanilloid Receptor Expression by Mammalian Inner Ear Ganglion Cells" Hear Res 2003 vol. 175 pp. 165-170.

Barton et al. "Attenuation of Experimental Arthritis in TRPV1R Knockout Mice" Exp Mol Pathol 2006 vol. 81 pp. 166-170.

Baxter et al Hit-To-Lead Studies: The Discovery of Potent, Orally Bioavailable Thiazolopyrimidine CXCR2 Receptor Antagonists Bioorg Med Chem Lett 2006 vol. 16 pp. 960-963.

Berge et al. "Pharmaceutical Salts". J. Pharm Sci 1977 vol. 66 pp. 1-19.

Bertolini et al."A New Rational Hypothesis for the Pharmacophore of the Active Metabolite of Leflunomide, A Potent Immunosuppressive Drug" J Med Chem 1997 vol. 40 pp. 2011-2016.

Bodo et al. "A Hot New Twist to Hair Biology Involvement of Vanilloid Receptor-1 (VR1/TRPV1) Signaling in Human Hair Growth Control" Am J Pathol 2005 vol. 166(4) pp. 985-998.

Bodor et al. "Novel Approaches to the Design of Safer Drugs: Soft Drugs and Site-Specific Chemical Delivery Systems" Adv Drug Res 1984 vol. 13 pp. 224-331.

Bolcskei et al. "Investigation of the Role of TRPV1 Receptors in Acute and Chronic Nociceptive Processes Using Gene-Deficient Mice" Pain 2005 vol. 117 pp. 368-376.

Bundgaard et al Design of Prodrugs H Bundgaard Ed. Elsevier 1985.

Calkins et al Abstract "TRPVI Channels Modulate Pressure-Induced Death of Retinal Ganglion Cells" From ARVO 2006 Annual Meeting Program #1557 Poster #B93.

Caterina et al "Vanilloid Receptors Take a TRP Beyond the Sensory Afferent" Pain 2003 vol. 105 pp. 5-9.

Caterina et al "The Vanilloid Receptor: A Molecular Gateway to the Pain Pathway" Annu Rev Neurosci 2001 vol. 24 pp. 487-517.

Chan et al "Sensory Fibres Expressing Capsaicin Receptor TRPV1 in Patients With Rectal Hypersensitivity and Faecal Urgency" Lancet 2003 vol. 361 pp. 385-391.

Dinis et al "An Andamide-Evoked Activation of Vanilloid Receptor 1 Contributes to the Development of Bladder Hyperreflexia and Nociceptive Transmission to Spinal Dorsal Horn Neurons in Cystitis" J Neurosci 2004 vol. 24 pp. 11253-11253.

Fleisher et al "Improved Review Oral Drug Delivery: Solubility Limitations of Prodrugs Overcome by the Use" Adv Drug Delivery Rev 1996 vol. 19 pp. 115-130.

Geppetti et al "Activation and Sensitisation of the Vanilloid Receptor: Role in Gastrointestinal Inflammation and Function" Br J Pharmacol 2004 vol. 141 pp. 1313-1320.

Ghilardi et al "Selective Blockade of the Capsaicin Receptor TRPV1 Attenuates Bone Cancer Pain" J Neurosci 2005 vol. 25(12) pp. 3126-3131.

Goadsby Peter J. "Post-Triptan Era for Thetreatment of Acute Migraine" Curr Pain Headache Reports 2004 vol. 8 pp. 393-398.

Greiff et al "Effects of Topical Capsaicin in Seasonal Allergic Rhinitis" Thorax 1995 vol. 50 pp. 225-229.

Honore et al :"A-425619 [1-Isoquinolin-5-YL-3-(4-Trifluoromethyl-Benzyl)- Urea], A Novel Transient Receptor Potential Type V1 Receptor Antagonist, Relieves Pathophysiological Pain Associated With Inflammation and Tissue Injury in Rats" J Pharmacol Exp Ther 2005 vol. 314 pp. 410-421.

Iida et al "Attenuated Fever Response in Mice Lacking TRPVI" Neurosci Lett 2005 vol. 378 pp. 28-33.

Jancso-Gabor et al "Irreversible Impairment of Thermoregulation Induced by Capsaicin and Similar Pungent Substances in Rats and Guinea-Pigs " J Physiol 1970 vol. 206 pp. 495-507.

Kim et al "Histamine-Induced $CA^{2}+$ Influx Via the $PLA_2$/Lipoxygenase/TRPV1 Pathway in Rat Sensory Neurons" Neurosci Lett 2004 vol. 361 pp. 159-162.

Kimball et al "Vanilloid Receptor 1 Antagonists Attenuate Disease Severity in Dextran Sulphate Sodium-Induced Colitis in Mice" Neurogastroenterol Motil 2004 vol. 16 pp. 811-818.

Kwak et al "A Capsaicin-Receptor Antagonist, Capsazepine Reduces Inflammation-Induced Hyperalgesic Responses in the Rat: Evidence for an Endogenous Capsaicin-Like Substance" Neuroscience 1998 vol. 86(2) pp. 619-626.

Lalloo et al "Capsazepine Inhibits Cough Induced by Capsaicin and Citric Acid But Not by Hypertonic Saline in Guinea Pigs" J Appl Physiol 1995 vol. 79(4) GPS 1082-1087.

Larsen et al Design and Application of Prodrugs, Drug Design and Development Krogsgaard-Larsen et al Eds Harwood Academic Publishers 1991.

Lazzeri et al "Immunohistochemical Evidence Of vanilloid Receptor 1 in Normal Human Urinary Bladder" Eur Urology 2004 vol. 46 pp. 792-798.

Liu et al "Single-Step Syntheses of 2-Amino-7-Chlorothiazolo[5,4-D]Pyrimidines: Intermediates for Bivalent Thiazolopyrimidines" J Org Chem 2005 vol. 70 pp. 10194-10197.

Makara et al "Synthesis of Bicyclic Pyrimidine Derivatives As ATP Analogues" J Org Chem 2001 vol. 66 pp. 5783-5789.

Marsch et al "Reduced Anxiety, Conditioned Fear, and Hippocampal Long-Term Potentiation in Transient Receptor Potentialvanilloid Type 1 Receptor-Deficient Mice" J Neurosci 2007 vol. 27(4) pp. 832-839.

Menendez et al "Analgesic Effects of Capsazepine and Resiniferatoxin on Bone Cancer Pain in Mice" Neurosci Lett 2006 vol. 393 pp. 70-73.

Moore et al "TNBS Ileitis Evokes Hyperexcitability and Changes in Ionic Membrane Properties of Nociceptive DRG Neurons" Am J Physiol Gastrointest Liver Physiol 2002 vol. 282 pp. G1045-G1051.

Morris et al "Characterisation of Capsaicin-Induced Mechanical Hyperalgesia As a Marker for Altered Nociceptive Processing in Patients With Rheumatoid Arthritis" Pain 1997 vol. 71 pp. 179-186.

Pomonis et al "N-(4-Tertiarybutylphenyl)-4-(3-Cholorphyridin-2-YL)Tetrahydropyrazine-1(2H)-Carbox-Amide (BCTC), A Novel, Orally Effective Vanilloid Receptor 1 Antagonist With Analgesic Properties: II. In Vivo Characterization in Rat Models of Inflammatory and Neuropathic Pain" J Pharmacol Exp Ther 2003 vol. 306(1) pp. 387-393.

Razavi et al "TRPV1+ Sensory Neurons Control β Cell Stress and Islet Inflammation in Autoimmune Diabetes" Cell 2006 vol. 127 pp. 1123-1135.

Robinson "Discovery of the Hemifumarate and (α-L-Alanyloxy)Methyl Ether As Prodrugs of an Antirheumatic Oxindole: Prodrugs for the Enolic OH Group" J Med Chem 1996 vol. 39 pp. 10-18.

Sanchez et al "Expression of the Transient Receptor Potential Vanilloid 1 (TRPV1) in LNCAP and PC-3 Prostate Cancer Cells and in Human Prostate Tissue" Eur J Pharmacol 2005 vol. 515 pp. 20-27.

Sculptoreanu et al "Protein Kinase C Contributes to Abnormal Capsaicin Responses in DRG Neurons From Cats With Feline Interstitial Cystitis" Neurosci Lett 2005 vol. 381 pp. 42-46.

Shan et al "Prodrug Strategies Based on Intramolecular Cyclization Reactions" J Pharm Sci 1997 vol. 86(7) pp. 765-767.

Stahl et al Handbook of Pharmaceutical Salts, Properties, Selection and Use Stahl and Wermuth Eds Wiley VCH and VHCA Zurich 2002.

Stucky et al "Bradykinin Increases the Proportion of Neonatal Rat Dorsal Root Ganglion Neurons That Respond to Capsaicin and Protons" Neuroscience 1998 vol. 84(4) pp. 1257-1265.

Swanson et al "Identification and Biological Evaluation of 4-(3-Trifluoromethylpyridin-2-YL)Piperazine-1-Carboxylic Acid (5-Trifluoromethylpyridin-2-YL)Amide, A High Affinity TRPV1 (VR1) Vanilloid Receptor Antagonist" J Med Chem 2005 vol. 48 pp. 1857-1872.

Szabo et al "Role of Transient Receptor Potential Vanilloid 1 Receptors in Adjuvant-Induced Chronic Arthritis: in Vivo Study Using Gene-Deficient Mice" J Pharmacol Exp Ther 2005 vol. 314 pp. 111-119.

Tominaga et al "Thermosensation and Pain" J Neurobiol 2004 vol. 61 pp. 3-12.

Voets et al "The Principle of Temperature-Dependent Gating in Cold- And Heat-Sensitive TRP Channels" Nature 2004 vol. 430 pp. 748-754.

Walker et al "The VR1 Antagonist Capsazepine Reverses Mechanical Hyperalgesia in Models of Inflammatory and Neuropathic Pain" J Pharmacol Exp Ther 2003 vol. 304 pp. 56-62.

Xi et al "Synthesis and Evaluation of Thiazole Carboxamides As Vanilloid Receptor 1 (TRPV1) Antagonists" Bioorg Med Chem Lett 2005 vol. 15 pp. 5211-5217.

Yiangou et al "Vanilloid Receptor 1 Immunoreactivity in Inflamed Human Bowel" Lancet et al 2001 vol. 357 pp. 1338-1339.

Zheng et al "Vanilloid Receptors in Hearing: Altered Cochlear Sensitivity by Vanilloids and Expression of TRPV1 in the Organ of Corti" J Neurophys 2003 vol. 90 pp. 444-455.

* cited by examiner

IMIDAZOLO-, OXAZOLO-, AND THIAZOLOPYRIMIDINE MODULATORS OF TRPV1

This application claims the benefit of U.S. provisional patent application Ser. No. 61/014,158, filed Dec. 17, 2007, which is hereby incorporated by reference.

FIELD OF THE INVENTION

The present invention relates to certain imidazolo-, oxazolo-, and thiazolopyrimdine compounds, methods of preparing them, pharmaceutical compositions containing them, and methods of using them for the treatment of disease states, disorders, and conditions mediated by TRPV1 activity.

BACKGROUND OF THE INVENTION

Transient receptor potential (TRP) channel proteins constitute a large and diverse family of proteins that are expressed in many tissues and cell types. One TRP channel protein of particular interest is the vanilloid receptor 1 (TRPV1 or VR1), a non-selective $Ca^{+2}$ channel that is the molecular target of vanilloid compounds (e.g., capsaicin and resiniferatoxin). Such vanilloid compounds are known to selectively depolarize nociceptors, specialized primary afferent neurons involved in the signaling pathway that leads to the sensation of pain. TRPV1 is activated by a diverse range of stimuli, including vanilloids, membrane depolarization, heat, stretch, low pH, inflammatory mediators (e.g., lipoxygenase metabolites), and endocannabinoid compounds. Because heightened activity of nociceptors contributes to unwanted pain, inflammatory conditions, thermoregulation, and control of smooth muscle tone and reflexes in mammals, modulation of signaling in this pathway is important in treatment and prophylaxis of various clinical syndromes (Caterina, M. J., *Pain* 2003, 105(1-2), 5-9; Caterina, M. J. et. al., *Annu. Rev. Neurosci.* 2001, 24, 487-517; Tominaga, M. et. al., *J. Neurobiol.* 2004, 61, 3-12; Voets, T. et. al., *Nature* 2004, 430, 748-754).

Because of TRPV1's connection with the sensory nervous system, TRPV1 agonists and antagonists may be therapeutically useful in the treatment or prophylaxis of disease states, disorders, and conditions mediated by TRPV1 activity, such as: i) pain (e.g., acute, chronic, inflammatory, or neuropathic pain); ii) itch (Kim et al., *Neurosci. Lett.* 2004, 361, 159) and various inflammatory disorders (Stucky, C. L. et. al., *Neuroscience* 1998, 84, 1257; Moore, B. A. et. al., *Am. J. Physiol. Gastrointest. Liver Physiol.* 2002, 282, G1045; Kwak, J. Y. et. al., *Neuroscience* 1998, 86, 619; Morris, V. H. et. al., *Pain* 1997, 71, 179; Greiff, L. et. al., *Thorax* 1995, 50, 225); iii) inner ear disorders (Balaban, C. D. et al., *Hear. Res.* 2003, 175, 165-70; Zheng, J. et al., *J. Neurophys.* 2003, 90, 444-55); iv) fever and other disorders or symptoms affected by thermoregulation (Jancso-Gabor et al., *J. Physiol.* 1970, 206, 495; Swanson et al., *J. Med. Chem.* 48, 1857; Iida et al., *Neurosci. Lett.* 2005, 378, 28); v) tracheobronchial and diaphragmatic dysfunction; and vi) gastrointestinal and urinary tract disorders (Lazzeri, M. et al., *Eur. Urology* 200, 792-798; Apostolidis, A. et. al., *Urology* 2005, 65, 400-405). Additionally, TRPV1 modulators may be therapeutically useful in the treatment or prophylaxis of anxiety (Marsch, R. et al., *J. Neurosci.* 2007, 27(4), 832-839); eye-related disorders (such as glaucoma, vision loss, and increased intraocular pressure) (Calkins, D. J. et al., Abstract from *ARVO 2006 Annual Meeting*, Program #1557, Poster #B93); baldness (e.g., by stimulating hair growth) (Bodo, E. et al., *Am. J. Pathol.* 2005, 166(4), 985-998); diabetes (including insulin-resistant diabetes or diabetic conditions mediated by insulin sensitivity or secretion) (Razavi, R. et al., *Cell* 2006, 127(6), 1097-1099; Akiba, Y. et al., *Biochem. Biophy. Res. Commun.* 2004, 321 (1), 219-225).

Acidosis is a well-established feature of cerebral ischaemia. Tissue pH may fall to 6 or lower, sufficient to activate TRPV1 channels expressed in the CNS. TRPV1 antagonists therefore may be useful in the treatment of disorders associated with reduced blood flow to the CNS or CNS hypoxia, such as head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

Certain thiazole carboxamides have been described as vanilloid receptor modulators (Xi et al., Bioorg. Med. Chem. Lett. 2005, 15, 5211-5217; U.S. Pat. Appl. Publ. 2004/157845). Certain thiazolopyrimidines have been described as CCR2b receptor antagonists (PCT Intl. Pat. Appl. Publ. WO 2005/117890), chemokine receptor antagonists (U.S. Pat. Appl. Publ. 2007/0142386; Baxter et al. Bioorg. Med. Chem. Lett. 2006, 26, 960-963), and inhibitors of ATP-protein kinase interactions (U.S. Pat. Appl. Publ. 2007/0185139). Certain thiazolopyrimidine compounds were described as TRPV1 modulators in U.S. patent application Ser. No. 11/824,202. Certain thiazolopyrimidine derivatives are disclosed as growth factor receptor tyrosine kinase inhibitors in Eur. Pat. Appl. EP 1731523 (Dec. 13, 2006). Condensed heterocyclic compounds are shown as macrophage migration inhibitory factor inhibitors in JP 2001097979. Certain fused pyrimidines are described as modulators of metabotropic receptors—subtype 2 in PCT Intl. Pat. Appl. Publ. WO 2006/030031. Bicyclic pyrimidinyl derivatives are disclosed as adenosine receptor binders in U.S. Pat. Appl. Publ. US 2003/139427 and U.S. Pat. Appl. Publ. US 2002/094974. Purine derivatives are described as nerve growth promoters in PCT Intl. Pat. Appl. Publ. WO 2006/130469. Various purine analogs are disclosed as heat shock protein 90 inhibitors in U.S. Pat. Appl. Publ. 2005/0049263. Purine analogs are also described as inhibitors of cyclin dependent kinases in U.S. Pat. Appl. Publ. 2003/191086.

There remains a desire for potent TRPV1 modulators with suitable pharmaceutical properties.

SUMMARY OF THE INVENTION

Certain imidazolo-, oxazolo-, and thiazolopyrimidine derivatives have now been found to have TRPV1-modulating activity. In particular, the invention is directed to the general and preferred embodiments defined, respectively, by the independent and dependent claims appended hereto, which are incorporated by reference herein.

Thus, in one general aspect, the invention relates to compounds of Formula (I):

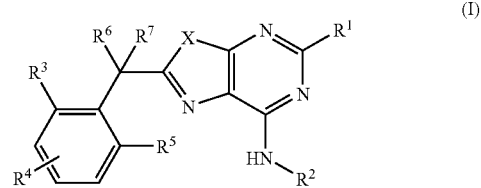

wherein:
$R^1$ is —H; —NR$^a$R$^b$; a —C$_{1-6}$alkyl, —OC$_{1-6}$alkyl, —S—C$_{1-6}$ alkyl, or —SO$_2$ —C$_{1-6}$alkyl group unsubstituted or substituted with an —OH, —OC$_{1-4}$alkyl, or —NR$^c$R$^d$ substituent;
  where R$^a$ and R$^b$ are each independently —H; —C$_{1-6}$alkyl; a —C$_{2-4}$alkyl group substituted with a —OH, —OC$_{1-4}$ alkyl, or —NR$^e$R$^f$ substituent; or a saturated monocyclic cycloalkyl, —C$_1$alkyl-(saturated monocyclic cycloalkyl), —C$_1$alkyl-(carbon-linked, saturated monocyclic heterocycloalkyl), benzyl, or —C$_1$alkyl-(monocyclic heteroaryl) group, each unsubstituted or substituted with a —C$_{1-6}$alkyl, —OH, —OC$_{1-4}$alkyl, —NR$^p$R$^q$, or fluoro substituent;
  or, R$^a$ and R$^b$ taken together with the nitrogen of attachment in —NR$^a$R$^b$ form a saturated monocyclic heterocycloalkyl group unsubstituted or substituted with one, two, or three moieties independently selected from the group consisting of —C$_{1-6}$alkyl, —C$_{1-2}$alkyl-OH, —C$_{1-2}$ alkyl-OC$_{1-2}$alkyl, —OH, —OC$_{1-4}$alkyl, —NR$^p$R$^q$, fluoro, —CO$_2$H, and monocyclic cycloalkyl substituents;
    where R$^c$ and R$^d$ are each independently —H or —C$_{1-6}$ alkyl;
      or R$^c$ and R$^d$ taken together with the nitrogen of attachment in —NR$^c$R$^d$ form a saturated monocyclic heterocycloalkyl group unsubstituted or substituted with methyl;
    R$^e$ and R$^f$ are each independently —H or —C$_{1-6}$alkyl;
      or R$^e$ and R$^f$ taken together with their nitrogen of attachment in —NR$^e$R$^f$ form a saturated monocyclic heterocycloalkyl group unsubstituted or substituted with methyl; and
    R$^p$ and R$^q$ are each independently —H or —C$_{1-6}$alkyl;
      or R$^p$ and R$^q$ taken together with the nitrogen of attachment in —NR$^p$R$^q$ form a saturated monocyclic heterocycloalkyl group unsubstituted or substituted with methyl;
$R^2$ is:
  1) a phenyl group unsubstituted or substituted with one, two, or three R$^g$ substituents;
    where each R$^g$ substituent is —C$_{1-6}$alkyl, —OH, —OC$_{1-6}$ alkyl, —CN, —NO$_2$, —N(R$^h$)R$^i$, —C(O)N(R$^h$)R$^i$, —C(O)C$_{1-6}$alkyl, —S(O)$_{0-2}$—C$_{1-6}$alkyl, —SO$_2$CF$_3$, —SO$_2$N(R$^h$)R$^i$, —SCF$_3$, halo, —CF$_3$, —OCF$_3$, —CO$_2$H, —CO$_2$C$_{1-6}$alkyl, —C(R$^j$)$_2$—CN, —C(R$^j$)$_2$—CO$_2$C$_{1-4}$alkyl, —C(R$^j$)$_2$—CO$_2$H, —C(R$^j$)$_2$—CON(R$^h$)R$^i$, —C(R$^j$)$_2$—CH$_2$N(R$^h$)R$^i$, or —C(R$^j$)$_2$—OH;
    or two adjacent R$^g$ substituents taken together form —OC$_{1-2}$alkylO—, —C$_{2-6}$alkylO—, or —C$_{2-6}$alkylN(R$^h$)—;
    where R$^h$ and R$^i$ are each independently —H or —C$_{1-6}$ alkyl;
      or R$^h$ and R$^i$ taken together with their nitrogen of attachment in —NR$^h$R$^i$ form a saturated monocyclic heterocycloalkyl group unsubstituted or substituted with methyl;
    where each R$^j$ is independently —H, —C$_{1-6}$alkyl, or —CF$_3$;
      or both R$^j$ substituents taken together with the carbon to which they are attached form a monocyclic cycloalkyl ring; or
  2) a thiadiazolyl or six-membered monocyclic heteroaryl ring, each substituted with —CF$_3$ or tert-butyl;
$R^3$ is —H, —CH$_3$, —CF$_3$, halo, —CN, —COC$_{1-6}$alkyl, —CO$_2$H, —CO$_2$C$_{1-6}$ alkyl, —C(O)N(R$^k$)R$^l$, —CH$_2$N(R$^k$)R$^l$, —S(O)$_{0-2}$—C$_{1-6}$alkyl, —S—Si(C$_{1-6}$alkyl)$_3$, —SO$_2$CF$_3$, or —SO$_2$N(R$^k$)R$^l$; or a phenyl or 6-membered heteroaryl ring, each unsubstituted or substituted with —OH, —CH$_2$N(R$^k$)R$^l$, —C(O)N(R$^k$)R$^l$, —SO$_2$N(R$^k$)R$^l$, or —CO$_2$H;
  where R$^k$ and R$^l$ are each independently —H or —C$_{1-6}$ alkyl; or R$^k$ and R$^l$ taken together with their nitrogen of attachment in —NR$^k$R$^l$ form a saturated monocyclic heterocycloalkyl group unsubstituted or substituted with methyl;
$R^4$ is —H, —CF$_3$, halo, —CN, —CO$_2$H, —CO$_2$C$_{1-6}$alkyl, —C(O)N(R$^n$)R$^o$, —C$_{1-4}$alkyl-OH, —C$_{1-4}$alkyl-N(R$^n$)R$^o$, —S(O)$_{0-2}$—C$_{1-6}$alkyl, —SO$_2$CF$_3$, or —SO$_2$N(R$^n$)R$^o$;
  where R$^n$ and R$^o$ are each independently —H or —C$_{1-6}$ alkyl;
X is S, O, or NH;
$R^5$ is —H, —CH$_3$, halo, or —CF$_3$; and
$R^6$ and $R^7$ are each independently —H or methyl; or R$^6$ and R$^7$ taken together with the carbon to which they are attached form a monocyclic cycloalkyl ring.

The invention also relates to pharmaceutically acceptable salts, pharmaceutically acceptable prodrugs, and pharmaceutically active metabolites of compounds of Formula (I). In certain preferred embodiments, the compound of Formula (I) is a compound selected from those species described or exemplified in the detailed description below.

In a further general aspect, the invention relates to pharmaceutical compositions each comprising: (a) an effective amount of an agent selected from compounds of Formula (I) and pharmaceutically acceptable salts, pharmaceutically acceptable prodrugs, and pharmaceutically active metabolites thereof; and (b) a pharmaceutically acceptable excipient.

In another general aspect, the invention is directed to a method of treating a subject suffering from or diagnosed with a disease, disorder, or medical condition (collectively, "indications") mediated by TRPV1 activity, comprising administering to the subject in need of such treatment an effective amount of a compound of Formula (I), or a pharmaceutically acceptable salt, pharmaceutically acceptable prodrug, or pharmaceutically active metabolite of such compound. In certain preferred embodiments of the inventive method, the disease, disorder, or medical condition is selected from: pain (acute, chronic, inflammatory, or neuropathic pain); itch or various inflammatory disorders; inner ear disorders; fever and other conditions or disorders of thermoregulation; tracheobronchial and diaphragmatic dysfunction; gastrointestinal and urinary tract disorders; and disorders associated with reduced blood flow to the CNS or CNS hypoxia.

Preferred embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following detailed description, including the following glossary of terms and the concluding examples. For the sake of brevity, the disclosures of the publications, including patents, cited in this specification are herein incorporated by reference.

The terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by a / symbol), ethyl (Et), n-propyl (Pr), isopropyl (iPr), butyl (nBu), isobutyl (iBu), sec-butyl (sBu), tert-butyl (tBu), pentyl, isopentyl, tert-pentyl, hexyl, isohexyl, and so on.

The term "cycloalkyl" refers to a saturated or partially saturated, monocyclic, fused polycyclic, or spiro polycyclic carbocycle having from 3 to 12 ring atoms per carbocycle. Illustrative examples of cycloalkyl groups include the following entities (depicted without their bonds of attachment):

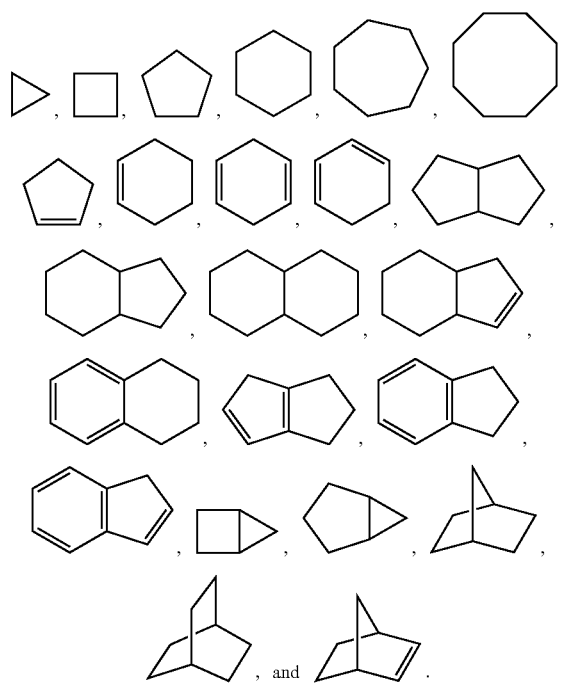

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative examples (depicted without their bonds of attachment) include:

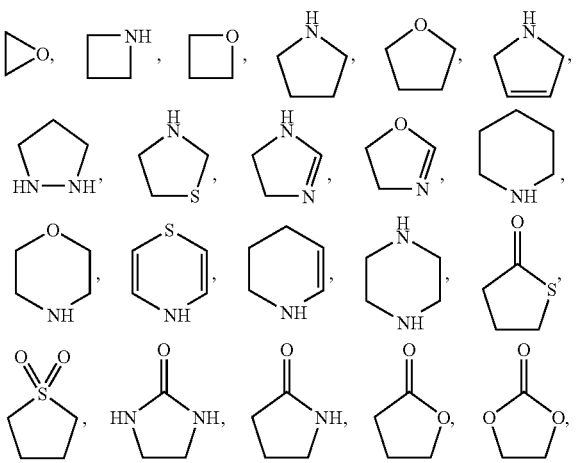

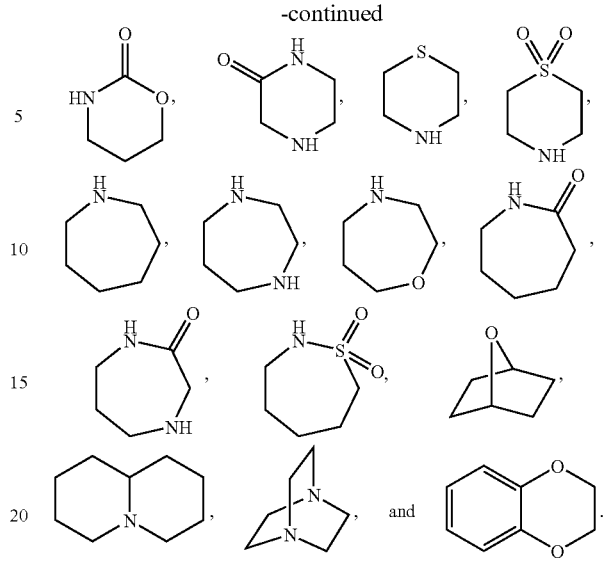

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities (depicted without their bonds of attachment):

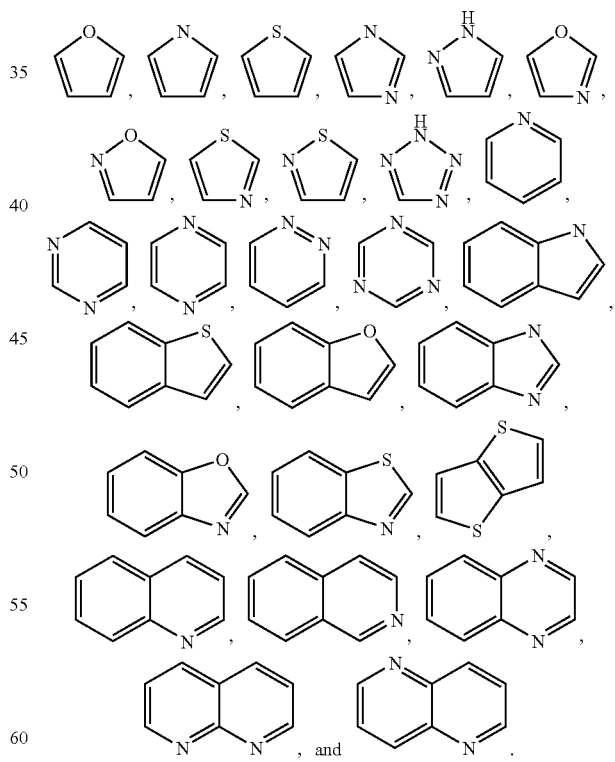

Those skilled in the art will recognize that the species of cycloalkyl, heterocycloalkyl, and heteroaryl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of any general structural formula, and mixtures thereof, are considered within the scope of the formula. Thus, any general formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any general formula given herein is intended to embrace hydrates, solvates, and polymorphs of such compounds, and mixtures thereof.

Any general formula given herein is also intended to represent unlabeled forms as well as isotopically labeled forms of the compounds. Isotopically labeled compounds have structures of the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$, respectively. Such isotopically labeled compounds are useful in metabolic studies (preferably with $^{14}C$), reaction kinetic studies (with, for example $^2H$ or $^3H$), detection or imaging techniques (such as positron emission tomography (PET) or single-photon emission computed tomography (SPECT)) including drug or substrate tissue distribution assays, or in radioactive treatment of patients. In particular, an $^{18}F$ or $^{11}C$ labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to a formula given herein, the selection of a particular moiety from a list of possible species for a specified variable is not intended to define the moiety for the variable appearing elsewhere. In other words, where a variable appears more than once in a formula, the choice of the species from a specified list is independent of the choice of the species for the same variable elsewhere in the formula unless otherwise indicated.

In certain preferred embodiments of compounds of Formula (I), $R^1$ is —H, methyl, —$OC_{1-4}$alkyl, —$SC_{1-4}$alkyl, or —$SO_2$—$C_{1-6}$alkyl. In other preferred embodiments, $R^1$ is —H, methyl, methoxy, isopropoxy, isobutoxy, methanesulfanyl, or methanesulfonyl. In further preferred embodiments, $R^1$ is —H.

In certain preferred embodiments, $R^1$ is —$NR^aR^b$. In other preferred embodiments, $R^1$ is —$NR^aR^b$ and $R^a$ and $R^b$ are each independently —H; —$C_{1-4}$alkyl; or a —$C_2$alkyl group substituted with a —OH, —$OC_{1-4}$alkyl, or —$NR^eR^f$ substituent. Preferably, $R^1$ is isopropylamino, isobutylamino, diisopropylamino, 2-hydroxy-1-methyl-ethylamino, 2-morpholin-4-yl-ethyl, 2-pyrrolidin-1-yl-ethyl, cyclopropylmethylamino, pyridin-2-ylmethyl, pyridin-3-ylmethyl, pyridin-4-ylmethyl, azetidinyl, pyrrolidinyl, 2-methylpyrrolidinyl, 2-isopropyl-pyrrolidinyl, 2-methoxymethyl-pyrrolidinyl, piperidinyl, 4-pyrrolidin-1-yl-piperidin-1-yl, piperazinyl, 4-methyl-piperazinyl, 4-isopropyl-piperazinyl, 4-isobutyl-piperazinyl, 4-cyclopentyl-piperazinyl, or morpholinyl.

Preferably, $R^a$ and $R^b$ are each independently —H; methyl, ethyl, propyl, isopropyl, butyl, isobutyl, sec-butyl, tert-butyl, pentyl, isopentyl, or hexyl; an ethyl or propyl group substituted with an —OH or —$NR^eR^f$ substituent; or a cyclopropyl, cyclobutyl, cyclopentyl, cyclohexyl, cycloheptyl, cyclopropylmethyl, cyclopentylmethyl, pyridylmethyl, pyrrolidinylmethyl, or piperidinylmethyl group, each unsubstituted or substituted with a methyl, methoxy, or fluoro substituent. In still other preferred embodiments, $R^a$ and $R^b$ are each independently —H, isopropyl, isobutyl, 1-hydroxy-2-propyl, 2-morpholin-4-ylethyl, 2-pyrrolidin-1-ylethyl, cyclopropyl, cyclobutyl, cyclopropylmethyl, pyridylmethyl, 1-pyridin-2-ylethyl, (1-ethylpyrrolidin-2-yl)methyl, pyrrolidin-3-ylmethyl, piperidin-2-ylmethyl, piperidin-3-ylmethyl, or piperidin-4-ylmethyl.

In alternative embodiments, Ra and Rb taken together with the nitrogen of attachment form an azetidinyl, pyrrolidinyl, piperidinyl, 2-oxo-piperidin-1-yl, piperazinyl, oxo-piperazinyl, morpholinyl, thiomorpholinyl, 1,1-dioxo-1-thiomorpholin-4-yl, or azepanyl group, each unsubstituted or substituted with a —C1-4-alkyl, —OH, —CH2-OC1-2alkyl, —CO2H, or monocyclic cycloalkyl substituent. In further preferred embodiments, Ra and Rb taken together with the nitrogen of attachment form an azetidinyl, pyrrolidinyl, piperidinyl, piperazinyl, or morpholinyl group, each unsubstituted or substituted with a methyl, isopropyl, isobutyl, methoxymethyl, or cyclopentyl substituent.

In preferred embodiments, $R^c$ and $R^d$ are each independently —H, methyl, or ethyl.

In preferred embodiments, $R^e$ and $R^f$ are each independently —H, methyl, or ethyl; or $R^e$ and $R^f$ taken together with their nitrogen of attachment form a pyrrolidinyl or morpholinyl group.

Preferably, $R^p$ and $R^q$ are each independently —H, methyl, or ethyl; or $R^p$ and $R^q$ taken together with the nitrogen of attachment form a pyrrolidinyl group.

Preferably, $R^2$ is a phenyl group unsubstituted or substituted with one or two $R^g$ substituents. In further preferred embodiments, $R^2$ is a phenyl group substituted with trifluoromethyl. In other embodiments, $R^2$ is a thiadiazolyl, pyridinyl, or pyrazinyl ring substituted with —$CF_3$ or tert-butyl. In further preferred embodiments, $R^2$ is 5-(trifluoromethyl)-1,3,4-thiadiazol-2-yl, 5-(tert-butyl)-1,3,4-thiadiazol-2-yl, 5-trifluoromethyl-pyrazin-2-yl, 5-trifluoromethyl-pyridin-2-yl, or 6-trifluoromethyl-pyridin-3-yl.

In certain preferred embodiments, each $R^g$ substituent is independently methyl, isopropyl, tert-butyl, —$OCH_3$, —SO$_2$CH$_3$, —SO$_2$CF$_3$, —SO$_2$NH$_2$, —SO$_2$ (morpholinyl), —SO$_2$(piperazinyl), fluoro, chloro, —CF$_3$, —OCF$_3$, —CO$_2$CH$_3$, —C(CH$_3$)$_2$—CN, —C(CH$_3$)$_2$—CO$_2$CH$_3$, —C(CH$_3$)$_2$—CONH$_2$, or —C(CH$_3$)$_2$—OH; or two adjacent R$^g$ substituents taken together form —OC$_{1-2}$alkylO—. In further preferred embodiments, each R$^g$ substituent is independently tert-butyl or —CF$_3$.

Preferably, R$^h$ and R$^i$ are each independently —H or methyl; or R$^h$ and R$^i$ taken together with their nitrogen of attachment form a morpholinyl or piperazinyl group, unsubstituted or substituted with methyl.

In some preferred embodiments, R$^j$ is —H or methyl.

In various preferred embodiments, R$^3$ is —H, chloro, iodo, methyl, —CF$_3$, —CN, or —S—Si(iPr)$_3$. In other preferred embodiments, R$^3$ is —H, chloro, or —CF$_3$. In still other preferred embodiments, R$^3$ is a phenyl or pyridyl group, each unsubstituted or substituted as described above.

In preferred embodiments, R$^k$ and R$^l$ are each independently —H or methyl. In other preferred embodiments, R$^k$ and R$^l$ are taken together with the nitrogen to which they are attached to form an unsubstituted or substituted pyrrolidinyl, piperidinyl, or morpholinyl ring.

In preferred embodiments, R$^4$ is —H, —CN, —C(O)N(R$^k$)R$^l$, —CH$_2$OH, or —CH$_2$N(R$^k$)R$^l$. In other embodiments, R$^4$ is —H or chloro.

In preferred embodiments, X is S.

In preferred embodiments, R$^5$ is —H, chloro, or —CF$_3$.

In preferred embodiments, R$^6$ and R$^7$ are both —H.

Further preferred embodiments of Formula (I) include compounds wherein combinations of two or more of the preferred embodiments for each of R$^{1-7}$, X, and R$^{a-q}$ listed above are selected. For example, preferred embodiments of Formula (I) include those where R$^1$ is —H, R$^2$ is a phenyl group substituted with trifluoromethyl, R$^3$ is —H, chloro, or —CF$_3$, R$^4$ is —H or chloro, R$^5$ is —H, chloro, or —CF$_3$, R$^6$ and R$^7$ are both —H, and X is S.

The invention includes also pharmaceutically acceptable salts of the compounds represented by Formula (I), preferably of those described above. Pharmaceutically acceptable salts of the specific compounds exemplified herein are especially preferred.

A "pharmaceutically acceptable salt" is intended to mean a salt of a free acid or base of a compound represented by Formula (I) that is pharmacologically effective and suitable for administration to the subject such that contact with the tissues of patients occurs without undue toxicity, irritation, or allergic response. See generally, Berge et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002.

A compound may possess a sufficiently acidic group, a sufficiently basic group, or both types of functional groups, and accordingly react with an inorganic or organic base, or an inorganic and organic acid, to form a pharmaceutically acceptable salt. Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, and any compatible mixture of acids such as those given as examples herein.

If the compound is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of the invention. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of the compound. Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of the compounds as amides or alkyl esters. Examples of amides include those derived from ammonia, primary C$_{1-6}$alkyl amines and secondary di(C$_{1-6}$alkyl)amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$ alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I). A "pharmaceutically active metabolite" means a pharmacologically active product of metabolism in the body of the compound or salt thereof. Prodrugs and active metabolites of a compound may be determined using routine techniques known or available in the art. See, e.g., Bertolini et al., *J. Med. Chem.* 1997, 40, 2011-2016; Shan et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "agents") of the present invention are useful as TRPV1 modulators in the methods of the invention. The agents may be used in the inventive methods for the treatment of medical conditions, diseases, or disorders, including symptoms or disease states, mediated through modulation of TRPV1, such as those described herein.

Accordingly, the invention relates to methods of using the agents to treat subjects diagnosed with or suffering from a disease, disorder, or condition mediated through TRPV1 activity, such as: i) pain (acute, chronic, inflammatory, or neuropathic pain); ii) itch or various inflammatory disorders; iii) inner ear disorders; iv) fever or other disorders of thermoregulation; v) tracheobronchial or diaphragmatic dysfunction; vi) gastrointestinal or urinary tract disorders; or vii) disorders associated with reduced blood flow to the CNS or CNS hypoxia.

In a preferred embodiment, an agent of the present invention is administered to treat pain. Certain types of pain may be considered a disease or disorder, while other types may be considered symptoms of various diseases or disorders, and pain may include various etiologies. Exemplary types of pain treatable with a TRPV1-modulating agent according to the invention include pain associated with, arising from, or caused by: osteoarthritis, rotator cuff disorders, arthritis (e.g., rheumatoid arthritis or inflammatory arthritis; see, Barton et al. *Exp. Mol. Pathol.* 2006, 81(2), 166-170), fibromyalgia, migraine and headache (e.g. cluster headache, sinus headache, or tension headache; see, Goadsby *Curr. Pain Headache Reports.* 2004, 8, 393), sinusitis, oral mucositis, toothache, dental trauma, dental extractions, dental infections, burn (Bölcskei et al., *Pain* 2005, 117(3), 368-376), sunburn, dermatitis, psoriasis, eczema, insect sting or bite, musculoskeletal disorders, bony fractures, ligamentous sprains, plantar fasciitis, costochondritis, tendonitis, bursitis, tennis elbow, pitcher's elbow, patellar tendonitis, repetitive strain injury, myofascial syndrome, muscle strain, myositis, temporomandibular joint disorder, amputation, low back pain, spinal cord injury, neck pain, whiplash, bladder spasms, GI tract disorders, cystitis, interstitial cystitis, cholecystitis, urinary tract infection, urethral colic, renal colic, pharyngitis, cold sores, stomatitis, external otitis, otitis media (Chan et al., *Lancet* 2003, 361, 385), burning mouth syndrome, mucositis, esophageal pain, esophageal spasms, abdominal disorders, gastroesophageal reflux disease, pancreatitis, enteritis, irritable bowel disorder, inflammatory bowel disease, Crohn's disease, ulcerative colitis, colon distension, abdominal constriction, diverticulosis, diverticulitis, intestinal gas, hemorrhoids, anal fissures, anorectal disorders, prostatitis, epididymitis, testicular pain, proctitis, rectal pain, labor, childbirth, endometriosis, menstrual cramps, pelvic pain, vulvodynia, vaginitis, orolabial and genital infections (e.g. herpes simplex), pleurisy, pericarditis, non-cardiac chest pain, contusions, abrasions, skin incision (Honore, P. et al., *J. Pharmacol. Exp. Ther.* 2005, 314, 410-21), postoperative pain, peripheral neuropathy, central neuropathy, diabetic neuropathy, acute herpetic neuralgia, post-herpetic neuralgia, trigeminal neuralgia, glossopharyngeal neuralgia, atypical facial pain, gradiculopathy, HIV associated neuropathy, physical nerve damage, causalgia, reflex sympathetic dystrophy, sciatica, cervical, thoracic or lumbar radiculopathy, brachial plexopathy, lumbar plexopathy, neurodegenerative disorders, occipital neuralgia, intercostal neuralgia, supraorbital neuralgia, inguinal neuralgia, meralgia paresthetica, genitofemoral neuralgia, carpal tunnel syndrome, Morton's neuroma, post-mastectomy syndrome, post-thoracotomy syndrome, post-polio syndrome, Guillain-Barré syndrome, Raynaud's syndrome, coronary artery spasm (Printzmetal's or variant angina), visceral hyperalgesia (Pomonis, J. D. et al. *J. Pharmacol. Exp. Ther.* 2003, 306, 387; Walker, K. M. et al., *J. Pharmacol. Exp. Ther.* 2003, 304(1), 56-62), thalamic pain, cancer (e.g. pain caused by cancer, including osteolytic sarcoma, by treatment of cancer by radiation or chemotherapy, or by nerve or bone lesions associated with cancer (see, Menendez, L. et al., *Neurosci. Lett.* 2005, 393 (1), 70-73; Asai, H. et al., *Pain* 2005, 117, 19-29), or bone destruction pain (see, Ghilardi, J. R. et al., *J. Neurosci.* 2005, 25; 3126-31)), infection, or metabolic disease. Additionally, the compounds may be used to treat pain indications such as visceral pain, ocular pain, thermal pain, dental pain, capsaicin-induced pain (as well as other symptomatic conditions induced by capsaicin such as cough, lachrymation, and bronchospasm).

In another preferred embodiment, inventive agents are administered to treat: itch, which may arise from various sources, such as dermatological or inflammatory disorders; or inflammatory disorders selected from the group consisting of: renal or hepatobiliary disorders, immunological disorders, medication reactions and unknown/idiopathic conditions. Inflammatory disorders treatable with an inventive agent include, for example, inflammatory bowel disease (IBD), Crohn's disease, and ulcerative colitis (Geppetti, P. et al., *Br. J. Pharmacol.* 2004, 141, 1313-20; Yiangou, Y. et al., *Lancet* 2001, 357, 1338-39; Kimball, E. S. et al., *Neurogastroenterol.*

Motil., 2004, 16, 811), osteoarthritis (Szabo, A. et al., *J. Pharmacol. Exp. Ther.* 2005, 314, 111-119), psoriasis, psoriatic arthritis, rheumatoid arthritis, myasthenia gravis, multiple sclerosis, scleroderma, glomerulonephritis, pancreatitis, inflammatory hepatitis, asthma, chronic obstructive pulmonary disease, allergic rhinitis, uveitis, and cardiovascular manifestations of inflammation including atherosclerosis, myocarditis, pericarditis, and vasculitis.

In another preferred embodiment, inner ear disorders are treated with an inventive agent. Such disorders include, for example, hyperacusis, tinnitus, vestibular hypersensitivity, and episodic vertigo.

In another preferred embodiment, tracheobronchial and diaphragmatic dysfunctions are treated with an inventive agent, including, for example, asthma and allergy-related immune responses (Agopyan, N. et al., *Am. J. Physiol. Lung Cell Mol. Physiol.* 2004, 286, L563-72; Agopyan, N. et al., *Toxicol. Appl. Pharmacol.* 2003, 192, 21-35), cough (e.g., acute or chronic cough, or cough caused by irritation from gastroesophageal reflux disease; see, Lalloo, U. G. et al., *J. Appl. Physiol.* 1995, 79(4), 1082-7), bronchospasm, chronic obstructive pulmonary disease, chronic bronchitis, emphysema, and hiccups (hiccoughs, singultus).

In yet another preferred embodiment, gastrointestinal and urinary tract disorders are treated with an inventive agent, such as, bladder overactivity, inflammatory hyperalgesia, visceral hyperreflexia of the urinary bladder, hemorrhagic cystitis (Dinis, P. et al., *J. Neurosci.* 2004, 24, 11253-11263), interstitial cystitis (Sculptoreanu, A. et al., *Neurosci. Lett.* 2005, 381, 42-46), inflammatory prostate disease, prostatitis (Sanchez, M. et al., *Eur. J. Pharmacol.* 2005, 515, 20-27), nausea, vomiting, intestinal cramping, intestinal bloating, bladder spasms, urinary urgency, defecation urgency and urge incontinence.

In another preferred embodiment, disorders associated with reduced blood flow to the CNS or CNS hypoxia are treated with an inventive agent. Such disorders include, for example, head trauma, spinal injury, thromboembolic or hemorrhagic stroke, transient ischaemic attacks, cerebral vasospasm, hypoglycaemia, cardiac arrest, status epilepticus, perinatal asphyxia, Alzheimer's disease, and Huntington's Disease.

In other embodiments, inventive agents are administered to treat other diseases, disorders, or conditions mediated through TRPV1 activity, such as: anxiety; learning or memory disorders; eye-related disorders (such as glaucoma, vision loss, increased intraocular pressure, and conjunctivitis); baldness (e.g., by stimulating hair growth); diabetes (including insulin-resistant diabetes or diabetic conditions mediated by insulin sensitivity or secretion); obesity (e.g., through appetite suppression); dyspepsia; biliary colic; renal colic; painful bladder syndrome; inflamed esophagus; upper airway disease; urinary incontinence; acute cystitis; and envenomations (such as marine, snake, or insect stings or bites, including jellyfish, spider, or stingray envenomations).

In especially preferred embodiments of the therapeutic methods of the invention, effective amounts of the TRPV1 modulators of the present invention are administered to treat pain, arthritis, itch, cough, asthma, or inflammatory bowel disease.

The term "treat" or "treating" as used herein is intended to refer to administration of an inventive agent or composition of matter of the invention to a subject to effect a therapeutic or prophylactic benefit through modulation of TRPV1 activity. Treating includes reversing, ameliorating, alleviating, inhibiting the progress of, lessening the severity of, or preventing a disease, disorder, or condition (or one or more symptoms of such disease, disorder or condition) mediated through modulation of TRPV1 activity. The term "subject" refers to a mammalian patient in need of such treatment, such as a human. "Modulators" include both inhibitors and activators, where "inhibitors" refer to compounds that decrease, prevent, inactivate, desensitize or down-regulate TRPV1 expression or activity, and "activators" are compounds that increase, activate, facilitate, sensitize, or up-regulate TRPV1 expression or activity.

In treatment methods according to the invention, an effective amount of at least one agent according to the invention is administered to a subject suffering from or diagnosed as having such a disease, disorder, or condition. An "effective amount" means an amount or dose generally sufficient to bring about the desired therapeutic or prophylactic benefit in patients in need of such treatment for the designated disease, disorder, or condition. Effective amounts or doses of the agents of the present invention may be ascertained by routine methods such as modeling, dose escalation studies, or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status, and response to drugs, and the judgment of the treating physician. An exemplary dose is in the range of from about 0.001 to about 200 mg of inventive agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, or QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the pharmaceutical agents of the invention may be used in combination with additional active ingredients in the treatment methods described above. The additional active ingredients may be coadministered separately with an inventive agent or included with such an agent in a pharmaceutical composition according to the invention. In an exemplary embodiment, additional active ingredients are those that are known or discovered to be effective in the treatment of conditions, disorders, or diseases mediated by TRPV1 activity, such as another TRPV1 modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition for treating pain according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, aspirin, and alpha-2 adrenergic agonists (e.g., brimonidine, clonidine, dexmedetomidine, mivazerol, guanabenz, guanfacine, or methyldopa).

The agents of the invention are used, alone or in combination with one or more other active ingredients, to formulate pharmaceutical compositions of the invention. A pharmaceutical composition of the invention comprises: (a) an effective amount of a pharmaceutical agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an inventive agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the pharmaceutical agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension. To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the inventive agent and any other active ingredients mixed with compatible pharmaceutically acceptable excipients such as diluents, disintegrators, binders, lubricants, sweeteners, flavors, colors, and preservatives. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrators. Binders may include starch and gelatin. The lubricator, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, the inventive agent may be mixed with a solid, semi-solid, or liquid diluent. Soft gelatin capsules may be prepared by mixing the inventive agent with water, an oil such as peanut oil, sesame oil, or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspenders (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 μg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to effect transdermal delivery.

Inventive agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables in the formulas depicted in the schemes below are as defined above in reference to Formula (I).

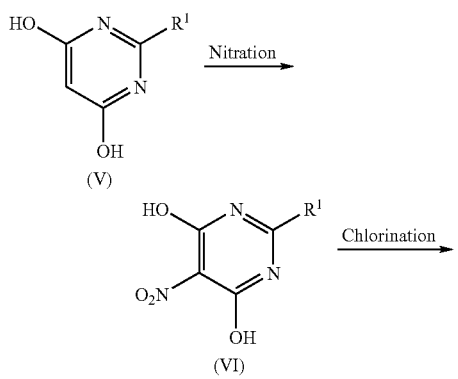

SCHEME A

-continued

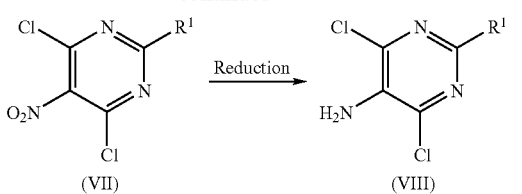

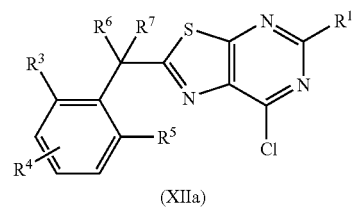

Compounds of Formula (I) may be prepared from intermediate aminopyrimidines (VIII), which are commercially available or which may be prepared as shown in Scheme A. Nitration of pyrimidine-diols (V), which are commercially available or may be prepared according to known general processes, to form nitropyrimidines (VI) may be accomplished according to general techniques known in the art. Suitable conditions include treatment with glacial acetic acid and nitric acid at a temperature from about 0° C. to about 60° C. Conversion to dichloropyrimidines (VII) may also be performed according to general techniques known in the art. Preferred conditions involve reaction of nitropyrimdines (VI) with $POCl_3$ or $PCl_3$, in a solvent such as acetonitrile, N,N-dimethylaniline, or N,N-diethylaniline, with heating at a temperature from about 50° C. to about 120° C. Reduction of the nitro group to provide an amine (VIII) may be effected using a suitable reducing agent, such as $SnCl_2$, hydrazine, or $Zn/NH_4Cl$, in a solvent such as acetone, ethanol (EtOH), water, or a mixture thereof. Exemplary conditions include treatment with $SnCl_2.H_2O$ in EtOH at about 90° C. For some embodiments, amines of formula (VIII) are commercially available.

In embodiments shown in Scheme B, dichloropyrimidines (VIII) are acylated with arylacetyl derivatives (IX), where R is a group suitable for coupling under general amide coupling conditions. Exemplary R groups include —OH, chloro, and —OC(O)$C_{1-6}$alkyl. In a preferred embodiment, compounds (IX) where R is —OH are converted to the corresponding acid chlorides by treatment with N,N-dimethylformamide (DMF) and thionyl chloride, and then reacted with pyrimidines (VIII). Resulting amides (X) are condensed with thiourea in the presence of formic acid or HCl, in a solvent such as EtOH, isopropanol, DMA (N,N-dimethylacetamide), or a mixture thereof, at a temperature from about 50° C. to about 120° C., to give hydroxythiazolopyrimidines (XI). The hydroxypyrimidines are returned to the corresponding chloro-pyrimidines (XIIa), using the chlorination conditions described in Scheme A.

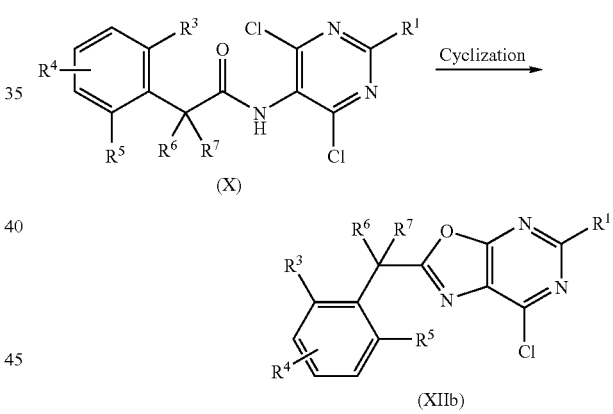

In other embodiments, as shown in Scheme C, amides (X) are cyclized under basic conditions (such as $Cs_2CO_3$, $Na_2CO_3$, or NaOH), in a solvent such as acetonitrile, at a temperature from about room temperature to about 100° C., to give oxazolopyrimidines (XIIb).

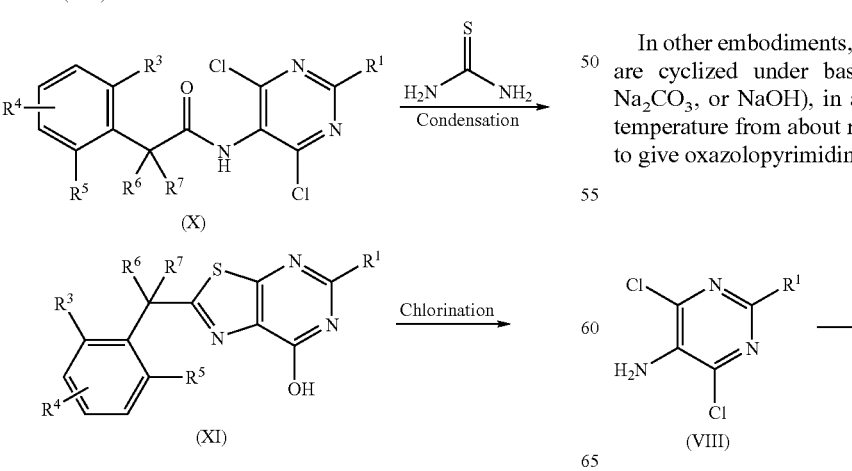

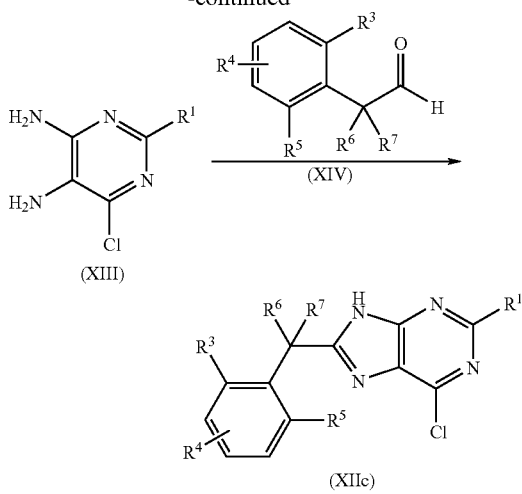

In further embodiments, intermediates of formula (XIIc) are prepared from dichloro-pyrimidines (VIII), which are commercially available or may be prepared according to known general processes. Diaminopyrimidines (XIII) are produced by displacement of a chloro substituent with ammonia or an ammonia equivalent, in a solvent such as methanol (MeOH), at a temperature from about 50° C. to about 100° C., using a microwave reactor or a sealed tube. Condensation with aldehydes (XIV), which are prepared using known general processes (e.g. by oxidation of the corresponding primary alcohols), in the presence of a dehydrating agent, yields chloro-pyrimidines (XIIc). Preferred reaction conditions include treatment with FeCl$_3$ in dioxane at a temperature from about 50° C. to about 100° C., using a microwave reactor or a sealed tube.

SCHEME E

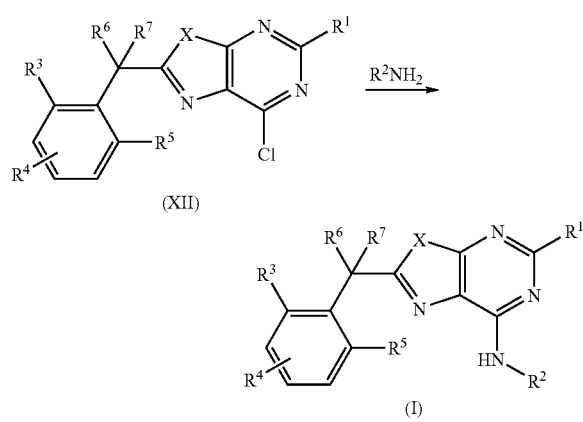

As depicted in Scheme E, chloro-pyrimidines (XII) may then be reacted with aromatic amines R$^2$NH$_2$ (where R$^2$ is phenyl, thiadiazolyl, or pyridin-3-yl), in the presence of an acid catalyst, preferably p-toluenesulfonic acid (p-TsOH), methanesulfonic acid, HCl, or trifluoroacetic acid (TFA), in a solvent such as toluene, dioxane, acetonitrile, ethanol, isopropanol, water, or a mixture thereof, at a temperature from about 70° C. to about 150° C., optionally using microwave irradiation or a sealed tube, to provide compounds of Formula (I). In preferred embodiments, chloro-pyrimidines (XII) are treated with amines R$^2$NH$_2$ and HCl in isopropanol at reflux temperature. Alternatively, reaction with amines R$^2$NH$_2$ is accomplished under palladium coupling conditions, in the presence of a palladium (0) catalyst (used directly or formed in situ), a phosphine ligand (such as PPh$_3$, (tBu)$_3$P, (cyclohexyl)$_3$P, 1,1'-bis(diphenylphosphino)ferrocene, 1,2,3,4,5-pentaphenyl-1-(di-t-butylphosphino)ferrocene, or 2-(dicyclohexylphosphino)biphenyl), and a base (such as NaOtBu, KOtBu, K$_3$PO$_4$, KOH, K$_2$CO$_3$, Cs$_2$CO$_3$, Et$_3$N, NaOH, Na$_3$PO$_4$, Na$_2$CO$_3$, or a mixture thereof), in a polar organic solvent (such as acetonitrile, toluene, DMF, ethylene glycol dimethyl ether (DME), tetrahydrofuran (THF), methanol (MeOH), EtOH, water, or a mixture thereof). Palladium coupling reactions are generally performed at temperatures from about room temperature to the reflux temperature of the solvent. In another embodiment, reaction of compounds (XII) with amines R$^2$NH$_2$ may be effected under basic conditions, for example, by treatment with a strong base such as NaH, in a polar solvent such as DMF. For compounds of Formula (I) where R$^3$ is iodide or bromide, subsequent palladium couplings provide additional embodiments, e.g. where R$^3$ is a substituted phenyl group.

SCHEME F

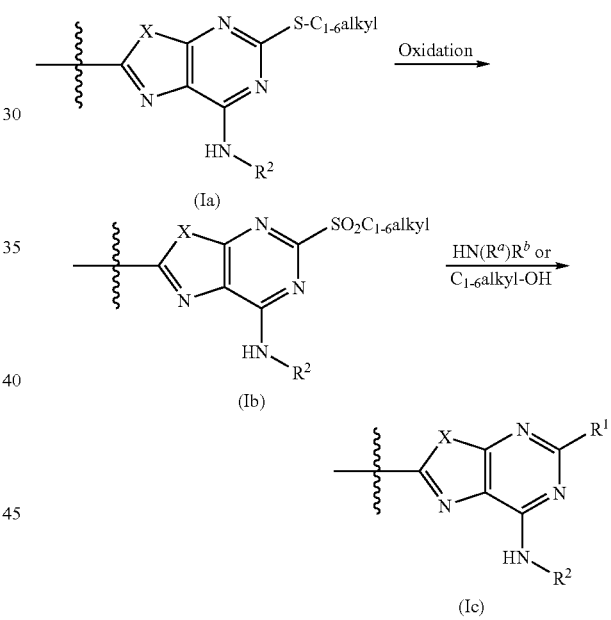

As shown in general Scheme F, embodiments of Formula (I) (shown in abbreviated form) where R$^1$ is unsubstituted or substituted —S—C$_{1-6}$alkyl (Ia) may be converted into other compounds of Formula (I), such as (Ib) and (Ic). Oxidation of thioethers (Ia) yields sulfones (Ib), and may be accomplished by reaction with a suitable oxidizing agent such as KHSO$_5$, meta-chloroperbenzoic acid (mCPBA), or dimethyldioxirane, in a solvent such as CH$_2$Cl$_2$, MeOH, THF, water, or a mixture thereof. Exemplary conditions include treatment with KHSO$_5$ (about 3 equivalents) in MeOH/THF/water at about 40° C. Displacement of the sulfone substituent to obtain a compound of formula (Ic) where R$^1$ is unsubstituted or substituted —O—C$_{1-6}$alkyl is attained by reaction with the corresponding alcohol, optionally used as the solvent, in the presence of a suitable base, such as NaH, KOtBu, or NaO—C$_{1-6}$alkyl, at a temperature between rt and the reflux temperature of the solvent, and optionally using a sealed tube. For example, to prepare compounds where $R^1$ is —OCH$_3$, preferred conditions include heating with NaOMe in MeOH at 80° C. in a sealed tube. Displacement of the sulfone substituent with amines HN($R^a$)$R^b$ yields compounds of formula (Ic) where $R^1$ is —N$R^a R^b$, and may be performed neat or in alcoholic solvents such as MeOH, EtOH, tBuOH, n-BuOH, t-amyl-OH, or a mixture thereof, or in a solvent such as toluene or benzene, at temperatures from about rt to about 150° C., and optionally using a sealed tube. In preferred embodiments, reactions are run in t-amyl-OH at a temperature of about 130° C. in a sealed tube.

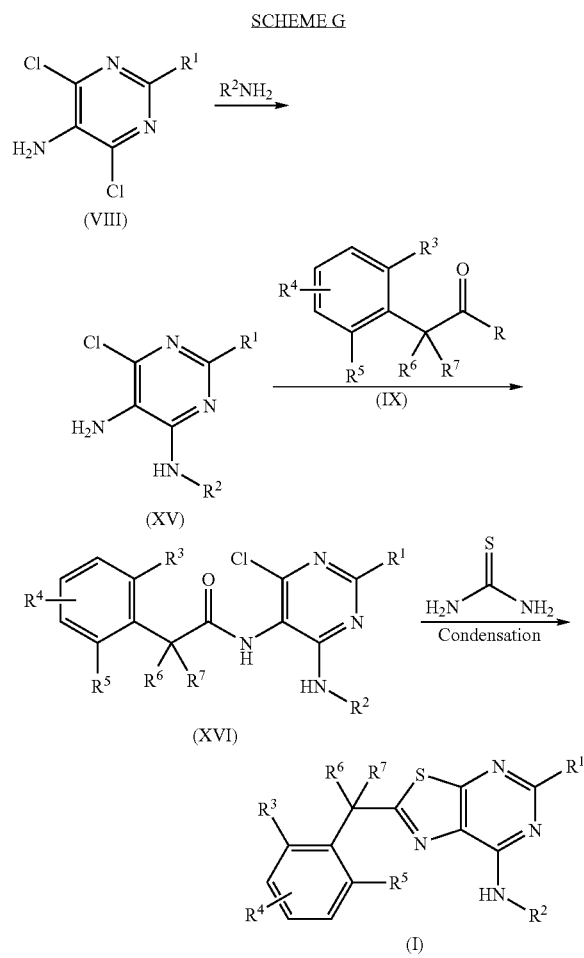

The present invention contemplates methods of making compounds of Formula (I), and pharmaceutically acceptable salts thereof, as shown in Scheme G, and chemical intermediates (XVI), which are useful in the processes of the invention. Methods of making compounds of Formula (I) comprise reacting a compound of formula (XVI) with thiourea. In preferred embodiments, such reactions are performed in the presence of an acid such as formic acid or HCl, in a solvent such as EtOH, isopropanol, DMA, or a mixture thereof, at a temperature from about 50° C. to about 120° C., to give thiazolopyrimidines of Formula (I).

Methods of the present invention further comprise reacting compounds of formula (XV) with compounds of formula (IX), where R is an "amide coupling group" (a group suitable for coupling under general amide coupling conditions). Exemplary R groups include —OH, chloro, and —OC(O)

$C_{1-6}$ alkyl. In a preferred embodiment, compounds (IX) where R is —OH are converted to the corresponding acid chlorides by treatment with N,N-dimethylformamide (DMF) and thionyl chloride, in a solvent such as CH$_2$Cl$_2$, and then reacted with pyrimidines (XV), in a solvent such as DMF or DMA. Compounds of formula (XV) are prepared by reacting dichloropyrimidines (VIII) with suitable amines $R^2$NH$_2$, in the presence of an acid catalyst, preferably p-toluenesulfonic acid (p-TsOH), methanesulfonic acid, HCl, or trifluoroacetic acid (TFA), in a solvent such as toluene, dioxane, acetonitrile, ethanol, isopropanol, water, or a mixture thereof, at a temperature from about 70° C. to about 150° C., optionally using microwave irradiation or a sealed tube.

Compounds of Formula (I) may be converted to their corresponding salts using general methods described in the art. For example, amines of Formula (I) may be treated with trifluoroacetic acid, HCl, sulfuric acid, phosphoric acid, or citric acid in a solvent such as diethyl ether (Et$_2$O), CH$_2$Cl$_2$, THF, MeOH, or isopropanol to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation techniques, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using known techniques such as chromatography or crystallization.

The following specific examples are provided to illustrate various preferred embodiments of pharmaceutical agents according to the invention.

EXAMPLES

Chemistry

In the examples below, the following experimental and analytical protocols were followed unless otherwise indicated.

Where solutions were "concentrated", they were concentrated using a rotary evaporator under reduced pressure. Unless otherwise specified, reaction solutions were stirred at room temperature (rt) under a N$_{2(g)}$ atmosphere.

Microwave reactions were carried out in either a CEM Discover® or a Biotage Initiator™ Microwave at specified temperatures.

Where solutions were dried, they were dried over MgSO$_4$ or Na$_2$SO$_4$.

Normal phase purification was typically done by normal phase flash column chromatography (FCC) with RediSep® silica gel columns using ethyl acetate (EtOAc)/hexanes as eluent unless otherwise specified.

Preparative Reversed-Phase high performance liquid chromatography (HPLC) was performed on a Shimadzu® instrument with a Phenomenex Gemini column (C18; 5 µm, 150× 21.2 mm) or Waters Xterra RP18 OBD column (5 µm, 100×30 mm), a flow rate of 30 mL/min (Gemini) or 80 mL/min (Waters), detection at λ=254 nm. The eluent was 0.05% TFA in an acetonitrile/H$_2$O gradient, ramped over 20 min.

Unless otherwise indicated, Example compounds were obtained as free bases following FCC or as trifluoroacetic acid salts following reverse phase HPLC purification.

NMR spectra were obtained on Bruker model DRX spectrometers. The format of $^1$H NMR data below is: chemical shift in ppm downfield of the tetramethylsilane reference (multiplicity, coupling constant J in Hz, integration).

Mass spectra were obtained on an Agilent series 1100 MSD using electrospray ionization (ESI) in either positive or negative modes as indicated. Calculated mass corresponds to the exact mass.

Chemical names were generated using ChemDraw Ultra 6.0.2 (CambridgeSoft Corp., Cambridge, Mass.) or ACD/Name Version 9 (Advanced Chemistry Development, Toronto, Ontario, Canada).

Intermediate 1:
2-Methylsulfanyl-5-nitro-pyrimidine-4,6-diol

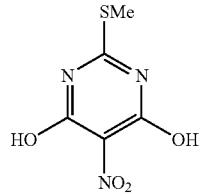

2-Methylsulfanyl-pyrimidine-4,6-diol (10 g, 63 mmol) was added portion wise to a stirring solution of glacial acetic acid (25 mL) and concentrated nitric acid (10 mL) at 50° C. After 3 h, the reaction mixture was poured onto crushed ice and the product was isolated by filtration as a yellow solid (6 g, 49%). MS (ESI, negative mode): mass calcd. for $C_5H_5N_3O_4S$, 203.0; m/z found, 202.4 [M−H].

Intermediate 2:
4,6-Dichloro-2-methylsulfanyl-pyrimidin-5-ylamine

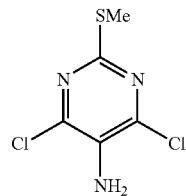

N,N-Diethylaniline (3.3 mL) was added dropwise to a stirred mixture of 2-methylsulfanyl-5-nitro-pyrimidine-4,6-diol (3.4 g, 17 mmol) and phosphoryl chloride (15 mL) at rt. After 15 min, the reaction mixture was heated to 105° C. for 1 h. The cooled reaction mixture was poured onto ice (100 g) and then extracted with Et$_2$O (3×100 mL). The combined extracts were dried, filtered, and concentrated. The residue was purified by FCC to afford a colorless solid (3.5 g, 87%) as 4,6-dichloro-2-methylsulfanyl-5-nitro-pyrimidine.

To a solution of 4,6-dichloro-2-methylsulfanyl-5-nitro-pyrimidine (1.0 g, 4.2 mmol) in EtOH (20 mL) was added SnCl$_2$.2H$_2$O (3.8 g, 17 mmol). The mixture was heated to 90° C. After 2 h, the reaction mixture was cooled and the solution was concentrated. The residue was treated with saturated (satd.) aqueous (aq.) NaHCO$_3$ until pH 8. The resulting mixture was then extracted with EtOAc (3×100 mL). The combined organic extracts were dried, filtered, and concentrated. The residue was purified by FCC to afford a colorless solid (723 mg, 87%). MS (ESI): mass calcd. for $C_5H_5Cl_2N_3S$, 208.9; m/z found, 210.3 [M+H]$^+$. $^1$H NMR ((CD$_3$)$_2$SO): 5.89 (s, 2H), 2.45 (s, 3H).

Intermediate 3: 2-(2,6-Dichloro-phenyl)-N-(4,6-dichloro-pyrimidin-5-yl)-acetamide

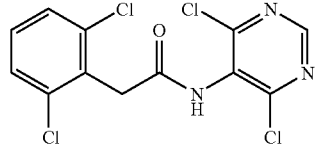

To a mixture of 2,6-dichlorophenyl acetic acid (100 g, 487 mmol) and DMF (1.5 mL) in toluene (600 mL) was added thionyl chloride (116 g, 974 mmol). The resulting mixture was stirred at rt. After 12 h, the solution was concentrated to provide 2,6-dichloro-phenylacetyl chloride as colorless oil. MS (ESI): mass calcd. for $C_8H_5Cl_3O$, 221.94; m/z found, 223.0 [M+H]$^+$. $^1$H NMR (CDCl$_3$): 7.33 (d, J=8.1 Hz, 2H), 7.29-7.24 (m, 1H), 4.56 (s, 2H). A suspension of the crude 2,6-dichloro-phenylacetyl chloride and 4,6-dichloro-pyrimidin-5-ylamine (76 g, 463 mmol) was heated neat to 130° C. After 1 h, the resulting solid was cooled, collected by filtration, and washed with cold MeOH (400 mL) to provide the title compound as a solid (135 g, 84%). MS (ESI): mass calcd. for $C_{12}H_7Cl_4N_3O$, 348.9; m/z found, 350.0 [M+H]$^+$. $^1$H NMR ((CD$_3$)$_2$SO): 10.59 (s, 1H), 8.86 (s, 1H), 7.50 (d, J=8.0 Hz, 2H), 7.37-7.33 (m, 1H), 4.13 (s, 2H).

Intermediates 4-13 were prepared using methods analogous to those described for Intermediate 3.

Intermediate 4: N-(4,6-Dichloro-2-methyl-pyrimidin-5-yl)-2-(2,6-dichloro-phenyl)-acetamide

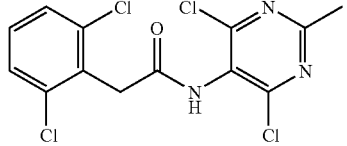

MS (ESI): mass calcd. for $C_{13}H_9Cl_4N_3O$, 362.9; m/z found, 363.9 [M+H]$^+$. $^1$H NMR ((CD$_3$)$_2$SO): 10.44 (s, 1H), 7.49 (d, J=8.0 Hz, 1H), 7.37-7.33 (m, 1H), 4.10 (s, 2H), 2.62 (s, 3H).

Intermediate 5: N-(4,6-Dichloro-2-methylsulfanyl-pyrimidin-5-yl)-2-(2,6-dichloro-phenyl)-acetamide

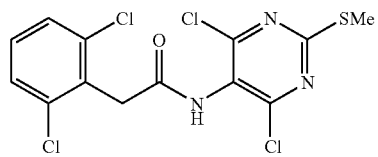

MS (ESI): mass calcd. for $C_{13}H_9Cl_4N_3OS$, 394.9; m/z found, 396.0 [M+H]$^+$. $^1$H NMR ((CD$_3$)$_2$SO): 10.39 (s, 1H), 7.49 (d, J=8.0 Hz, 2H), 7.37-7.33 (m, 1H), 4.09 (s, 2H), 2.55 (s, 3H).

Intermediate 6: N-(4,6-Dichloro-pyrimidin-5-yl)-2-o-tolyl-acetamide

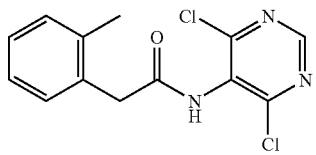

MS (ESI): mass calcd. for $C_{13}H_{11}Cl_2N_3O$, 295.0; m/z found, 296.1 [M+H]$^+$. $^1$H NMR ((CD$_3$)$_2$SO): 10.41 (s, 1H), 8.85 (s, 1H), 7.32-7.26 (m, 1H), 7.21-7.13 (m, 3H), 3.78 (s, 2H), 2.33 (s, 3H).

Intermediate 7: 2-(2-Chloro-phenyl)-N-(4,6-dichloro-pyrimidin-5-yl)-acetamide

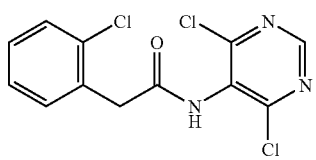

MS (ESI): mass calcd. for $C_{12}H_8Cl_13N_3O$, 315.0; m/z found, 316.0 [M+H]$^+$. $^1$H NMR ((CD$_3$)$_2$SO): 10.52 (s, 1H), 8.85 (s, 1H), 7.51-7.43 (m, 2H), 7.36-7.29 (m, 2H), 3.93 (s, 2H).

Intermediate 8: N-(4,6-Dichloro-pyrimidin-5-yl)-2-phenyl-acetamide

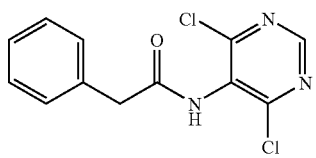

MS (ESI): mass calcd. for $C_{12}H_9Cl_2N_3O$, 281.0; m/z found, 282.0 [M+H]$^+$. $^1$H NMR ((CD$_3$)$_2$SO): 10.51 (s, 1H), 8.85 (s, 1H), 7.40-7.22 (m, 5H), 3.75 (s, 2H).

Intermediate 9: 2-(2,4-Dichloro-phenyl)-N-(4,6-dichloro-pyrimidin-5-yl)-acetamide

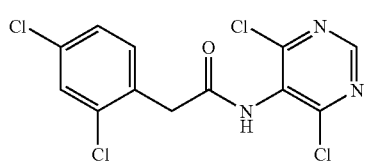

MS (ESI): mass calcd. for $C_{12}H_7Cl_4N_3O$, 348.9; m/z found, 350.0 [M+H]$^+$. $^1$H NMR ((CD$_3$)$_2$SO): 10.53 (s, 1H), 8.86 (s, 1H), 7.62 (d, J=2.1 Hz, 1H), 7.51 (d, J=8.3 Hz, 1H), 7.43 (dd, J=8.2, 2.1 Hz, 1H), 3.94 (s, 2H).

Intermediate 10: N-(4,6-Dichloro-pyrimidin-5-yl)-2-(2-trifluoromethyl-phenyl)-acetamide

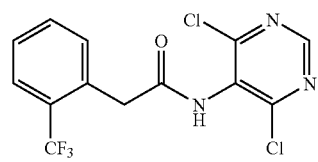

MS (ESI): mass calcd. for $C_{13}H_8Cl_2F_3N_3O$, 349.0; m/z found, 350.0 [M+H]$^+$. $^1$H NMR ((CD$_3$)$_2$SO): 10.52 (s, 1H), 8.85 (s, 1H), 7.73 (d, J=7.8 Hz, 1H), 7.66 (t, J=7.4 Hz, 1H), 7.56 (d, J=7.5 Hz, 1H), 7.51 (t, J=7.6 Hz, 1H), 4.01 (s, 2H).

Intermediate 11: 2-(4-Chloro-phenyl)-N-(4,6-dichloro-pyrimidin-5-yl)-acetamide

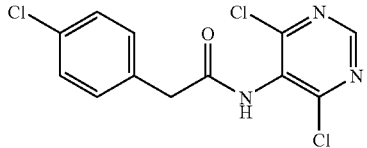

MS (ESI): mass calcd. for $C_{12}H_8Cl_3N_3O$, 315.0; m/z found, 316.0 [M+H]$^+$. $^1$H NMR ((CD$_3$)$_2$SO): 10.54 (s, 1H), 8.86 (s, 1H), 7.50-7.32 (m, 4H), 3.76 (s, 2H).

Intermediate 12: 2-(3-Chlorophenyl)-N-(4,6-dichloropyrimidin-5-yl)acetamide

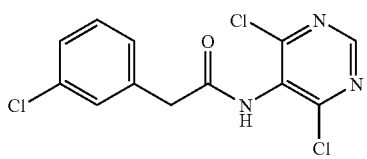

MS (ESI): mass calcd. for $C_{12}H_8Cl_3N_3O$, 315.0; m/z found, 316.0 [M+H]$^+$. $^1$H NMR ((CD$_3$)$_2$SO): 10.57 (s, 1H), 8.86 (s, 1H), 7.49-7.27 (m, 4H), 3.78 (s, 2H).

Intermediate 13: N-(4,6-Dichloro-pyrimidin-5-yl)-2-(2-iodo-phenyl)-acetamide

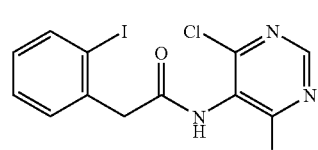

MS (ESI): mass calcd. for $C_{12}H_8Cl_2IN_3O$, 408.0; m/z found 407.9 [M−H]$^-$. $^1$H NMR ((CD$_3$)$_2$SO): 10.49 (s, 1H), 8.85 (s, 1H), 7.89-7.84 (m, 1H), 7.46-7.35 (m, 1H), 7.06-7.00 (m, 2H), 3.94 (s, 2H).

Intermediate 14: 7-Chloro-2-(2,6-dichloro-benzyl)-oxazolo[5,4-d]pyrimidine

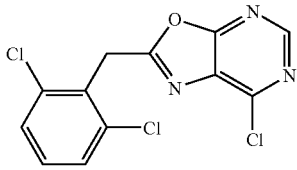

To a solution of 2-(2,6-dichloro-phenyl)-N-(4,6-dichloro-pyrimidin-5-yl)-acetamide (183 mg, 0.52 mmol) in CH$_3$CN (3 mL) was added Cs$_2$CO$_3$ (342 mg, 1.1 mmol). The resulting mixture was heated to 60° C. in a sealed tube. After 2 h, the reaction mixture was cooled and concentrated. The residue was purified by FCC to afford a colorless solid (100 mg, 61%). MS (ESI): mass calcd. for C$_{12}$H$_6$Cl$_3$N$_3$O, 312.9; m/z found, 313.9 [M+H]$^+$. $^1$H NMR (CD$_3$OD): 8.69 (s, 1H), 7.43 (d, J=8.0 Hz, 2H), 7.33-7.28 (m, 1H), 4.72 (s, 2H).

Intermediate 15: 2-(2,6-Dichloro-benzyl)-thiazolo[5,4-d]pyrimidin-7-ol

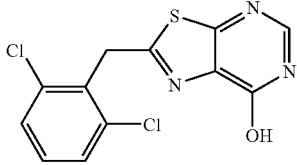

To a mixture of 2-(2,6-dichloro-phenyl)-N-(4,6-dichloro-pyrimidin-5-yl)-acetamide (77.0 g, 221 mmol), thiourea (16.8 g, 221 mmol), and EtOH (500 mL) was added formic acid (3 mL) at rt. The resulting mixture was heated to 90° C. After 12 h, the reaction mixture was cooled and concentrated. The resulting residue was collected by filtration and washed with H$_2$O (100 mL) followed by hexanes (100 mL). The title compound as a dark brown solid was further dried by high vaccum for 12 h and used crude (68 g, 70% apparent purity by analytical HPLC). An analytically pure sample could be obtained by purified by preparative reverse-phase HPLC to afford the title compound as a colorless solid. MS (ESI): mass calcd. for C$_{12}$H$_7$Cl$_2$N$_3$OS, 310.9; m/z found, 312.0 [M+H]$^+$. $^1$H NMR (CD$_3$OD): 8.04 (s, 1H), 7.44-7.37 (m, 2H), 7.31-7.26 (m, 1H), 4.70 (s, 2H).

Intermediate 16: 2-(2,6-Dichloro-benzyl)-5-methyl-sulfanyl-thiazolo[5,4-d]pyrimidin-7-ol

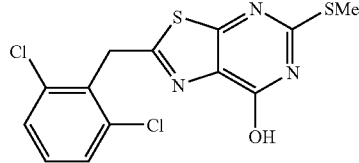

To a mixture of N-(4,6-dichloro-2-methylsulfanyl-pyrimidin-5-yl)-2-(2,6-dichloro-phenyl)-acetamide (10 g, 25 mmol), thiourea (1.9 g, 25 mmol), and EtOH (100 mL) was added formic acid (0.8 mL) at rt. The resulting mixture was heated to 90° C. After 12 h, the reaction mixture was cooled and concentrated. The resulting residue was collected by vacuum filtration and washed with H$_2$O (50 mL) followed by hexanes (50 mL). The title compound purified by FCC to afford 2-(2,6-dichloro-benzyl)-5-methylsulfanyl-thiazolo[5,4-d]pyrimidin-7-ol (1.6 g, 18%) and 2-(2,6-dichloro-benzyl)-7-ethoxy-5-methylsulfanyl-thiazolo[5,4-d]pyrimidine (4 g, 41%) as colorless solids.

Analytical data for 2-(2,6-dichloro-benzyl)-5-methylsulfanyl-thiazolo[5,4-d]pyrimidin-7-ol: MS (ESI): mass calcd. for C$_{13}$H$_9$Cl$_2$N$_3$OS$_2$, 356.96; m/z found, 358.0 [M+H]$^+$. $^1$H NMR ((CD$_3$)$_2$SO): 13.03 (s, 1H), 7.57 (d, J=8.0 Hz, 2H), 7.45-7.39 (m, 1H), 4.64 (s, 2H), 3.32 (s, 3H).

Analytical data for 2-(2,6-dichloro-benzyl)-7-ethoxy-5-methylsulfanyl-thiazolo[5,4-d]pyrimidine: MS (ESI): mass calcd. for C$_{15}$H$_{13}$Cl$_2$N$_3$OS$_2$, 384.9; m/z found, 385.9 [M+H]$^+$. $^1$H NMR ((CD$_3$)$_2$SO): 7.58 (d, J=8.1 Hz, 2H), 7.46-7.42 (m, 1H), 4.73-4.73 (m, 2H), 4.56 (q, J=7.1 Hz, 1H), 2.55 (s, 3H), 1.39 (t, J=9.1 Hz, 3H).

To a mixture of 2-(2,6-dichloro-benzyl)-7-ethoxy-5-methylsulfanyl-thiazolo[5,4-d]pyrimidine (1.7 g, 4.4 mmol), 1,4-dioxane (20 mL), and H$_2$O (4 mL) was added 4 N HCl in dioxane (13 mmol, 3.3 mL) and the resulting solution was heated to 90° C. After 12 h, the solution was cooled and concentrated. The resulting residue was purified by FCC to afford the title compound (980 mg, 62%).

Intermediates 17-24 were prepared using methods analogous to those described for Intermediate 15.

Intermediate 17: 2-(2,6-Dichloro-benzyl)-5-methyl-thiazolo[5,4-d]pyrimidin-7-ol

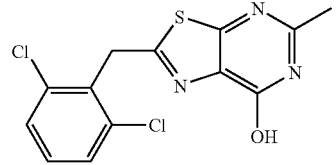

MS (ESI): mass calcd. for C$_{13}$H$_9$Cl$_2$N$_3$OS, 324.9; m/z found, 326.0 [M+H]$^+$. $^1$H NMR ((CD$_3$)$_2$SO): 12.64 (s, 1H), 7.56 (d, J=7.9 Hz, 2H), 7.42 (dd, J=8.6, 7.5 Hz, 1H), 4.66 (s, 2H), 2.35 (s, 3H).

Intermediate 18: 2-(2,4-Dichloro-benzyl)-thiazolo[5,4-d]pyrimidin-7ol

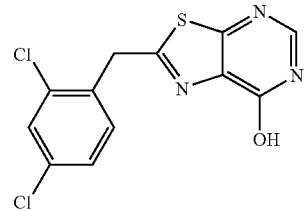

MS (ESI): mass calcd. for C$_{12}$H$_7$Cl$_2$N$_3$OS, 311.0; m/z found, 312.0 [M+H]$^+$. $^1$H NMR ((CD$_3$)$_2$SO): 12.81 (s, 1H), 8.17 (d, J=3.9 Hz, 1H), 7.74-7.34 (m, 3H), 4.53 (s, 2H).

Intermediate 19: 2-(2-Trifluoromethyl-benzyl)-thiazolo[5,4-d]pyrimidin-7-ol

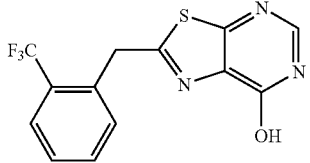

MS (ESI): mass calcd. for $C_{13}H_8F_3N_3OS$, 311.0; m/z found, 312.1 [M+H]$^+$. $^1$H NMR ((CD$_3$)$_2$SO): 12.81 (s, 1H), 8.17 (d, J=3.9 Hz, 1H), 7.89-7.46 (m, 4H), 4.59 (s, 2H).

Intermediate 20: 2-(2-Methyl-benzyl)-thiazolo[5,4-d]pyrimidin-7-ol

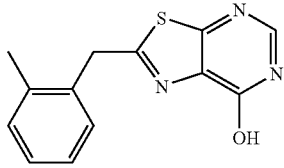

MS (ESI): mass calcd. for $C_{13}H_{11}N_3OS$, 257.1; m/z found, 258.1 [M+H]$^+$.

Intermediate 21: 2-(2-Chloro-benzyl)-thiazolo[5,4-d]pyrimidin-7-ol

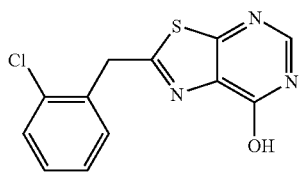

MS (ESI): mass calcd. for $C_{12}H_8ClN_3OS$, 277.0; m/z found, 278.0 [M+H]$^+$.

Intermediate 22: 2-Benzyl-thiazolo[5,4-d]pyrimidin-7-ol

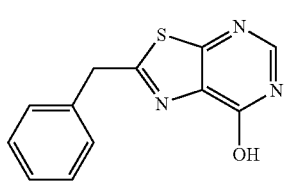

MS (ESI): mass calcd. for $C_{12}H_9N_3OS$, 243.0; m/z found, 244.1 [M+H]$^+$.

Intermediate 23: 2-(4-Chloro-benzyl)-thiazolo[5,4-d]pyrimidin-7-ol

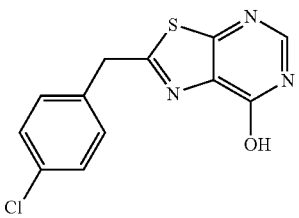

MS (ESI): mass calcd. for $C_{12}H_8ClN_3OS$, 277.0; m/z found, 278.0 [M+H]$^+$.

Intermediate 24: 2-(3-Chloro-benzyl)-thiazolo[5,4-d]pyrimidin-7-ol

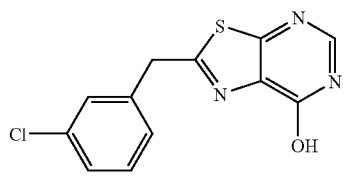

MS (ESI): mass calcd. for $C_{12}H_8ClN_3OS$, 277.0; m/z found, 278.1 [M+H]$^+$.

Intermediate 25: 7-Chloro-2-(2,6-dichloro-benzyl)-thiazolo[5,4-d]pyrimidine

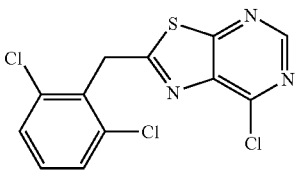

To a mixture of crude 2-(2,6-dichloro-benzyl)-thiazolo[5,4-d]pyrimidin-7-ol (27 g, 87 mmol) in CH$_3$CN (500 mL) was added POCl$_3$ (27 g, 173 mmol) at rt. The resulting mixture was heated to 90° C. After 12 h, the reaction mixture was cooled and added in 50 mL portions to an ice cold solution of satd. aq. NaHCO$_3$ (500 mL), keeping the pH of the biphasic mixture at pH 7 throughout the addition. Once the inverse quench was complete, the biophasic mixture was separated and the organic layer was collected. The aqueous layer was extracted with EtOAc (300 mL×3). The combined organic layers were dried, concentrated, and purified by FCC to afford a colorless solid (8.2 g, 29%). MS (ESI): mass calcd. for $C_{12}H_6Cl_3N_3S$, 328.9; m/z found, 330.0 [M+H]$^+$. $^1$H NMR ((CD$_3$)$_2$SO): 8.98 (s, 1H), 7.61 (d, J=8.1 Hz, 2H), 7.49-7.45 (m, 1H), 4.88 (s, 2H).

Intermediates 26-35 were prepared using methods analogous to those described for Intermediate 25.

Intermediate 26: 7-Chloro-2-(2,6-dichloro-benzyl)-5-methylsulfanyl-thiazolo[5,4-d]pyrimidine

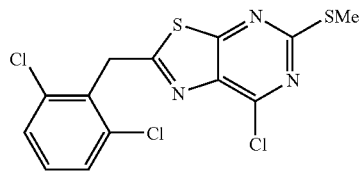

MS (ESI): mass calcd. for $C_{13}H_8Cl_3N_3S_2$, 374.9; m/z found, 375.9 [M+H]$^+$. $^1$H NMR ((CD$_3$)$_2$SO): 7.60 (d, J=8.1 Hz, 2H), 7.46 (dd, J=8.5, 7.7 Hz, 1H), 4.81 (s, 2H), 2.58 (s, 3H).

Intermediate 27: 7-Chloro-2-(2,6-dichloro-benzyl)-5-methyl-thiazolo[5,4-d]pyrimidine

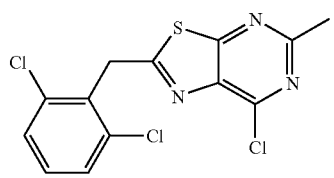

MS (ESI): mass calcd. for $C_{13}H_8Cl_3N_3S$, 342.9; m/z found, 344.0 [M+H]$^+$. $^1$H NMR ((CD$_3$)$_2$SO): 7.60 (d, J=8.1 Hz, 2H), 7.46 (dd, J=8.5, 7.7 Hz, 1H), 4.84 (s, 2H), 2.70 (s, 3H).

Intermediate 28: 7-Chloro-2-(2-methyl-benzyl)-thiazolo[5,4-d]pyrimidine

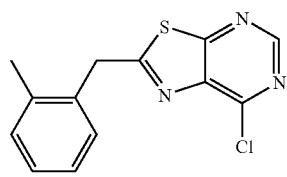

MS (ESI): mass calcd. for $C_{13}H_{10}ClN_3S$, 275.0; m/z found, 276.1 [M+H]$^+$. $^1$H NMR (CDCl$_3$): 8.83 (s, 1H), 7.53-7.04 (m, 4H), 4.51 (s, 2H), 2.34 (s, 3H).

Intermediate 29: 7-Chloro-2-(2-chloro-benzyl)-thiazolo[5,4-d]pyrimidine

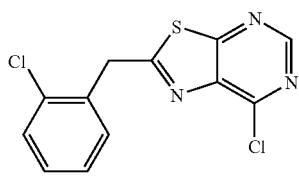

MS (ESI): mass calcd. for $C_{12}H_7Cl_2N_3S$, 295.0; m/z found, 296.0 [M+H]$^+$. $^1$H NMR ((CD$_3$)$_2$SO): 8.97 (s, 1H), 7.65-7.58 (m, 1H), 7.57-7.52 (m, 1H), 7.46-7.39 (m, 2H), 4.73 (s, 2H).

Intermediate 30: 2-Benzyl-7-chloro-thiazolo[5,4-d]pyrimidine

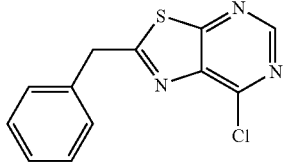

MS (ESI): mass calcd. for $C_{12}H_8ClN_3S$, 261.0; m/z found, 262.0 [M+H]$^+$. $^1$H NMR ((CD$_3$)$_2$SO): 8.97 (d, J=6.2 Hz, 1H), 7.50-7.28 (m, 5H), 4.62 (s, 2H).

Intermediate 31: 7-Chloro-2-(2,4-dichloro-benzyl)-thiazolo[5,4-d]pyrimidine

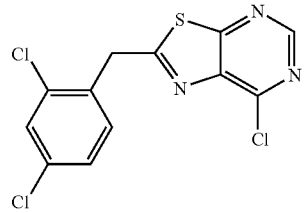

MS (ESI): mass calcd. for $C_{12}H_6Cl_3N_3S$, 328.9; m/z found, 330.0 [M+H]$^+$. $^1$H NMR ((CD$_3$)$_2$SO): 8.98 (s, 1H), 7.73 (d, J=2.2 Hz, 1H), 7.65 (d, J=8.3 Hz, 1H), 7.52 (dd, J=8.3, 2.2 Hz, 1H), 4.74 (s, 2H).

Intermediate 32: 7-Chloro-2-(2-trifluoromethyl-benzyl)-thiazolo[5,4-d]pyrimidine

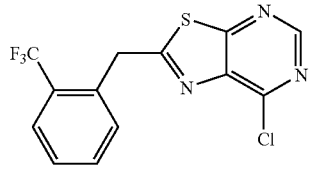

MS (ESI): mass calcd. for $C_{13}H_7ClF_3N_3S$, 329.0; m/z found, 330.0 [M+H]$^+$. $^1$H NMR ((CD$_3$)$_2$SO): 8.98 (s, 1H), 7.83 (d, J=7.8 Hz, 1H), 7.79-7.67 (m, 2H), 7.61 (t, J=7.5 Hz, 1H), 4.80 (s, 2H).

Intermediate 33: 7-Chloro-2-(4-chloro-benzyl)-thiazolo[5,4-d]pyrimidine

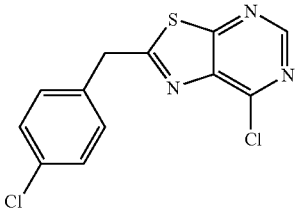

MS (ESI): mass calcd. for $C_{12}H_7Cl_2N_3S$, 295.0; m/z found, 296.0 [M+H]$^+$. $^1$H NMR ((CD$_3$)$_2$SO): 8.97 (s, 1H), 7.53-7.41 (m, 4H), 4.64 (s, 2H).

Intermediate 34: 7-Chloro-2-(3-chloro-benzyl)-thiazolo[5,4-d]pyrimidine

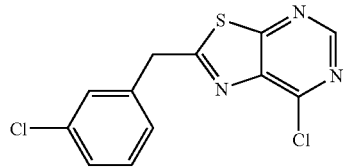

MS (ESI): mass calcd. for C$_{12}$H$_7$Cl$_2$N$_3$S, 295.0; m/z found, 296.0 [M+H]$^+$. $^1$H NMR ((CD$_3$)$_2$SO): 8.96 (s, 1H), 7.55 (s, 1H), 7.46-7.36 (m, 3H), 4.65 (s, 2 H).

Intermediate 35: 7-Chloro-2-(2-iodo-benzyl)-thiazolo[5,4-d]pyrimidine

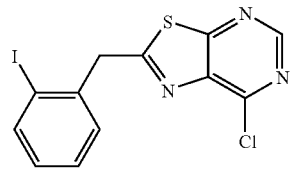

MS (ESI): mass calcd. for C$_{12}$H$_7$ClIN$_3$S, 387.6; m/z found 388.0 [M+H]$^+$. $^1$H NMR (CDCl$_3$): 8.86 (s, 1H), 7.99-7.89 (m, 1H), 7.56-7.34 (m, 1H), 7.13-7.01 (m, 2H), 4.69 (s, 2H).

Intermediate 36: 2-(2-Methanesulfinyl-2-methylsulfanyl-vinyl)-1,3-dimethyl-benzene

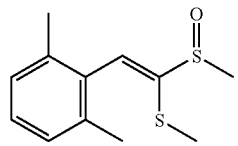

To a solution of 2,6-dimethyl-benzaldehyde (14.6 g, 109 mmol) in 1,4-dioxane (24.7 mL) was added methyl methylsulfinylmethyl sulfide (13.5 g, 109 mmol) followed by benzyltrimethylammonium hydroxide (9.10 g, 54.4 mmol). The resulting mixture was heated at 80° C. After 16 h, the mixture was cooled to rt and concentrated. The resulting residue was purified by FCC to afford a yellow oil (17.9 g, 68%). MS (ESI): mass calcd. for C$_{12}$H$_{16}$OS$_2$, 240.1; m/z found, 241.1 [M+H]$^+$. $^1$H NMR (CDCl$_3$): 7.71 (s, 1H), 7.19-7.13 (m, 1H), 7.07 (d, J=7.5 Hz, 2H), 2.82 (s, 3H), 2.24 (s, 6 H), 2.06 (s, 3H).

Intermediate 37: (2,6-Dimethyl-phenyl)-acetic acid ethyl ester

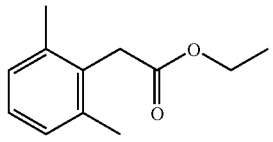

HCl gas was bubbled through a solution of 2-(2-methanesulfinyl-2-methylsulfanyl-vinyl)-1,3-dimethyl-benzene (23.2 g, 96.5 mmol) and EtOH (400 mL) at 0° C. After 45 min, bubbling of HCl was ceased and N$_2$ was bubbled through the solution for an additional 10 min. The resulting solution was concentrated and purified by FCC to afford a colorless oil (13.3 g, 72%). MS (ESI): mass calcd. for C$_{12}$H$_{16}$O$_2$, 192.1; m/z found, 193.2 [M+H]$^+$. $^1$H NMR (CDCl$_3$): 7.09-7.00 (m, 3H), 4.14 (q, J=7.1 Hz, 2H), 3.67 (s, 2H), 2.33 (s, 6H), 1.24 (t, J=7.1 Hz, 3H).

Intermediate 38: (2,6-Dimethyl-phenyl)-acetic acid

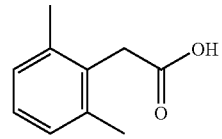

To a mixture of (2,6-dimethyl-phenyl)-acetic acid ethyl ester (13.3 g, 69.2 mmol) in THF (550 mL) and water (224 mL) was added lithium hydroxide monohydrate (23.2 g, 553 mmol). The resulting mixture was stirred vigorously at rt. After 72 h, the mixture was heated to 50° C. for an additional 24 h. The mixture was cooled to rt and concentrated. To the resulting residue was added aqueous 2 N HCl (300 mL) to afford a colorless precipitate. The precipitate was collected by vacuum filtration and further purified by FCC to provide a colorless solid (8.9 g, 78%). MS (ESI): mass calcd. for C$_{10}$H$_{12}$O$_2$, 164.1; m/z found, 163.1 [M–H]$^+$. $^1$H NMR (CDCl$_3$): 7.17-6.90 (m, 3H), 3.72 (s, 2H), 2.33 (s, 6H).

Intermediates 39-41 were prepared using methods analogous to those described for the preceding intermediates.

Intermediate 39: N-(4,6-Dichloro-pyrimidin-5-yl)-2-(2,6-dimethyl-phenyl)-acetamide

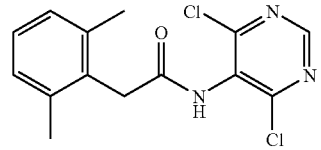

Step A: (2,6-Dimethyl-phenyl)-acetyl chloride $^1$H NMR (CDCl$_3$): 7.20-7.11 (m, 1H), 7.06 (d, J=7.5 Hz, 2H), 4.22 (s, 2H), 2.32 (s, 6H).

Step B

MS (ESI): mass calcd. for C$_{14}$H$_{13}$Cl$_2$N$_3$O, 309.0; m/z found, 310.1 [M+H]$^+$. $^1$H NMR ((CD$_3$)$_2$SO): 10.30 (s, 1H), 8.84 (s, 1H), 7.09-7.00 (m, 3H), 3.81 (s, 2H), 2.32 (s, 6H).

Intermediate 40: 2-(2,6-Dimethyl-benzyl)-thiazolo[5,4-d]pyrimidin-7-ol

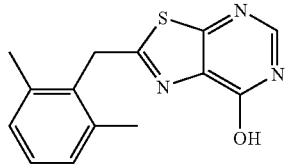

MS (ESI): mass calcd. for C$_{14}$H$_{13}$N$_3$OS, 271.1; m/z found, 272.1 [M+H]$^+$. $^1$H NMR ((CD$_3$)$_2$SO): 12.83-12.67 (m, 1H), 8.13 (s, 1H), 7.05-6.95 (m, 3H), 4.40 (s, 2H), 2.24 (s, 6H).

Intermediate 41: 7-Chloro-2-(2,6-dimethyl-benzyl)-thiazolo[5,4-d]pyrimidine

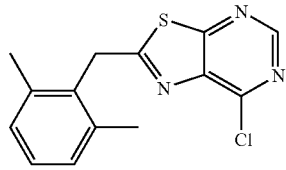

MS (ESI): mass calcd. for $C_{14}H_{12}ClN_3S$, 289.0; m/z found, 290.1 [M+H]$^+$. $^1$H NMR ((CD$_3$)$_2$SO): 8.94 (s, 1H), 7.22-7.08 (m, 3H), 4.59 (s, 2H), 2.33 (s, 6 H).

Intermediate 42: 6-Chloro-pyrimidine-4,5-diamine

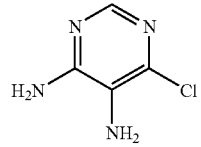

To a 7 N solution of ammonia in MeOH (40 mL) was added 4,6-dichloro-pyrimidin-5-ylamine (8.7 g, 53 mmol) and the solution was heated to 100° C. in a sealed tube. After 12 h, the resulting solution was cooled to rt and allowed to stand for 2 h. The colorless crystalline material that resulted was collected by filtration and washed with ice cold MeOH (10 mL) to give the title compound (5.4 g, 71%). MS (ESI): mass calcd. for $C_4H_5ClN_4$, 144.0; m/z found, 145.0 [M+H]$^+$. $^1$H NMR ((CD$_3$)$_2$SO): 7.64 (s, 1H), 6.70 (s, 2H), 4.93 (s, 2H).

Intermediate 43: (2,6-dichloro-phenyl)-acetaldehyde

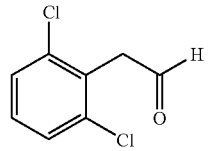

To a solution of 2,6-dichlorophenylethylalcohol (2.0 g, 10.5 mmol) and CH$_2$Cl$_2$ (50 mL) was added acetic acid 1,1-diacetoxy-3-oxo-1λ$^5$-ioda-2-oxa-indan-1-yl ester (Dess-Martin periodinane; 4.9 g, 11.5 mmol) at rt. After 30 min. the mixture was diluted with satd. aq. NaHCO$_3$ (10 mL) and satd. aq. Na$_2$S$_2$O$_3$ (10 mL) and was stirred at rt for 1 h. The mixture was extracted with CH$_2$Cl$_2$ (3×15 mL) and the combined organic layers were dried (MgSO$_4$), concentrated, and purified by FCC to afford a colorless solid (1.4 g, 70%). $^1$H NMR (CDCl$_3$): 9.76 (dd, J=2.24, 1.12 Hz, 1H), 7.38 (d, J=8.1 Hz, 2H). 7.25-7.20 (m, 1H), 4.14 (d, J=0.93 Hz, 1H).

Intermediate 44: 6-Chloro-8-(2,6-dichloro-benzyl)-9H-purine

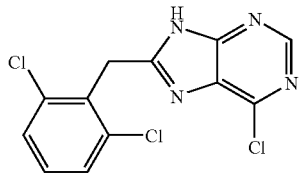

To a mixture of 6-chloro-pyrimidine-4,5-diamine (100 mg, 0.694 mmol), (2,6-dichloro-phenyl)-acetaldehyde (260 mg, 1.38 mmol) and 1,4-dioxane (7 mL) was added 5% FeCl$_3$.SiO$_2$ (150 mg). The resulting mixture was heated to 100° C. in a sealed tube. After 24 h, the mixture was cooled to rt and filtered through a pad of diatomaceous earth, washing with EtOAc (3×10 mL). The filtrate was concentrated and the residue was purified by preparative reverse-phase HPLC to afford the title compound as a white solid (25 mg, 36%). MS (ESI): mass calcd. for $C_{12}H_7Cl_3N_4$, 311.9; m/z found, 313.0 [M+H]$^+$. $^1$H NMR (CDCl$_3$): 8.65 (s, 1H), 7.46 (d, J=8.1 Hz, 2H), 7.34-7.29 (m, 1H), 4.78 (s, 2H).

Intermediate 45: 6-Chloro-N$^4$-(4-trifluoromethyl-phenyl)-pyrimidine-4,5-diamine hydrochloride

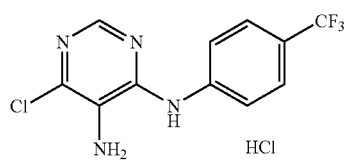

A mixture of 5-amino-4,6-dichloropyrimidine (10.0 g, 61.0 mmol, 1.0 eq), 4-trifluoromethylaniline (8.34 mL, 67.1 mmol, 1.1 eq), EtOH (80 mL), and concentrated HCl (2.5 mL, 30.5 mmol, 0.5 eq) was heated to 80° C. for 24 h and then cooled to rt. The resulting precipitate was collected by filtration, rinsed with EtOH, and dried under vacuum at 50° C. for 18 h to provide the title compound as a white solid (13.9 g, 70%). MS (ESI): mass calcd. for $C_{11}H_9ClF_3N_4$ [M+H]$^+$, 289.0; m/z found, 289.0. $^1$H NMR (d$_6$-DMSO): 9.26 (s, 1H), 8.01 (d, J=8.5 Hz, 2H), 7.94 (s, 1H), 7.67 (d, J=8.6 Hz, 2H), 6.41 (br s, 3H).

Intermediate 46: N-[4-Chloro-6-(4-trifluoromethyl-phenylamino)-pyrimidin-5-yl]-2-(2,6-dichloro-Phenyl)-acetamide

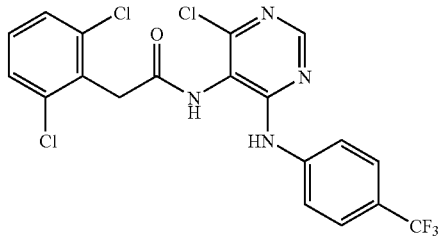

A solution of 2,6-dichlorophenylacetic acid (4.16 g, 20.3 mmol, 1.1 eq), DMF (0.4 mL), and CH$_2$Cl$_2$ (40 mL) under a nitrogen atmosphere was treated with thionyl chloride (1.88 mL, 25.8 mmol, 1.4 equiv.). The resulting mixture was stirred at rt for 20 h. The mixture was concentrated afford (2,6-dichloro-phenyl)-acetyl chloride as a yellow syrup. A solution of the acid chloride in DMA (10 mL) was added to a solution of 6-chloro-N$^4$-(4-trifluoromethyl-phenyl)-pyrimidine-4,5-diamine hydrochloride (6.0 g, 18.5 mmol, 1.0 eq) in DMA (20 mL) under a nitrogen atmosphere. After 2 h, isopropanol (50 mL) was added. The resulting solid precipitate was collected by filtration, rinsed with EtOH, and dried under vacuum at 50° C. for 18 h to give the title compound as a white solid (5.6 g, 64%). $^1$H NMR (d$_6$-DMSO): 9.93 (s, 1H), 9.35

(s, 1H), 8.44 (s, 1H), 7.92 (d, J=8.5 Hz, 2H), 7.74 (d, J=8.7 Hz, 2H), 7.48 (d, J=8.1 Hz, 2H), 7.33 (t, J=7.7 Hz, 1 H), 4.24 (s, 2H).

Example 1

[2-(2,6-Dichloro-benzyl)-oxazolo[5,4-d]pyrimidin-7-yl-]-(4-trifluoromethyl-phenyl)-amine

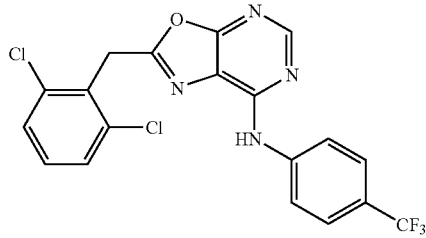

A mixture of 7-chloro-2-(2,6-dichloro-benzyl)-oxazolo[5,4-d]pyrimidine (42 mg, 0.13 mmol), 4-trifluoromethyl-phenylamine (22 mg, 0.13 mmol), and p-TsOH.H$_2$O (51 mg, 0.27 mmol) in toluene (2 mL) was heated to 120° C. in a sealed tube. After 2 h, the solution was cooled purified by preparative reverse-phase HPLC to afford the title compound as a colorless solid (20 mg, 34%). MS (ESI): mass calcd. C$_{19}$H$_{11}$Cl$_2$F$_3$N$_4$O, 438.0; m/z found, 439.1 [M+H]$^+$. $^1$H NMR (CDCl$_3$): 8.57 (s, 1H), 7.90 (d, J=8.6 Hz, 2H), 7.76 (s, 1H), 7.62 (d, J=8.6 Hz, 2H), 7.42 (d, J=8.0 Hz, 2H), 7.31-7.27 (m, 1H), 4.66 (s, 2H).

Example 2

(4-tert-Butyl-phenyl)-[2-(2,6-dichloro-benzyl)-oxazolo[5,4-d]pyrimidin-7-yl]-amine

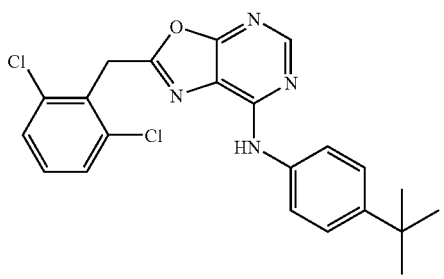

The title compound was prepared using methods analogous to those described in Example 1. MS (ESI): mass calcd. C$_{22}$H$_{20}$Cl$_2$N$_4$O, 426.1; m/z found, 427.2 [M+H]$^+$. $^1$H NMR (CDCl$_3$): 8.47 (s, 1H), 7.51 (d, J=8.4 Hz, 2H), 7.42-7.35 (m, 4H), 7.29-7.23 (m, 1H), 4.63 (s, 2H), 1.32 (s, 9H).

Example 3

[2-(2,6-Dichloro-benzyl)-thiazolo[5,4-d]pyrimidin-7-yl]-(4-trifluoromethyl-phenyl)-amine

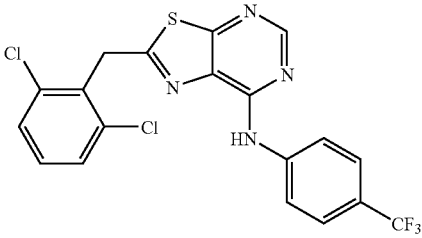

To a solution of 7-chloro-2-(2,6-dichloro-benzyl)-thiazolo[5,4-d]pyrimidine (45.0 mg, 0.15 mmol) and 4-trifluoromethyl-phenylamine (23 mg, 0.15 mmol) in isopropanol (IPA) (2 mL) was added 1.25 M HCl in IPA (0.26 mL, 0.32 mmol). The resulting solution was heated in a sealed tube to 90° C. After 12 h, the solution was cooled and purified by preparative reverse-phase HPLC to afford the title compound as a colorless solid (50 mg, 74%). MS (ESI): mass calcd. for C$_{19}$H$_{11}$Cl$_2$F$_3$N$_4$S, 454.0; m/z found, 455.0 [M+H]$^+$. $^1$H NMR ((CD$_3$)$_2$SO): 10.46 (s, 1H), 8.58 (s, 1H), 8.19 (d, J=8.5 Hz, 2H), 7.71 (d, J=8.7 Hz, 2H), 7.62 (d, J=8.1 Hz, 2H), 7.47 (dd, J=8.5, 7.8 Hz, 1H), 4.82 (s, 2H).

Alternative Preparation:

A solution of N-[4-chloro-6-(4-trifluoromethyl-phenylamino)-pyrimidin-5-yl]-2-(2,6-dichloro-phenyl)-acetamide (3.00 g, 6.31 mmol, 1.0 eq) and thiourea (0.72 g, 9.46 mmol, 1.5 eq) in DMA (18 mL) was treated with HCl (5-6 M in isopropanol; 11.5 mL, 63.1 mmol, 10.0 eq). The reaction mixture was heated to 90° C. for 2 h. Water (7.5 mL) was added, and the reaction mixture was slowly cooled to rt. The resulting solid was collected by filtration, rinsed with EtOH (8 mL), and dried to give a white solid (2.10 g, 73%). The material was suspended in EtOH (18 mL), heated to 80° C. for 30 min, and slowly cooled to rt. The solid was collected by filtration, rinsed with EtOH (5 mL), and dried under vacuum at 50° C. for 18 h to give the title compound (1.95 g, 68%). MS (ESI): mass calcd. for C$_{19}$H$_{12}$Cl$_2$F$_3$N$_4$S, 455.0; m/z found, 455.1 [M+H]$^+$. $^1$H NMR (d$_6$-DMSO): 10.50 (s, 1H), 8.59 (s, 1H), 8.21 (d, J=8.4 Hz, 2H), 7.72 (d, J=8.5 Hz, 2H), 7.63 (d, J=8.1 Hz, 2H), 7.49 (t, J=8.1 Hz, 1H), 4.83 (s, 2H). $^{13}$C NMR (d$_6$-DMSO): 165.7, 162.8, 153.5, 152.4, 142.7, 135.5, 132.4, 130.8, 130.8, 129.0, 125.6 (q, J=3.7 Hz), 124.4 (q, J=271.2 Hz), 123.0 (q, J=37.0 Hz), 121.1, 36.0.

The compounds in Examples 4-61 were prepared using methods analogous to those described for Example 3.

Example 4

[2-(2-Iodo-benzyl)-thiazolo[5,4-d]pyrimidin-7-yl]-(4-trifluoromethyl-phenyl)-amine

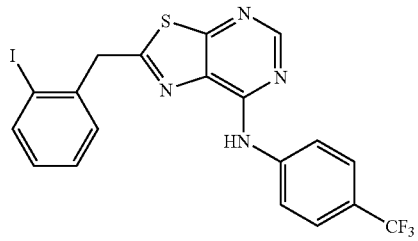

MS (ESI): mass calcd. for $C_{19}H_{12}F_3IN_4S$, 512.3; m/z found 513.0 [M+H]$^+$. $^1$H NMR (CDCl$_3$): 8.64 (s, 1H), 8.13 (s, 1H), 7.99 (d, J=8.4 Hz, 2H), 7.94-7.90 (m, 1H), 7.65 (d, J=8.5 Hz, 2H), 7.43-7.35 (m, 2H), 7.09-7.01 (m, 1H), 4.58 (s, 2H).

Example 5

[2-(2,6-Dichloro-benzyl)-5-methylsulfanyl-thiazolo[5,4-d]pyrimidin-7-yl]-(4-trifluoromethyl-phenyl)-amine

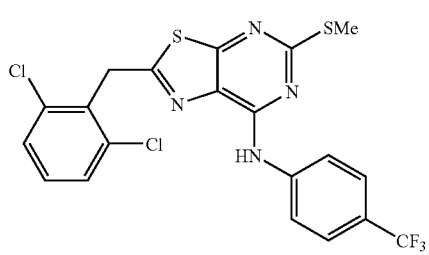

MS (ESI): mass calcd. for $C_{20}H_{13}Cl_2F_3N_4S_2$, 499.9; m/z found, 501.0 [M+H]$^+$. $^1$H NMR ((CD$_3$)$_2$SO): 10.45 (s, 1H), 8.12 (d, J=8.6 Hz, 2H), 7.72 (d, J=8.7 Hz, 2 H), 7.61 (d, J=8.1 Hz, 2H), 7.49-7.44 (m, 1H), 4.78 (s, 2H), 2.52 (s, 3H).

Example 6

[2-(2,6-Dichloro-benzyl)-5-methyl-thiazolo[5,4-d]pyrimidin-7-yl]-(4-trifluoromethyl-phenyl)-amine

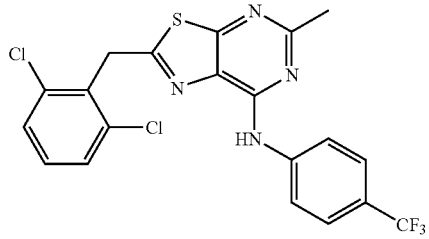

MS (ESI): mass calcd. for $C_{20}H_{13}Cl_2F_3N_4S$, 468.0; m/z found, 469.0 [M+H]$^+$. $^1$H NMR ((CD$_3$)$_2$SO): 10.30 (s, 1H), 8.21 (d, J=7.8 Hz, 2H), 7.70 (d, J=7.9 Hz, 2H), 7.62 (d, J=7.9 Hz, 2H), 7.47 (t, J=8.2 Hz, 1H), 4.80 (s, 2H), 2.56 (s, 3H).

Example 7

[2-(2,6-Dichloro-benzyl)-5-methyl-thiazolo[5,4-d]pyrimidin-7-yl]-(6-trifluoromethyl-pyridin-3-yl)-amine

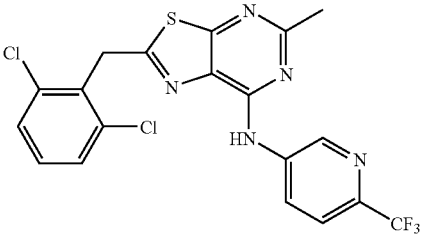

MS (ESI): mass calcd. for $C_{19}H_{12}Cl_2F_3N_5S$, 469.0; m/z found, 470.0 [M+H]$^+$. $^1$H NMR ((CD$_3$)$_2$SO): 10.58 (s, 1H), 9.33 (d, J=2.1 Hz, 1H), 8.67 (dd, J=8.4, 1.9 Hz, 1H), 7.89 (d, J=8.7 Hz, 1H), 7.62 (d, J=8.1 Hz, 2H), 7.50-7.46 (m, 1H), 4.81 (s, 2H), 2.58 (s, 3H).

Example 8

[2-(2,6-Dichloro-benzyl)-thiazolo[5,4-d]pyrimidin-7-yl]-(6-trifluoromethyl-pyridin-3-yl)-amine

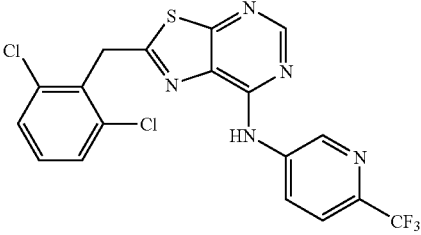

MS (ESI): mass calcd. for $C_{18}H_{10}Cl_2F_3N_5S$, 454.9 m/z found, 456.0 [M+H]$^+$. $^1$H NMR ((CD$_3$)$_2$SO): 10.69 (s, 1H), 9.26 (d, J=2.3 Hz, 1H), 8.67 (dd, J=8.6, 2.2 Hz, 1H), 8.62 (s, 1H), 7.90 (d, J=8.6 Hz, 1H), 7.63 (d, J=8.1 Hz, 2H), 7.51-7.46 (m, 1H), 4.84 (s, 2H).

Example 9

(3-Chloro-4-trifluoromethyl-phenyl)-[2-(2,6-dichloro-benzyl)-thiazolo[5,4-d]pyrimidin-7-yl]-amine

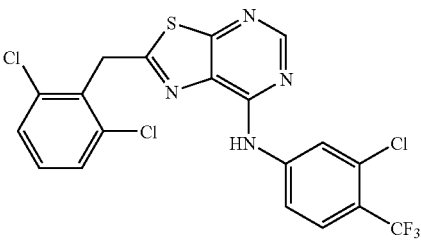

MS (ESI): mass calcd. for $C_{19}H_{10}Cl_3F_3N_4S$, 487.9 m/z found, 489.0 [M+H]$^+$. $^1$H NMR (CD$_3$OD): 8.52 (s, 1H), 8.29

(d, J=1.5 Hz, 1H), 7.89-7.86 (m, 1H), 7.64 (d, J=8.7 Hz, 1H), 7.44 (d, J=8.0 Hz, 2H), 7.33-7.28 (m, 1H), 4.80 (s, 2H).

Example 10

2-{4-[2-(2,6-Dichloro-benzyl)-5-methyl-thiazolo[5,4-d]pyrimidin-7-ylamino]-phenyl}-2-methyl-propionitrile

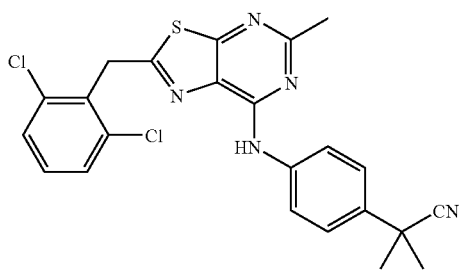

MS (ESI): mass calcd. for $C_{23}H_{19}Cl_2N_5S$, 467.0 m/z found, 468.0 [M+H]$^+$. $^1$H NMR ((CD$_3$)$_2$SO): 10.19 (s, 1H), 7.97 (d, J=8.7 Hz, 2H), 7.62 (d, J=8.1 Hz, 2H), 7.53-7.45 (m, 3H), 4.79 (s, 2H), 2.53 (s, 3H), 1.70 (s, 6H).

Example 11

[2-(2,6-Dichloro-benzyl)-5-methyl-thiazolo[5,4-d]pyrimidin-7-yl]-(3-fluoro-4-methanesulfonyl-phenyl)-amine

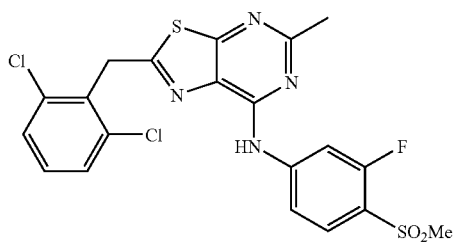

MS (ESI): mass calcd. for $C_{20}H_{15}Cl_2FN_4O_2S_2$, 495.9 m/z found, 497.0 [M+H]$^+$. $^1$H NMR ((CD$_3$)$_2$SO): 10.62 (s, 1H), 8.27 (dd, J=13.5, 1.5 Hz, 1H), 8.06 (dd, J=8.9, 1.4 Hz, 1H), 7.80 (t, J=8.6 Hz, 1H), 7.62 (d, J=8.1 Hz, 2H), 7.48 (t, J=8.1 Hz, 1H), 4.81 (s, 2H), 3.30 (s, 3H), 2.60 (s, 3H).

Example 12

[2-(2,6-Dichloro-benzyl)-5-methyl-thiazolo[5,4-d]pyrimidin-7-yl]-(4-trifluoromethyl-phenyl)-amine

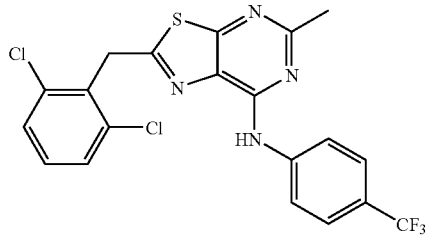

MS (ESI): mass calcd. for $C_{20}H_{13}Cl_2F_3N_4S$, 468.0; m/z found, 469.0 [M+H]$^+$. $^1$H NMR ((CD$_3$)$_2$SO): 10.29 (s, 1H), 8.20 (d, J=8.4 Hz, 2H), 7.69 (d, J=8.4 Hz, 2H), 7.61 (d, J=8.1 Hz, 2H), 7.47 (t, J=8.1 Hz, 1H), 4.79 (s, 2H), 2.55 (s, 3H).

Example 13

[2-(2,6-Dichloro-benzyl)-thiazolo[5,4-d]pyrimidin-7-yl]-(4-methanesulfonyl-phenyl)-amine

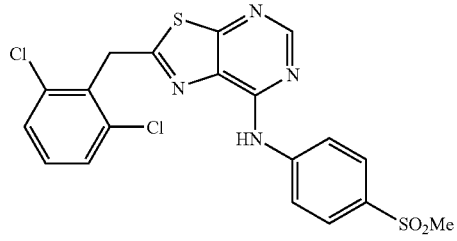

MS (ESI): mass calcd. for $C_{19}H_{14}Cl_2N_4O_2S_2$, 463.9; m/z found, 465.0 [M+H]$^+$. $^1$H NMR ((CD$_3$)$_2$SO): 10.53 (s, 1H), 8.61 (s, 1H), 8.24-8.21 (m, 2H), 7.91-7.88 (m, 2H), 7.63 (d, J=8.1 Hz, 2H), 7.49 (dd, J=8.4, 7.8 Hz, 1H), 4.84 (s, 2H), 3.19 (s, 3H).

Example 14

[2-(2,6-Dichloro-benzyl)-thiazolo[5,4-d]pyrimidin-7-yl]-(4-trifluoromethanesulfonyl-phenyl)-amine

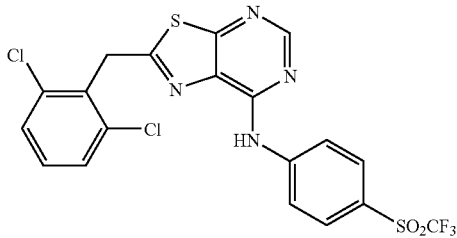

MS (ESI): mass calcd. for $C_{19}H_{11}Cl_2F_3N_4O_2S_2$, 517.9 m/z found, 519.0 [M+H]$^+$. $^1$H NMR (CDCl$_3$): 8.76 (s, 1H), 8.52 (d, J=1.3 Hz, 1H), 8.23 (d, J=9.0 Hz, 2H), 8.07 (d, J=8.8 Hz, 2H), 7.45 (d, J=8.1 Hz, 2H), 7.32 (dd, J=8.5, 7.7 Hz, 1H), 4.84 (s, 2H).

Example 15

[2-(2,6-Dichloro-benzyl)-thiazolo[5,4-d]pyrimidin-7-yl]-[4-(morpholine-4-sulfonyl)-phenyl]-amine

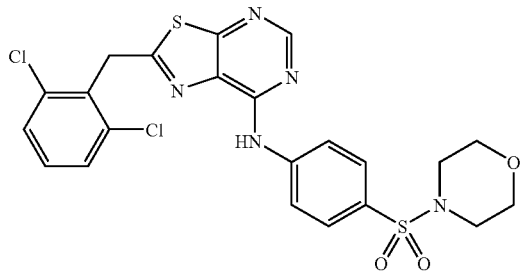

MS (ESI): mass calcd. for $C_{22}H_{19}Cl_2N_5O_3S_2$, 535.0 m/z found, 536.0 [M+H]$^+$. $^1$H NMR ((CD$_3$)$_2$SO): 10.55 (s, 1H), 8.62 (s, 1H), 8.27 (d, J=8.8 Hz, 2H), 7.72 (d, J=8.8 Hz, 2H), 7.63 (d, J=8.1 Hz, 2H), 7.51-7.46 (m, 1H), 4.84 (s, 2H), 3.66-3.62 (m, 4H), 2.90-2.86 (m, 4H).

Example 16

[2-(2,6-Dichloro-benzyl)-thiazolo[4-d]pyrimidin-7-yl]-[4-(4-methyl-piperazine-1-sulfonyl)-phenyl]-amine

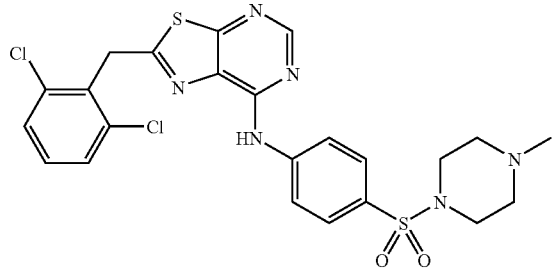

MS (ESI): mass calcd. for $C_{23}H_{22}Cl_2N_6O_2S_2$, 548.0 m/z found, 549.1 [M+H]$^+$. $^1$H NMR ((CD$_3$)$_2$SO): 10.53 (s, 1H), 8.61 (s, 1H), 8.25 (d, J=8.9 Hz, 2H), 7.71 (d, J=8.9 Hz, 2H), 7.63 (d, J=8.0 Hz, 2H), 7.48 (dd, J=8.6, 7.6 Hz, 1H), 4.84 (s, 2H), 2.95-2.83 (m, 4H), 2.42-2.35 (m, 4H), 2.15 (s, 3H).

Example 17

2-(2-Methylbenzyl)-N-[4-(trifluoromethyl)phenyl][1,3]thiazolo[5,4-d]pyrimidin-7-amine

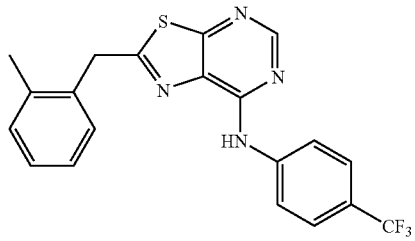

MS (ESI): mass calcd. for $C_{20}H_{15}F_3N_4S$, 400.1; m/z found, 401.1 [M+H]$^+$. $^1$H NMR ((CD$_3$)$_2$SO): 10.49 (s, 1H), 8.58 (s, 1H), 8.22 (d, J=8.5 Hz, 2H), 7.72 (d, J=8.7 Hz, 2H), 7.41-7.36 (m, 1H), 7.29-7.22 (m, 3H), 4.55 (s, 2H), 2.33 (s, 3H).

Example 18

2-(2-Methylbenzyl)-N-[6-(trifluoromethyl)pyridin-3-yl][1,3]thiazolo[5,4-d]pyrimidin-7-amine

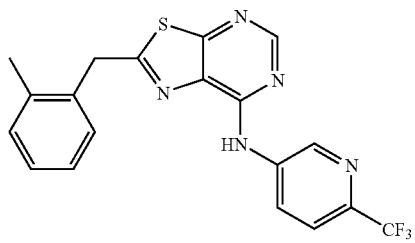

MS (ESI): mass calcd. for $C_{19}H_{14}F_3N_5S$, 401.1; m/z found, 402.1 [M+H]$^+$. $^1$H NMR ((CD$_3$)$_2$SO): 10.77 (s, 1H), 9.29 (d, J=2.4 Hz, 1H), 8.72 (dd, J=8.6, 2.3 Hz, 1H), 8.62 (s, 1H), 7.92 (d, J=8.7 Hz, 1H), 7.42-7.34 (m, 1H), 7.30-7.20 (m, 3 H), 4.56 (s, 2H), 2.30 (s, 3H).

Example 19

2-(2-Methylbenzyl)-N-[4-(methylsulfonyl)phenyl][1,3]thiazolo[5,4-d]pyrimidin-7-amine

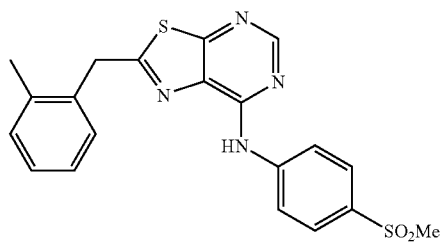

MS (ESI): mass calcd. for $C_{20}H_{18}N_4O_2S_2$, 410.1; m/z found, 411.1 [M+H]$^+$. $^1$H NMR ((CD$_3$)$_2$SO): 10.54 (s, 1H), 8.60 (s, 1H), 8.31-8.20 (m, 2H), 7.95-7.84 (m, 2H), 7.41-7.36 (m, 1H), 7.29-7.22 (m, 3H), 4.55 (s, 2H), 3.19 (s, 3H), 2.31 (s, 3H).

Example 20

2-(2-Chlorobenzyl)-N-[4-(trifluoromethyl)phenyl][1,3]thiazolo[5,4-d]pyrimidin-7-amine

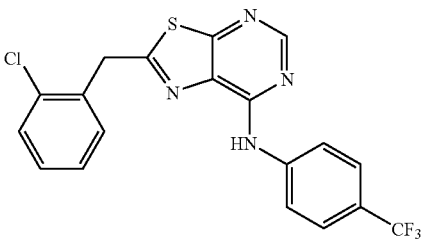

MS (ESI): mass calcd. for $C_{19}H_{12}ClF_3N_4S$, 420.0; m/z found, 421.1 [M+H]$^+$. $^1$H NMR ((CD$_3$)$_2$SO): 10.51 (s, 1H), 8.59 (s, 1H), 8.21 (d, J=8.4 Hz, 2H), 7.72 (s, J=8.7 Hz, 2H), 7.65-7.52 (m, 2H), 7.47-7.39 (m, 2H), 4.68 (s, 2H).

Example 21

2-(2-Chlorobenzyl)-N-[6-(trifluoromethyl)pyridin-3-yl][1,3]thiazolo[5,4-d]pyrimidin-7-amine

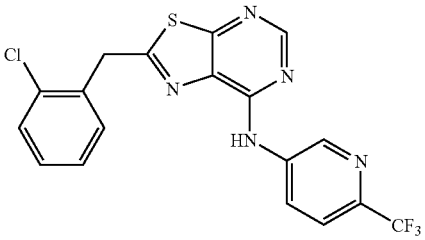

MS (ESI): mass calcd. for $C_{18}H_{11}ClF_3N_5S$, 421.0; m/z found, 422.1 [M+H]$^+$. $^1$H NMR ((CD$_3$)$_2$SO): 10.78 (s, 1H), 9.28 (d, J=2.4 Hz, 1H), 8.71 (dd, J=8.6, 2.3 Hz, 1H), 8.63 (s, 1H), 7.92 (d, J=8.7 Hz, 1H), 7.64-7.54 (m, 2H), 7.46-7.40 (m, 2 H), 4.69 (s, 2H).

Example 22

2-(2-Chlorobenzyl)-N-[4-(methylsulfonyl)phenyl][1,3]thiazolo[5,4-d]pyrimidin-7-amine

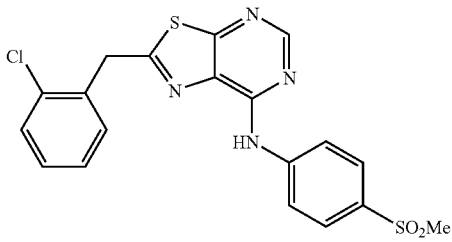

MS (ESI): mass calcd. for $C_{19}H_{15}ClN_4O_2S_2$, 430.0; m/z found, 431.0 [M+H]$^+$. $^1$H NMR ((CD$_3$)$_2$SO): 10.61 (s, 1H), 8.62 (s, 1H), 8.32-8.19 (m, 2H), 7.96-7.84 (m, 2H), 7.66-7.52 (m, 2H), 7.47-7.39 (m, 2H), 4.69 (s, 2H), 3.20 (s, 3H).

Example 23

2-(2,6-Dichlorobenzyl)-N-[2-(trifluoromethyl)phenyl][1,3]thiazolo[5,4-d]pyrimidin-7-amine

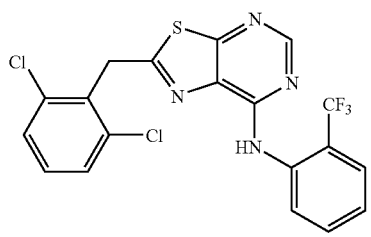

MS (ESI): mass calcd. for $C_{19}H_{11}Cl_2F_3N_4S$, 454.0; m/z found, 455.0 [M+H]$^+$. $^1$H NMR ((CD$_3$)$_2$SO): 9.69 (s, 1H), 8.35 (s, 1H), 7.81-7.42 (m, 7H), 4.77 (s, 2 H).

Example 24

2-(2,6-Dichlorobenzyl)-N-[3-(trifluoromethyl)phenyl][1,3]thiazolo[5,4-d]pyrimidin-7-amine

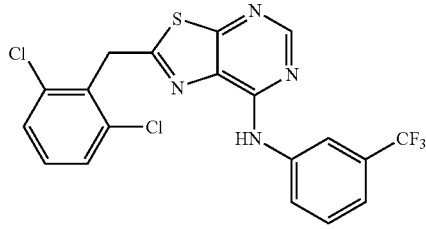

MS (ESI): mass calcd. for $C_{19}H_{11}Cl_2F_3N_4S$, 454.0; m/z found, 455.0 [M+H]$^+$. $^1$H NMR ((CD$_3$)$_2$SO): 10.43 (s, 1H),
8.58 (s, 1H), 8.42 (s, 1H), 8.24 (d, J=8.2 Hz, 1H), 7.68-7.54 (m, 3H), 7.53-7.40 (m, 2H), 4.83 (s, 2H).

Example 25

N-(4-tert-Butylphenyl)-2-(2,6-dichlorobenzyl)[1,3]thiazolo[5,4-d]pyrimidin-7-amine

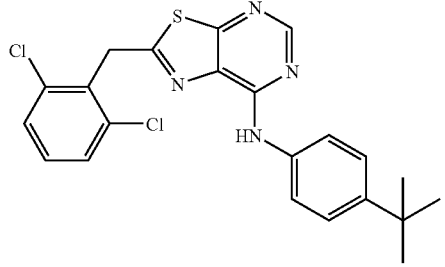

MS (ESI): mass calcd. for $C_{22}H_{20}Cl_2N_4S$, 442.1; m/z found, 443.1 [M+H]$^+$. $^1$H NMR ((CD$_3$)$_2$SO): 10.03 (s, 1H), 8.44 (s, 1H), 7.80-7.70 (m, 2H), 7.63 (d, J=8.0 Hz, 2H), 7.53-7.44 (m, 1H), 7.41-7.33 (m, 2H), 4.81 (s, 2H), 1.29 (s, 9H).

Example 26

Methyl 2-(4-{[2-(2,6-dichlorobenzyl)[1,3]thiazolo[5,4-d]pyrimidin-7-yl]amino}phenyl)-2-methylpropanoate

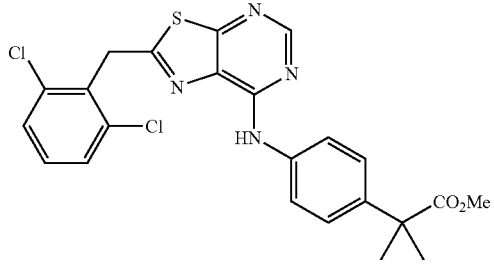

MS (ESI): mass calcd. for $C_{23}H_{20}Cl_2N_4O_2S$, 486.1; m/z found, 487.1 [M+H]$^+$. $^1$H NMR ((CD$_3$)$_2$SO): 10.06 (s, 1H), 8.46 (s, 1H), 7.81 (d, J=8.6 Hz, 2H), 7.63 (d, J=8.0 Hz, 2H), 7.52-7.45 (m, 1H), 7.30 (d, J=8.6 Hz, 2H), 4.81 (s, 2H), 3.61 (s, 3H), 1.52 (s, 6H).

Example 27

2-(2,4-Dichlorobenzyl)-N-[4-(trifluoromethyl)phenyl][1,3]thiazolo[5,4-d]pyrimidin-7-amine

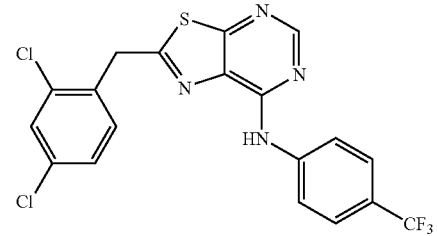

MS (ESI): mass calcd. for $C_{19}H_{11}Cl_2F_3N_4S$, 454.0; m/z found, 455.0 [M+H]$^+$. $^1$H NMR ((CD$_3$)$_2$SO): 10.49 (s, 1H), 8.60 (s, 1H), 8.20 (d, J=8.6 Hz, 2H), 7.76-7.70 (m, 3H), 7.64 (d, J=8.3 Hz, 1H), 7.53 (dd, J=8.3, 2.2 Hz, 1H), 4.68 (s, 2H).

Example 28

2-(2,6-Dichlorobenzyl)-N-[4-(piperazin-1-ylsulfonyl)phenyl][1,3]thiazolo[5,4-d]pyrimidin-7-amine

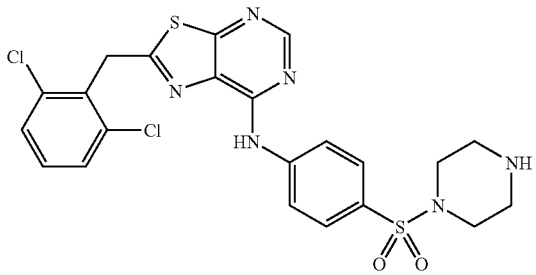

MS (ESI): mass calcd. for $C_{22}H_{20}Cl_2N_6O_2S_2$, 534.0; m/z found, 535.1 [M+H]$^+$. $^1$H NMR ((CD$_3$)$_2$SO): 10.66 (s, 1H), 8.63 (s, 1H), 8.33-8.25 (m, 2H), 7.84-7.73 (m, 2H), 7.65 (d, J=8.0 Hz, 2H), 7.54-7.46 (m, 1H), 4.84 (s, 2H), 3.24-3.14 (m, 4 H), 3.13-3.06 (m, 4H).

Example 29

2-(2,4-Dichlorobenzyl)-N-[6-(trifluoromethyl)pyridin-3-yl][1,3]thiazolo[5,4-d]pyrimidine-7-amine

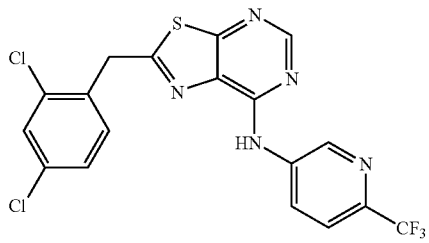

MS (ESI): mass calcd. for $C_{18}H_{10}Cl_2F_3N_5S$, 455.0; m/z found, 456.0 [M+H]$^+$. $^1$H NMR ((CD$_3$)$_2$SO): 10.76 (s, 1H), 9.27 (d, J=2.4 Hz, 1H), 8.70 (dd, J=8.7, 2.3 Hz, 1H), 8.64 (s, 1H), 7.92 (d, J=8.7 Hz, 1H), 7.75 (d, J=2.2 Hz, 1H), 7.64 (d, J=8.3 Hz, 1H), 7.53 (dd, J=8.3, 2.2 Hz, 1H), 4.69 (s, 2H).

Example 30

2-[2-(Trifluoromethyl)benzyl]-N-[4-(trifluoromethyl)phenyl][1,3]thiazolo[5,4-d]pyrimidin-7-amine

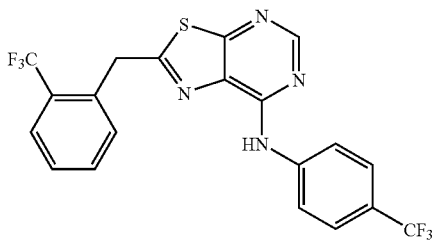

MS (ESI): mass calcd. for $C_{20}H_{12}F_6N_4S$, 454.1; m/z found, 455.1 [M+H]$^+$. $^1$H NMR ((CD$_3$)$_2$SO): 10.51 (s, 1H), 8.60 (s, 1H), 8.21 (d, J=8.6 Hz, 2H), 7.84 (d, J=7.8 Hz, 1H), 7.79-7.68 (m, 4H), 7.61 (t, J=7.6 Hz, 1H), 4.74 (s, 2H).

Example 31

2-[2-(Trifluoromethyl)benzyl]-N-[6-(trifluoromethyl)pyridin-3-yl][1,3]thiazolo[5,4-d]pyrimidin-7-amine

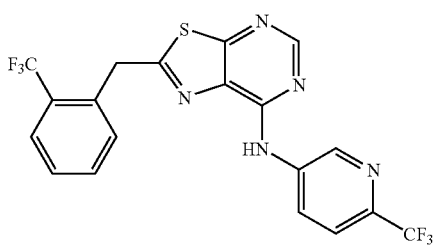

MS (ESI): mass calcd. for $C_{19}H_{11}F_6N_5S$, 455.1; m/z found, 456.1 [M+H]$^+$. $^1$H NMR ((CD$_3$)$_2$SO): 10.77 (s, 1H), 9.28 (d, J=2.4 Hz, 1H), 8.71 (dd, J=8.6, 2.3 Hz, 1H), 8.63 (s, 1H), 7.93 (d, J=8.7 Hz, 1H), 7.84 (d, J=7.9 Hz, 1H), 7.77 (t, J=7.4 Hz, 1H), 7.70 (d, J=7.4 Hz, 1H), 7.61 (t, J=7.6 Hz, 1H), 4.76 (s, 2H).

Example 32

2-Benzyl-N-[4-(trifluoromethyl)phenyl][1,3]thiazolo[5,4-d]pyrimidin-7-amine

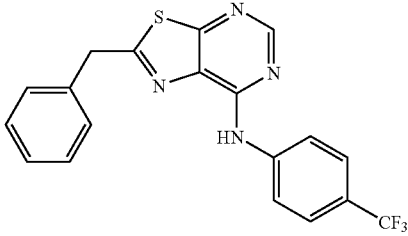

MS (ESI): mass calcd. for $C_{19}H_{13}F_3N_4S$, 386.1; m/z found, 387.1 [M+H]$^+$. $^1$H NMR ((CD$_3$)$_2$SO): 10.51 (s, 1H), 8.59 (s, 1H), 8.22 (d, J=8.6 Hz, 2H), 7.72 (d, J=8.7 Hz, 2H), 7.51-7.27 (m, 5H), 4.57 (s, 2H).

Example 33

2-Benzyl-N-[6-(trifluoromethyl)pyridin-3-yl][1,3]thiazolo[5,4-d]pyrimidin-7-amine

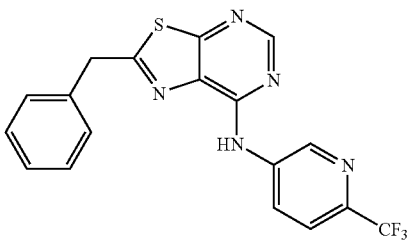

MS (ESI): mass calcd. for $C_{18}H_{12}F_3N_5S$, 387.1; m/z found, 388.1 [M+H]$^+$. $^1$H NMR ((CD$_3$)$_2$SO): 10.78 (s, 1H), 9.29 (d, J=2.3 Hz, 1H), 8.72 (dd, J=8.6, 2.3 Hz, 1H), 8.63 (s, 1H), 7.92 (d, J=8.7 Hz, 1H), 7.51-7.26 (m, 5H), 4.58 (s, 2H).

Example 34

2-Benzyl-N-[4-(methylsulfonyl)phenyl][1,3]thiazolo[5,4-d]pyrimidin-7-amine

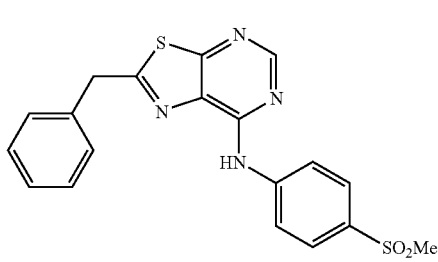

MS (ESI): mass calcd. for $C_{19}H_{16}N_4O_2S_2$, 396.1; m/z found, 397.1 [M+H]$^+$. $^1$H NMR ((CD$_3$)$_2$SO): 10.61 (s, 1H), 8.61 (s, 1H), 8.31-8.22 (m, 2H), 7.95-7.85 (m, 2H), 7.47-7.29 (m, 5H), 4.57 (s, 2H), 3.20 (s, 3H).

Example 35

2-(4-Chlorobenzyl)-N-[4-(trifluoromethyl)phenyl][1,3]thiazolo[5,4-d]pyrimidin-7-amine

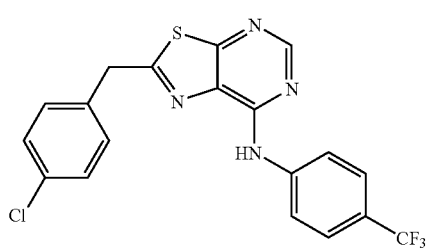

MS (ESI): mass calcd. for $C_{19}H_{12}ClF_3N_4S$, 420.0; m/z found, 421.1 [M+H]$^+$. $^1$H NMR ((CD$_3$)$_2$SO): 10.51 (s, 1H), 8.60 (s, 1H), 8.21 (d, J=8.5 Hz, 2H), 7.72 (d, J=8.7 Hz, 2H), 7.46 (s, 4H), 4.58 (s, 2H).

Example 36

2-(4-Chlorobenzyl)-N-[6-(trifluoromethyl)pyridin-3-yl][1,3]thiazolo[5,4-d]pyrimidin-7-amine

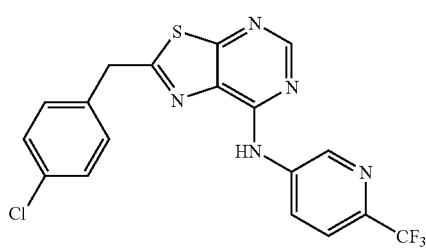

MS (ESI): mass calcd. for $C_{18}H_{11}ClF_3N_5S$, 421.0; m/z found, 422.1 [M+H]$^+$. $^1$H NMR ((CD$_3$)$_2$SO): 10.79 (s, 1H), 9.29 (d, J=2.4 Hz, 1H), 8.71 (dd, J=8.6, 2.3 Hz, 1H), 8.64 (s, 1H), 7.93 (d, J=8.7 Hz, 1H), 7.47 (s, 4H), 4.59 (s, 2H).

Example 37

2-(2,6-Dichlorobenzyl)-N-(4-methoxyphenyl)[1,3]thiazolo[5,4-d]pyrimidin-7-amine

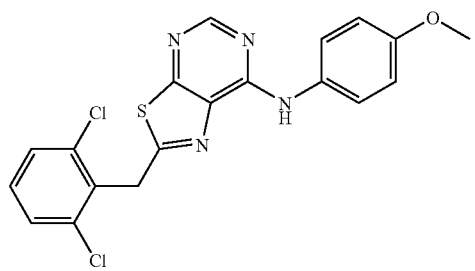

MS (ESI): mass calcd. for $C_{19}H_{14}Cl_2N_4OS$, 416.0; m/z found, 417.0 [M+H]$^+$. $^1$H NMR ((CD$_3$)$_2$SO): 9.90 (s, 1H), 8.41 (s, 1H), 7.75-7.69 (m, 2H), 7.62 (d, J=8.1 Hz, 2H), 7.51-7.44 (m, 1H), 6.96-6.90 (m, 2H), 4.80 (s, 2H), 3.76 (s, 3H).

Example 38

2-(2,6-Dichlorobenzyl)-N-[6-(methylsulfanyl)pyridin-3-yl][1,3]thiazolo[5,4-d]pyrimidin-7-amine

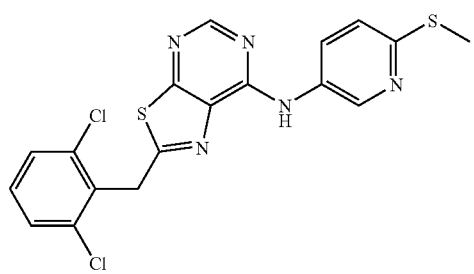

MS (ESI): mass calcd. for $C_{18}H_{13}Cl_2N_5S_2$, 433.0; m/z found, 434.0 [M+H]$^+$. $^1$H NMR ((CD$_3$)$_2$SO): 10.70-9.68 (m, 1H), 9.07-8.71 (m, 1H), 8.49 (s, 1H), 8.17 (dd, J=8.7, 2.6 Hz, 1H), 7.63 (d, J=8.0 Hz, 2H), 7.51-7.45 (m, 1H), 7.32 (d, J=8.7 Hz, 1H), 4.82 (s, 2H), 2.53 (s, 3H).

Example 39

2-(2,6-Dichlorobenzyl)-N-(4-fluorophenyl)[1,3]thiazolo[5,4-d]pyrimidin-7-amine

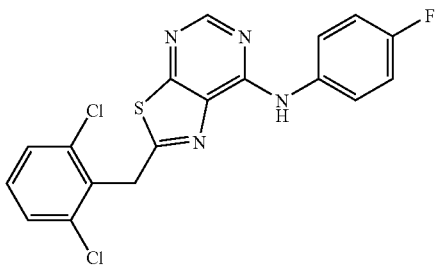

MS (ESI): mass calcd. for $C_{18}H_{11}Cl_2FN_4S$, 404.0; m/z found, 405.0 [M+H]$^+$. $^1$H NMR ((CD$_3$)$_2$SO): 10.10 (s, 1H), 8.47 (s, 1H), 7.96-7.79 (m, 2H), 7.62 (d, J=8.1 Hz, 2H), 7.50-7.46 (m, 1H), 7.27-7.13 (m, 2H), 4.81 (s, 2H).

Example 40

N-(4-Chlorophenyl)-2-(2,6-dichlorobenzyl)[1,3]thiazolo[5,4-d]pyrimidin-7-amine

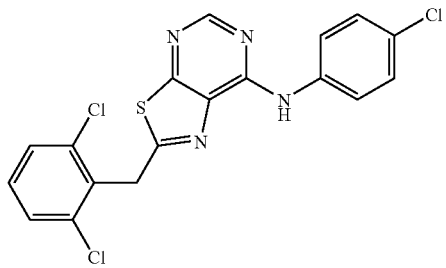

MS (ESI): mass calcd. for $C_{18}H_{11}Cl_3N_4S$, 420.0; m/z found, 421.0 $[M+H]^+$. $^1$H NMR ($(CD_3)_2SO$): 10.19 (s, 1H), 8.51 (s, 1H), 8.05-7.90 (m, 2H), 7.62 (d, J=8.2 Hz, 2H), 7.53-7.38 (m, 3H), 4.81 (s, 2H).

Example 41

N-(4-Bromophenyl)-2-(2,6-dichlorobenzyl)[1,3]thiazolo[5,4-d]pyrimidin-7-amine

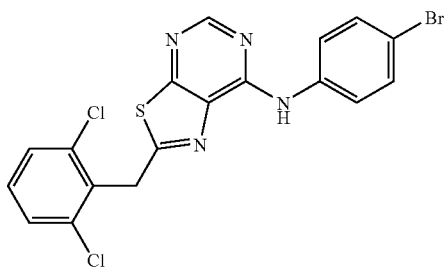

MS (ESI): mass calcd. for $C_{18}H_{11}BrCl_2N_4S$, 463.9; m/z found, 464.9 $[M+H]^+$. $^1$H NMR ($(CD_3)_2SO$): 10.19 (s, 1H), 8.52 (s, 1H), 7.96-7.86 (m, 2H), 7.63 (d, J=8.1 Hz, 2H), 7.57-7.52 (m, 2H), 7.51-7.45 (m, 1H), 4.81 (s, 2H).

Example 42

2-(4-{[2-(2,6-Dichlorobenzyl)[1,3]thiazolo[5,4-d]pyrimidin-7-yl]amino}phenyl)-2-methylpropanenitrile

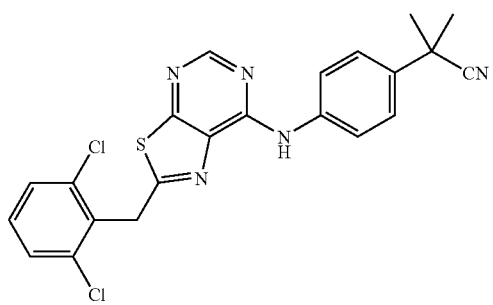

MS (ESI): mass calcd. for $C_{22}H_{17}Cl_2N_5S$, 453.1; m/z found, 454.1 $[M+H]^+$. $^1$H NMR ($(CD_3)_2SO$): 10.15 (s, 1H), 8.49 (s, 1H), 8.00-7.87 (m, 2H), 7.63 (d, J=8.1 Hz, 2H), 7.53-7.46 (m, 3H), 4.82 (s, 2H), 1.70 (s, 6H).

Example 43

2-(2,6-Dichlorobenzyl)-N-phenyl[1,3]thiazolo[5,4-d]pyrimidin-7-amine

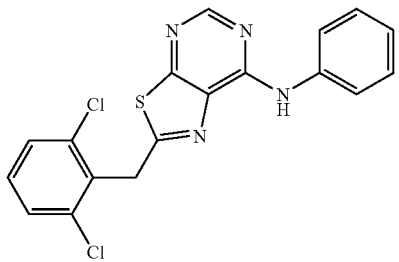

MS (ESI): mass calcd. for $C_{18}H_{12}Cl_2N_4S$, 386.0; m/z found, 387.0 $[M+H]^+$. $^1$H NMR ($(CD_3)_2SO$): 10.10 (s, 1H), 8.49 (s, 1H), 7.98-7.81 (m, 2H), 7.63 (d, J=8.0 Hz, 2H), 7.51-7.46 (m, 1H), 7.39-7.33 (m, 2H), 7.10 (t, J=7.4 Hz, 1H), 4.81 (s, 2H).

Example 44

2-(2,6-Dichlorobenzyl)-N-[4-(trifluoromethoxy)phenyl][1,3]thiazolo[5,4-d]pyrimidin-7-amine

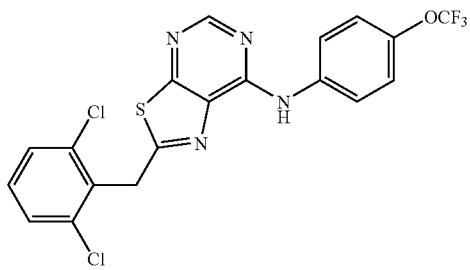

MS (ESI): mass calcd. for $C_{19}H_{11}Cl_2F_3N_4OS$, 470.0; m/z found, 471.0 $[M+H]^+$. $^1$H NMR ($(CD_3)_2SO$): 10.32 (s, 1H), 8.52 (s, 1H), 8.09-7.93 (m, 2H), 7.63 (d, J=8.0 Hz, 2H), 7.51-7.46 (m, 1H), 7.37 (d, J=8.5 Hz, 2H), 4.82 (s, 2H).

Example 45

2-(2,6-Dichlorobenzyl)-N-[3-fluoro-4-(methylsulfonyl)phenyl][1,3]thiazolo[5,4-d]pyrimidin-7-amine

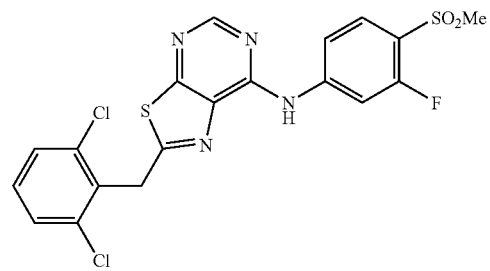

MS (ESI): mass calcd. for $C_{19}H_{13}Cl_2FN_4O_2S_2$, 482.0; m/z found, 483.0 $[M+H]^+$. $^1$H NMR ($(CD_3)_2SO$): 10.79 (s, 1H), 8.68 (s, 1H), 8.27 (dd, J=13.5, 1.9 Hz, 1H), 8.06 (dd, J=8.8, 2.0 Hz, 1H), 7.82 (t, J=8.6 Hz, 1H), 7.64 (d, J=8.0 Hz, 2H), 7.49 (dd, J=8.6, 7.6 Hz, 1H), 4.85 (s, 2H), 3.30 (s, 3H).

Example 46

2-(2,6-Dichlorobenzyl)-N-(4-methylphenyl)[1,3]thiazolo[5,4-d]pyrimidin-7-amine

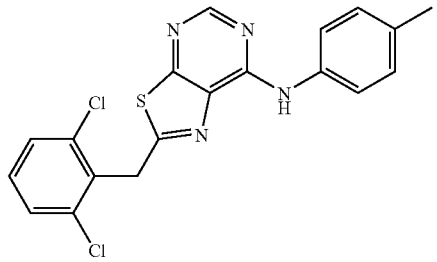

MS (ESI): mass calcd. for C$_{19}$H$_{14}$Cl$_2$N$_4$S, 400.0; m/z found, 401.0 [M+H]$^+$. $^1$H NMR ((CD$_3$)$_2$SO): 10.00 (s, 1H), 8.46 (s, 1H), 7.82-7.68 (m, 2H), 7.63 (d, J=8.1 Hz, 2H), 7.51-7.45 (m, 1H), 7.16 (d, J=8.3 Hz, 2H), 4.80 (s, 2H), 2.29 (s, 3H).

Example 47

2-(4-{[2-(2,6-Dichlorobenzyl)[1,3]thiazolo[5,4-d]pyrimidin-7-yl]amino}phenyl)-2-methylpropanamide

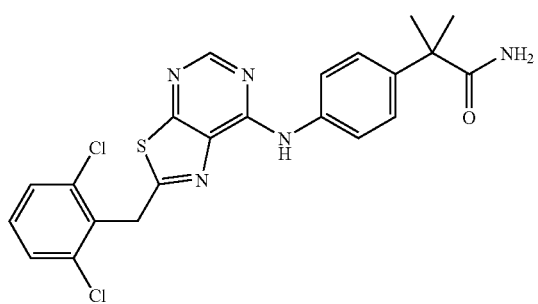

MS (ESI): mass calcd. for C$_{22}$H$_{19}$Cl$_2$N$_5$OS, 471.1; m/z found, 472.1 [M+H]$^+$. $^1$H NMR ((CD$_3$)$_2$SO): 10.08 (s, 1H), 8.45 (s, 1H), 7.84-7.73 (m, 2H), 7.63 (d, J=8.0 Hz, 2H), 7.48 (dd, J=8.6, 7.6 Hz, 1H), 7.35-7.28 (m, 2H), 6.88 (s, 2H), 4.81 (s, 2H), 1.50-1.36 (m, 6H).

Example 48

N-Phenyl-2-[2-(trifluoromethyl)benzyl][1,3]thiazolo[5,4-d]pyrimidin-7-amine

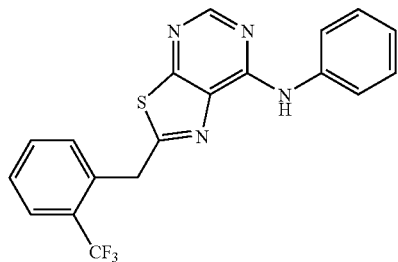

MS (ESI): mass calcd. for C$_{19}$H$_{13}$F$_3$N$_4$S, 386.1; m/z found, 387.1 [M+H]$^+$. $^1$H NMR ((CD$_3$)$_2$SO): 10.11 (s, 1H), 8.49 (s, 1H), 7.96-7.56 (m, 6H), 7.36 (t, J=7.9 Hz, 2H), 7.10 (t, J=7.3 Hz, 1H), 4.72 (s, 2H).

Example 49

N-(4-Bromophenyl)-2-[2-(trifluoromethyl)benzyl][1,3]thiazolo[5,4-d]pyrimidin-7-amine

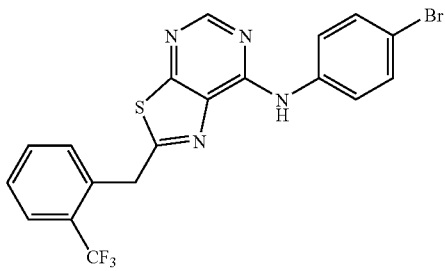

MS (ESI): mass calcd. for C$_{19}$H$_{12}$BrF$_3$N$_4$S, 464.0; m/z found, 465.0 [M+H]$^+$. $^1$H NMR ((CD$_3$)$_2$SO): 10.26 (s, 1H), 8.53 (s, 1H), 7.96-7.91 (m, 2H), 7.83 (d, J=7.9 Hz, 1H), 7.75 (t, J=7.2 Hz, 1H), 7.69 (d, J=7.6 Hz, 1H), 7.60 (t, J=7.6 Hz, 1H), 7.57-7.52 (m, 2H), 4.72 (s, 2H).

Example 50

N-(4-tert-Butylphenyl)-2-[2-(trifluoromethyl)benzyl][1,3]thiazolo[5,4-d]pyrimidin-7-amine

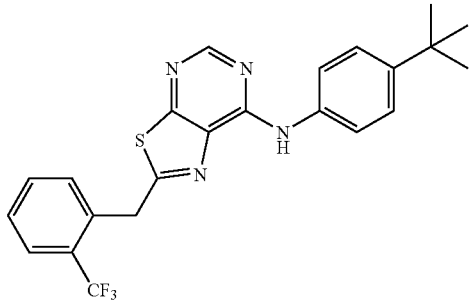

MS (ESI): mass calcd. for C$_{23}$H$_{21}$F$_3$N$_4$S, 442.1; m/z found, 443.2 [M+H]$^+$. $^1$H NMR ((CD$_3$)$_2$SO): 10.05 (s, 1H), 8.45 (s, 1H), 7.83 (d, J=7.9 Hz, 1H), 7.80-7.73 (m, 3H), 7.69 (d, J=7.9 Hz, 1H), 7.60 (t, J=7.6 Hz, 1H), 7.41-7.33 (m, 2H), 4.71 (s, 2H), 1.30 (s, 9H).

Example 51

N-[4-(Methylsulfonyl)phenyl]-2-[2-(trifluoromethyl)benzyl][1,3]thiazolo[5,4-d]pyrimidin-7-amine

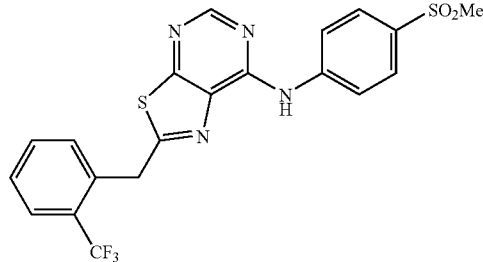

MS (ESI): mass calcd. for C$_{20}$H$_{15}$F$_3$N$_4$O$_2$S$_2$, 464.1; m/z found, 465.1 [M+H]$^+$. $^1$H NMR ((CD$_3$)$_2$SO): 10.59 (s, 1H), 8.62 (s, 1H), 8.31-8.19 (m, 2H), 7.92-7.88 (m, 2H), 7.84 (d, J=8.3 Hz, 1H), 7.76 (t, J=7.2 Hz, 1H), 7.71 (d, J=7.6 Hz, 1H), 7.61 (t, J=7.6 Hz, 1H), 4.75 (s, 2H), 3.20 (s, 3H).

Example 52

N-[4-(Morpholin-4-ylsulfonyl)phenyl]-2-[2-(trifluoromethyl)benzyl][1,3]thiazolo[5,4-d]pyrimidin-7-amine

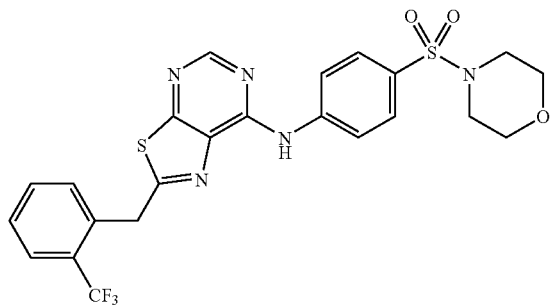

MS (ESI): mass calcd. for $C_{23}H_{20}F_3N_5O_3S_2$, 535.1; m/z found, 536.1 [M+H]$^+$. $^1$H NMR ((CD$_3$)$_2$SO): 10.57 (s, 1H), 8.62 (s, 1H), 8.35-8.22 (m, 2H), 7.84 (d, J=7.8 Hz, 1H), 7.78-7.68 (m, 4H), 7.61 (t, J=7.5 Hz, 1H), 4.75 (s, 2H), 3.66-3.62 (m, 4H), 2.95-2.82 (m, 4H).

Example 53

2-(3-Chlorobenzyl)-N-[6-(trifluoromethyl)pyridin-3-yl][1,3]thiazolo[5,4-d]pyrimidin-7-amine

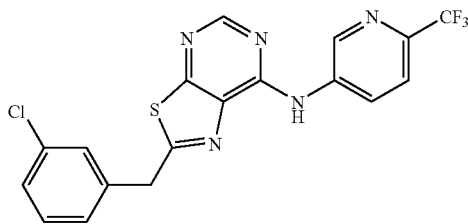

MS (ESI): mass calcd. for $C_{18}H_{11}ClF_3N_5S$, 421.0; m/z found, 422.1 [M+H]$^+$. $^1$H NMR ((CD$_3$)$_2$SO): 10.72 (s, 1H), 9.28 (d, J=2.1 Hz, 1H), 8.70 (dd, J=8.4, 2.4 Hz, 1H), 8.63 (s, 1H), 7.91 (d, J=8.7 Hz, 1H), 7.57-7.51 (m, 1H), 7.46-7.37 (m, 3 H), 4.60 (s, 2H).

Example 54

2-(3-Chlorobenzyl)-N-[4-(trifluoromethyl)phenyl][1,3]thiazolo[5,4-d]pyrimidin-7-amine

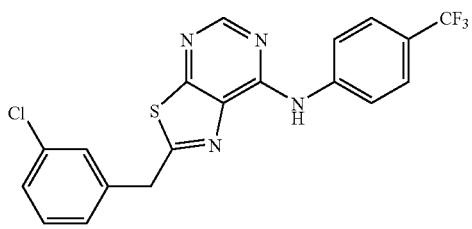

MS (ESI): mass calcd. for $C_{19}H_{12}ClF_3N_4S$, 420.0; m/z found, 421.1 [M+H]$^+$. $^1$H NMR ((CD$_3$)$_2$SO): 10.45 (s, 1H), 8.59 (s, 1H), 8.21 (d, J=8.5 Hz, 2H), 7.72 (d, J=8.6 Hz, 2H), 7.57-7.51 (m, 1H), 7.46-7.37 (m, 3H), 4.59 (s, 2H).

Example 55

2-(2,6-Dimethylbenzyl)-N-phenyl[1,3]thiazolo[5,4-d]pyrimidin-7-amine

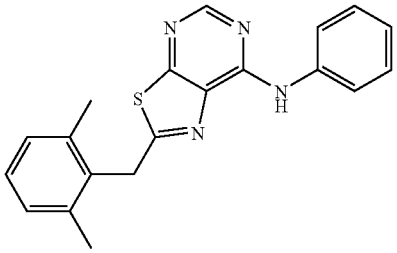

MS (ESI): mass calcd. for $C_{20}H_{18}N_4S$, 346.1; m/z found, 347.2 [M+H]$^+$. $^1$H NMR ((CD$_3$)$_2$SO): 10.02 (s, 1H), 8.46 (s, 1H), 7.97-7.85 (m, 2H), 7.45-7.29 (m, 2H), 7.22-7.06 (m, 4H), 4.51 (s, 2H), 2.33 (d, J=9.8 Hz, 6H).

Example 56

N-(4-Bromophenyl)-2-(2,6-dimethylbenzyl)[1,3]thiazolo[5,4-d]pyrimidin-7-amine

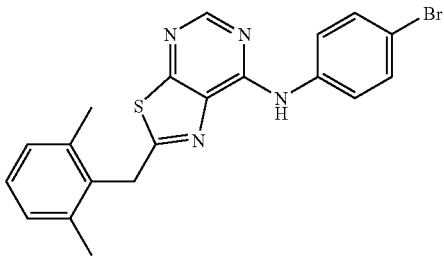

MS (ESI): mass calcd. for $C_{20}H_{17}BrN_4S$, 424.0; m/z found, 425.1 [M+H]$^+$. $^1$H NMR ((CD$_3$)$_2$SO): 10.19 (s, 1H), 8.49 (s, 1H), 8.00-7.90 (m, 2H), 7.59-7.47 (m, 2H), 7.22-7.08 (m, 3H), 4.52 (s, 2H), 2.34 (s, 6H).

Example 57

N-(4-tert-Butylphenyl)-2-(2,6-dimethylbenzyl)[1,3]thiazolo[5,4-d]pyrimidin-7-amine

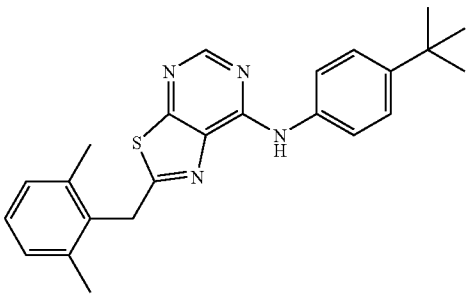

MS (ESI): mass calcd. for $C_{24}H_{26}N_4S$, 402.2; m/z found, 403.2 [M+H]$^+$. $^1$H NMR ((CD$_3$)$_2$SO): 9.97 (s, 1H), 8.42 (s, 1H), 7.83-7.71 (m, 2H), 7.43-7.33 (m, 2H), 7.22-7.08 (m, 3H), 4.51 (s, 2H), 2.34 (s, 6H), 1.30 (s, 9H).

Example 58

2-(2,6-Dimethylbenzyl)-N-[4-(trifluoromethyl)phenyl][1,3]thiazolo[5,4-d]pyrimidin-7-amine

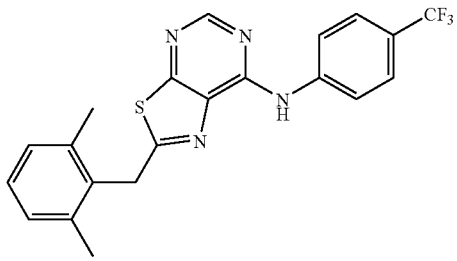

MS (ESI): mass calcd. for $C_{21}H_{17}F_3N_4S$, 414.1; m/z found, 415.1 [M+H]$^+$. $^1$H NMR ((CD$_3$)$_2$SO): 10.43 (s, 1H), 8.56 (s, 1H), 8.21 (d, J=8.6 Hz, 2H), 7.72 (d, J=8.7 Hz, 2H), 7.26-7.06 (m, 3H), 4.53 (s, 2H), 2.35 (s, 6H).

Example 59

2-(2,6-Dimethylbenzyl)-N-[6-(trifluoromethyl)pyridin-3-yl][1,3]thiazolo[5,4-d]pyrimidin-7-amine

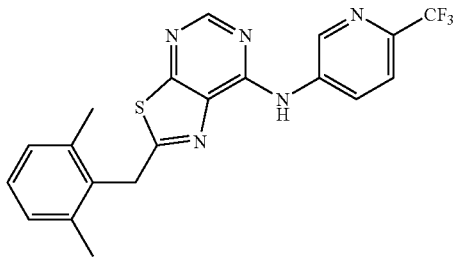

MS (ESI): mass-calcd. for $C_{20}H_{16}F_3N_5S$, 415.1; m/z found, 416.1 [M+H]$^+$. $^1$H NMR ((CD$_3$)$_2$SO): 10.71 (s, 1H), 9.29 (d, J=2.4 Hz, 1H), 8.70 (dd, J=8.6, 2.3 Hz, 1H), 8.60 (s, 1H), 7.91 (d, J=8.7 Hz, 1H), 7.26-7.06 (m, 3H), 4.55 (s, 2H), 2.35 (s, 6H).

Example 60

2-(2,6-Dimethylbenzyl)-N-[4-(morpholin-4-ylsulfonyl)phenyl][1,3]thiazolo[5,4-d]pyrimidin-7-amine

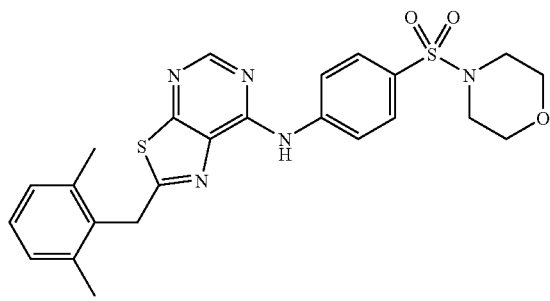

MS (ESI): mass calcd. for $C_{24}H_{25}N_5O_3S_2$, 495.1; m/z found, 496.2 [M+H]$^+$. $^1$H NMR ((CD$_3$)$_2$SO): 10.56 (s, 1H), 8.59 (s, 1H), 8.33-8.24 (m, 2H), 7.78-7.67 (m, 2H), 7.25-7.07 (m, 3H), 4.54 (s, 2H), 3.67-3.61 (m, 4H), 2.97-2.80 (m, 4H), 2.35 (s, 6).

Example 61

2-(2,6-Dimethylbenzyl)-N-[4-(methylsulfonyl)phenyl][1,3]thiazolo[5,4-d]pyrimidin-7-amine

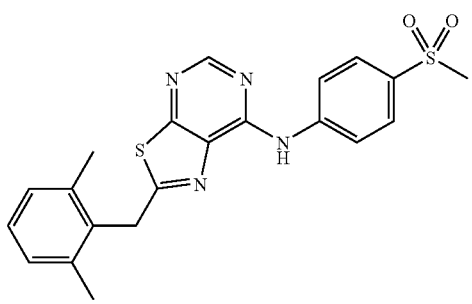

MS (ESI): mass calcd. for $C_{21}H_{20}N_4O_2S_2$, 424.1; m/z found, 425.1 [M+H]$^+$. $^1$H NMR ((CD$_3$)$_2$SO): 10.53 (s, 1H), 8.59 (s, 1H), 8.31-8.19 (m, 2H), 7.95-7.84 (m, 2H), 7.27-7.06 (m, 3H), 4.54 (s, 2H), 3.19 (s, 3H), 2.35 (s, 6H).

Example 62

[2-(2,6-Dichloro-benzyl)-5-methanesulfonyl-thiazolo[5,4-d]pyrimidin-7-yl]-(4-trifluoromethyl-phenyl)-amine

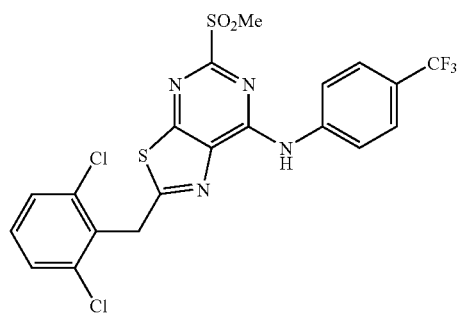

To a solution of [2-(2,6-dichloro-benzyl)-5-methylsulfanyl-thiazolo[5,4-d]pyrimidin-7-yl]-(4-trifluoromethyl-phenyl)-amine (110 mg, 0.22 mmol) in THF (6 mL) and MeOH (6 mL) was added a solution of potassium peroxymonosulfate (406 mg, 0.66 mmol) in H$_2$O (6 mL). The resulting mixture was stirred vigorously at 40° C. After 24 h, the mixture was concentrated and the crude residue was diluted with satd. aq. NaHCO$_3$ (10 mL) and extracted with EtOAc (10 mL×3). The combined organic layers were dried, concentrated, and purified by FCC to afford a colorless solid (100 mg, 85%). MS (ESI): mass calcd. for $C_{20}H_{13}Cl_2F_3N_4O_2S_2$, 531.9; m/z found, 532.9 [M+H]$^+$. $^1$H NMR ((CD$_3$)$_2$SO): 11.02 (s, 1H), 8.13 (d, J=8.6 Hz, 2H), 7.77 (d, J=8.7 Hz, 2H), 7.64 (d, J=8.1 Hz, 2H), 7.50 (dd, J=8.5, 7.8 Hz, 1H), 4.89 (s, 2H), 3.37 (s, 3H).

Example 63

[2-(2,6-Dichloro-benzyl)-5-morpholin-4-yl-thiazolo[5,4-d]pyrimidin-7-yl]-(4-trifluoromethyl-phenyl)-amine

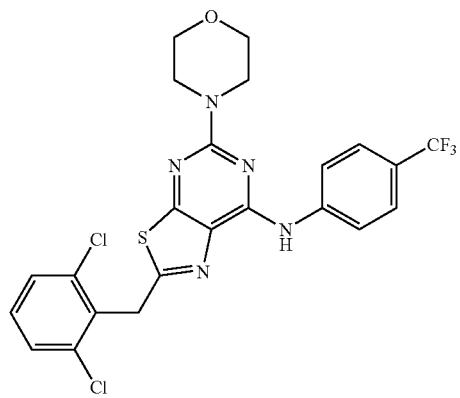

To a mixture of [2-(2,6-dichloro-benzyl)-5-methanesulfonyl-thiazolo[5,4-d]pyrimidin-7-yl]-(4-trifluoromethyl-phenyl)-amine (49 mg, 0.1 mmol) in tert-amyl alcohol (2 mL) was added morpholine (24 mg, 0.3 mmol). The resulting mixture was heated to 130° C. in a sealed tube. After 12 h, the solution was cooled and purified by preparative reverse-phase HPLC to afford the title compound as a colorless solid (37 mg, 77%). MS (ESI): mass calcd. for $C_{23}H_{18}Cl_2F_3N_5OS$, 539.0; m/z found, 540.0 [M+H]$^+$. $^1$H NMR ((CD$_3$)$_2$SO): 10.14 (s, 1H), 8.10 (d, J=8.5 Hz, 2H), 7.70 (d, J=8.6 Hz, 2H), 7.61 (d, J=8.1 Hz, 2H), 7.49-7.42 (m, 1H), 4.69 (s, 2H), 3.66 (s, 8H).

The compounds in Examples 64-88 were prepared using methods analogous to those described for Example 63.

Example 64

[2-(2,6-Dichloro-benzyl)-5-(2-methyl-pyrrolidin-1-yl)-thiazolo[5,4-d]pyrimidin-7-yl]-(4-trifluoromethyl-phenyl)-amine

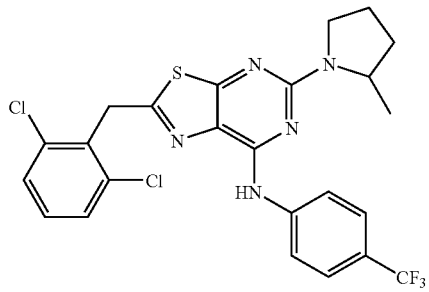

MS (ESI): mass calcd. for $C_{24}H_{20}Cl_2F_3N_5S$, 537.1; m/z found, 538.2 [M+H]$^+$. $^1$H NMR (CD$_3$OD): 8.04 (d, J=8.5 Hz, 2H), 7.71 (d, J=8.6 Hz, 2H), 7.53 (d, J=8.0 Hz, 2H), 7.42-7.37 (m, 1H), 4.82 (s, 2H), 4.47-4.31 (m, 2H), 3.83-3.48 (m, 2H), 2.32-2.01 (m, 2H), 1.89-1.79 (m, 1H), 1.31 (d, J=6.4 Hz, 3H).

Example 65

2-(2,6-Dichloro-benzyl)-N$^5$-(2-morpholin-4-yl-ethyl)-N$^7$-(4-trifluoromethyl-phenyl)-thiazolo[5,4-d]pyrimidine-5,7-diamine trifluoroacetic acid salt

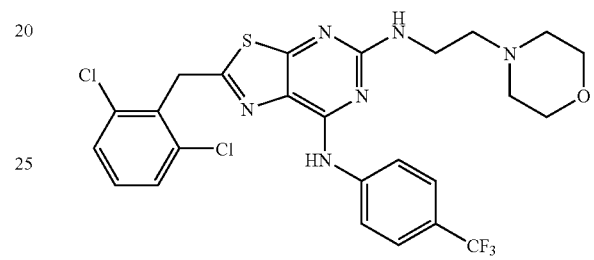

MS (ESI): mass calcd. for $C_{25}H_{23}Cl_2F_3N_6OS$, 582.1; m/z found, 583.1 [M+H]$^+$. $^1$H NMR ((CD$_3$)$_2$SO): 9.94 (s, 1H), 8.31-8.10 (m, 2H), 7.64 (d, J=8.4 Hz, 2H), 7.60 (d, J=8.1 Hz, 2H), 7.48-7.42 (m, 1H), 7.09-7.01 (m, 1H), 4.67 (s, 2H), 3.57-3.51 (m, 4H), 3.44-3.35 (m, 2H), 2.49-2.42 (m, 2H), 2.41-2.34 (m, 4H).

Example 66

N$^5$-Cyclopropylmethyl-2-(2,6-dichloro-benzyl)-N$^7$-(4-trifluoromethyl-phenyl)-thiazolo[5,4-d]pyrimidine-5,7-diamine

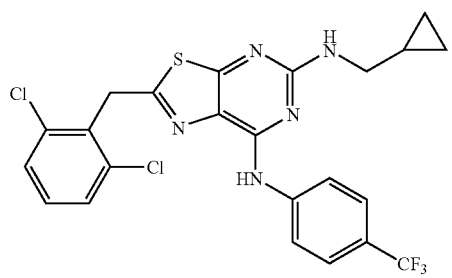

MS (ESI): mass calcd. for $C_{23}H_{18}Cl_2F_3N_5S$, 523.1; m/z found, 524.1 [M+H]$^+$. $^1$H NMR ((CD$_3$)$_2$SO): 9.90 (s, 1H), 8.35-8.13 (m, 2H), 7.64 (d, J=8.3 Hz, 2H), 7.60 (d, J=8.1 Hz, 2H), 7.48-7.42 (m, 1H), 7.30-7.24 (m, 1H), 4.67 (s, 2H), 3.21-3.12 (m, 2H), 1.11-1.02 (m, 1H), 0.46-0.35 (m, 2H), 0.24-0.18 (m, 2H).

Example 67

[2-(2,6-Dichloro-benzyl)-5-pyrrolidin-1-yl-thiazolo[5,4-d]pyrimidin-7-yl]-(4-trifluoromethyl-phenyl)-amine

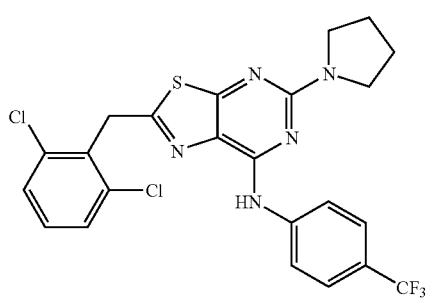

MS (ESI): mass calcd. for $C_{23}H_{18}Cl_2F_3N_5S$, 523.1; m/z found, 524.1 [M+H]$^+$. $^1$H NMR ((CD$_3$)$_2$SO): 9.95 (s, 1H), 8.25 (d, J=8.6 Hz, 2H), 7.67 (d, J=8.7 Hz, 2H), 7.60 (d, J=8.1 Hz, 2H), 7.48-7.43 (m, 1H), 4.67 (s, 2H), 3.61-3.43 (m, 4H), 2.02-1.84 (m, 4H).

Example 68

[2-(2,6-Dichloro-benzyl)-5-(2-isopropyl-pyrrolidin-1-yl)-thiazolo[5,4-d]pyrimidin-7-yl]-(4-trifluoromethyl-phenyl)-amine

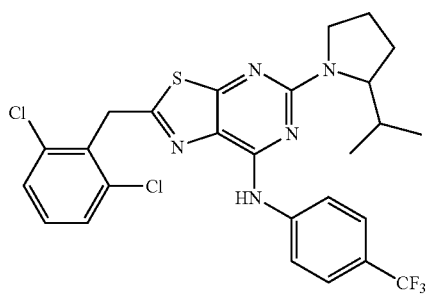

MS (ESI): mass calcd. for $C_{26}H_{24}Cl_2F_3N_5S$, 565.1; m/z found, 566.1 [M+H]$^+$. $^1$H NMR (CD$_3$OD): 8.03-7.94 (m, 2H), 7.69 (d, J=8.6 Hz, 2H), 7.52 (d, J=8.0 Hz, 2H), 7.42-7.36

(m, 1H), 4.81 (s, 2H), 4.35-4.09 (m, 1H), 3.83-3.52 (m, 2H), 2.52-2.29 (m, 1H), 2.20-1.87 (m, 4H), 0.92 (d, J=6.7 Hz, 3H), 0.85 (d, J=6.8 Hz, 3H).

Example 69

2-(2,6-Dichloro-benzyl)-N$^5$-isobutyl-N$^7$-(4-trifluoromethyl-phenyl)-thiazolo[5,4-d]pyrimidine-5,7-diamine

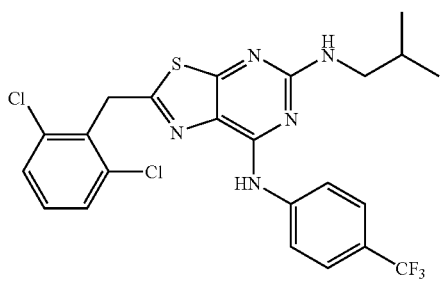

MS (ESI): mass calcd. for $C_{23}H_{20}Cl_2F_3N_5S$, 525.0; m/z found, 526.1 [M+H]$^+$. $^1$H NMR ((CD$_3$)$_2$SO): 10.10-9.85 (m, 1H), 8.40-8.10 (m, 2H), 7.64 (d, J=7.2 Hz, 2H), 7.61 (d, J=8.1 Hz, 2H), 7.48-7.43 (m, 1H), 6.86-6.85 (m, 1H), 4.66 (s, 2H), 3.12-3.04 (m, 2H), 1.94-1.80 (m, 1H), 0.89 (d, J=6.5 Hz, 6H).

Example 70

2-[2-(2,6-Dichloro-benzyl)-7-(4-trifluoromethyl-phenylamino)-thiazolo[5,4-d]pyrimidin-5-ylamino]-propan-1-ol

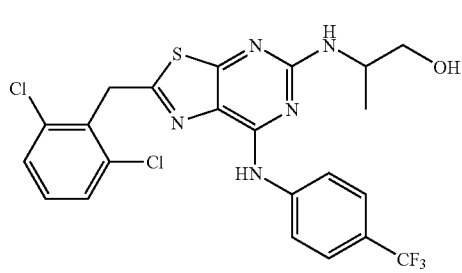

MS (ESI): mass calcd. for $C_{22}H_{18}Cl_2F_3N_5OS$, 527.0; m/z found, 528.1 [M+H]$^+$. $^1$H NMR ((CD$_3$)$_2$SO): 10.04 (s, 1H), 8.24 (d, J=8.0 Hz, 2H), 7.65 (d, J=8.6 Hz, 2H), 7.61 (d, J=8.0

Hz, 2H), 7.48-7.42 (m, 1H), 4.67 (s, 2H), 4.00-3.88 (m, 1 H), 3.53-3.44 (m, 1H), 3.37-3.29 (m, 1H), 1.13 (d, J=6.61 Hz, 3H).

Example 71

(S)-[2-(2,6-Dichloro-benzyl)-5-(2-methoxymethyl-Pyrrolidin-1-yl)-thiazolo[5,4-d]pyrimidin-7-yl]-(4-trifluoromethyl-phenyl)-amine

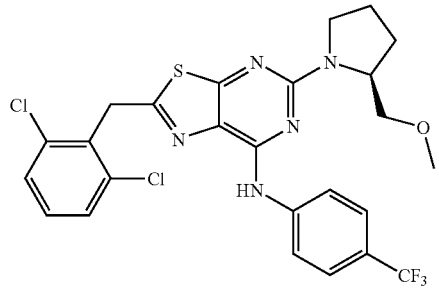

MS (ESI): mass calcd. for $C_{25}H_{22}Cl_2F_3N_5OS$, 567.0; m/z found, 568.1 [M+H]$^+$. $^1$H NMR ((CD$_3$)$_2$SO): 10.02 (s, 1H), 8.27-8.16 (m, 1H), 7.70-7.62 (m, 2H), 7.60 (d, J=8.1 Hz, 2H), 7.48-7.42 (m, 1H), 4.68 (s, 2H), 4.28-4.16 (m, 1H), 3.68-3.48 (m, 2H), 3.34-3.24 (m, 2H), 3.23 (s, 3H), 2.06-1.84 (m, 4H).

Example 72

2-(2,6-Dichloro-benzyl)-N$^5$-isopropyl-N$^7$-(4-trifluoromethyl-phenyl)-thiazolo[5,4-d]pyrimidine-5,7-diamine

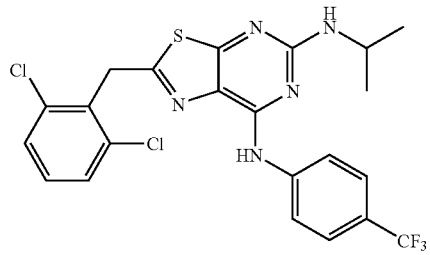

MS (ESI): mass calcd. for $C_{22}H_{18}Cl_2F_3N_5S$, 511.0; m/z found, 512.1 [M+H]$^+$. $^1$H NMR (CDCl$_3$): 9.36 (s, 1H), 8.49 (s, 1H), 7.93 (d, J=8.5 Hz, 2H), 7.73 (d, J=8.6 Hz, 2H), 7.43 (d, J=8.1 Hz, 2H), 7.33-7.28 (m, 1H), 4.73 (s, 2H), 4.26-4.17 (m, 1H), 1.37 (d, J=6.6 Hz, 6H).

Example 73

[5-Azetidin-1-yl-2-(2,6-dichloro-benzyl)-thiazolo[5,4-d]pyrimidin-7-yl]-(4-trifluoromethyl-phenyl)-amine

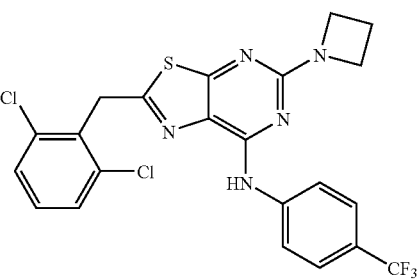

MS (ESI): mass calcd. for $C_{22}H_{16}Cl_2F_3N_5S$, 509.0; m/z found, 510.1 [M+H]$^+$. $^1$H NMR (CDCl$_3$): 8.20 (s, 1H), 7.93 (d, J=8.5 Hz, 2H), 7.64 (d, J=8.6 Hz, 2H), 7.41 (d, J=8.2 Hz, 2H), 7.30-7.24 (m, 1H), 4.69 (s, 2H), 4.35-4.29 (m, 4H), 2.51-2.40 (m, 2H).

Example 74

[2-(2,6-Dichloro-benzyl)-5-piperazin-1-yl-thiazolo[5,4-d]pyrimidin-7-yl]-(4-trifluoromethyl-phenyl)-amine trifluoroacetic acid salt

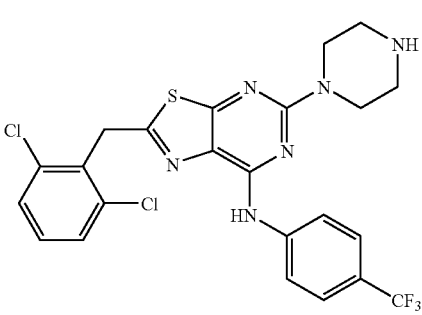

MS (ESI): mass calcd. for $C_{23}H_{19}Cl_2F_3N_6S$, 538.0; m/z found, 539.1 [M+H]$^+$. $^1$H NMR (CDCl$_3$): 9.58 (s, 1H), 7.99

(s, 1H), 7.79 (d, J=8.5 Hz, 2H), 7.65 (d, J=8.6 Hz, 2H), 7.42 (d, J=8.1 Hz, 2H), 7.30-7.25 (m, 1H), 4.71 (s, 2H), 4.20-4.11 (m, 4H), 3.33-3.24 (m, 4H).

Example 75

[2-(2,6-Dichloro-benzyl)-5-(4-isopropyl-piperazin-1-yl)-thiazolo[5,4-d]pyrimidin-7-yl]-(4-trifluoromethyl-phenyl)-amine trifluoroacetic acid salt

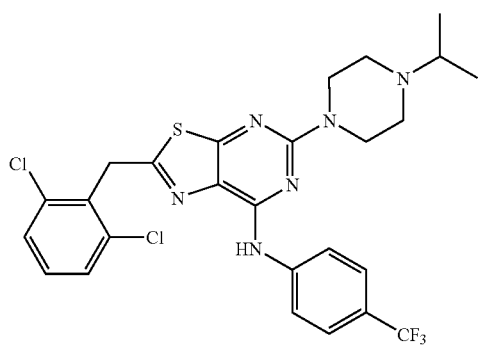

MS (ESI): mass calcd. for $C_{26}H_{25}Cl_2F_3N_6S$, 580.1; m/z found, 581.1 [M+H]$^+$. $^1$H NMR (CDCl$_3$): 7.96 (s, 1H), 7.79 (d, J=8.6 Hz, 2H), 7.65 (d, J=8.5 Hz, 2H), 7.42 (d, J=8.0 Hz, 2H), 7.29-7.24 (m, 1H), 4.89 (d, J=14.2 Hz, 2H), 4.70 (s, 2H), 3.68-3.48 (m, 5H), 2.97-2.74 (m, 2H), 1.39 (d, J=6.7 Hz, 6H).

Example 76

[5-(4-Cyclopentyl-piperazin-1-yl)-2-(2,6-dichloro-benzyl)-thiazolo[5,4-d]pyrimidin-7-yl]-(4-trifluoromethyl-phenyl)-amine trifluoroacetic acid salt

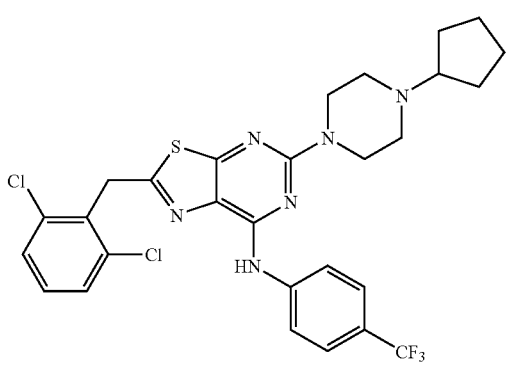

MS (ESI): mass calcd. for $C_{28}H_{27}Cl_2F_3N_6S$, 606.1; m/z found, 607.1 [M+H]$^+$. $^1$H NMR (CD$_3$OD): 7.95 (d, J=8.8 Hz, 2H), 7.67 (d, J=8.8 Hz, 2H), 7.52 (d, J=8.0 Hz, 2H), 7.42-7.35 (m, 1H), 4.95-4.85 (m, 2H), 4.78 (s, 2H), 3.77-3.63 (m, 2H), (m, 1H), 3.41-3.31 (m, 2H), 3.23-3.06 (m, 2H), 2.33-2.12 (m, 2H), 1.93-1.81 (m, 2H), 1.81-1.64 (m, 4H).

Example 77

[2-(2,6-Dichloro-benzyl)-5-(4-pyrrolidin-1-yl-piperidin-1-yl)-thiazolo[5,4-d]pyrimidin-7-yl]-(4-trifluoromethyl-phenyl)-amine trifluoroacetic acid salt

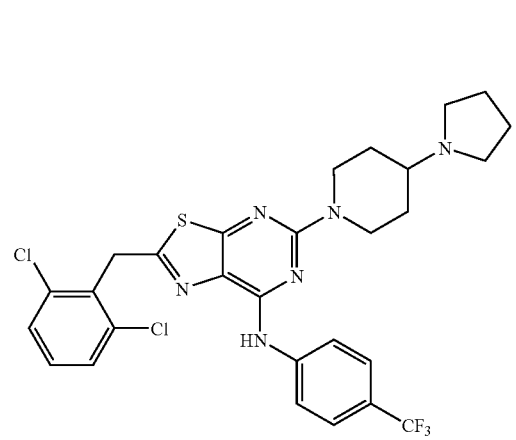

MS (ESI): mass calcd. for $C_{28}H_{27}Cl_2F_3N_6S$, 606.1; m/z found, 607.1 [M+H]$^+$. $^1$H NMR (CD$_3$OD): 7.97 (d, J=8.5 Hz, 2H), 7.65 (d, J=8.8 Hz, 2H), 7.52 (d, J=8.0 Hz, 2H), 7.41-7.35 (m, 1H), 4.94-4.85 (m, 2H), 4.76 (s, 2H), 3.70-3.62 (m, 2H), 3.51-3.39 (m, 1H), 3.25-3.12 (m, 2H), 3.07-2.97 (m, 2H), 2.33-2.20 (m, 2H), 2.20-2.12 (m, 2H), 2.06-1.92 (m, 2H), 1.72-1.55 (m, 2H).

Example 78

$N^5$-Cyclopropyl-2-(2,6-dichloro-benzyl)-$N^7$-(4-trifluoromethyl-phenyl)-thiazolo[5,4-d]pyrimidine-5,7-diamine

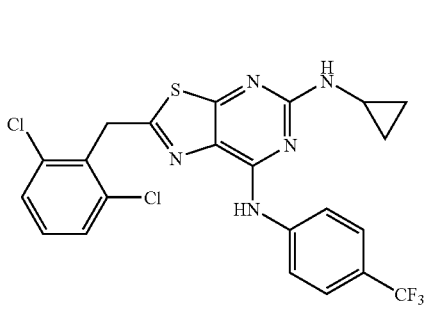

MS (ESI): mass calcd. for $C_{22}H_{16}Cl_2F_3N_5S$, 509.0; m/z found, 510.1 [M+H]$^+$. $^1$H NMR ((CD$_3$)$_2$SO): 10.00 (s, 1H), 8.47-8.23 (m, 2H), 7.65 (d, J=8.7 Hz, 2H), 7.60 (d, J=7.9 Hz, 2H), 7.48-7.42 (m, 1H), 4.68 (s, 2H), 2.76-2.64 (m, 1H), 0.79-0.63 (m, 2H), 0.53-0.45 (m, 2H).

Example 79

N⁵-Cyclobutyl-2-(2,6-dichloro-benzyl)-N⁷-(4-trifluoromethyl-phenyl)-thiazolo[5,4-d]pyrimidine-5,7-diamine

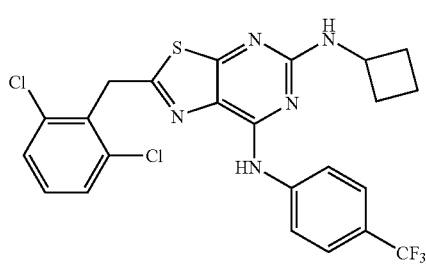

MS (ESI): mass calcd. for $C_{23}H_{18}Cl_2F_3N_5S$, 523.0, m/z found, 524.1 [M+H]⁺. ¹H NMR ((CD₃)₂SO): 9.95 (s, 1H), 8.23 (d, J=8.6 Hz, 2H), 7.66 (d, J=8.1 Hz, 2H), 7.60 (d, J=8.0 Hz, 2H), 7.48-7.41 (m, 1H), 4.67 (s, 2H), 4.38-4.24 (m, 1H), 2.32-2.18 (m, 2H), 2.05-1.88 (m, 2H), 1.76-1.59 (m, 2H).

Example 80

2-(2,6-Dichloro-benzyl)-N⁵,N⁵-diisobutyl-N⁷-(4-trifluoromethyl-phenyl)-thiazolo[5,4-d]pyrimidine-5,7-diamine

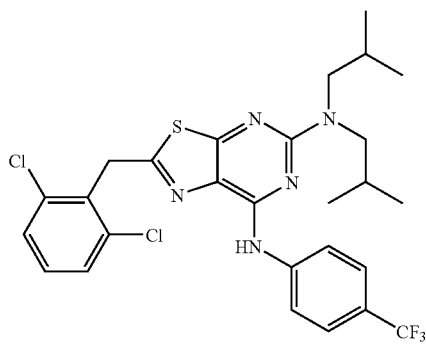

MS (ESI): mass calcd. for $C_{27}H_{28}Cl_2F_3N_5S$, 581.1, m/z found, 582.1 [M+H]⁺. ¹H NMR (CDCl₃): 8.00 (s, 1H), 7.92 (d, J=8.5 Hz, 2H), 7.62 (d, J=8.6 Hz, 2H), 7.41 (d, J=8.1 Hz, 2H), 7.29-7.22 (m, 1H), 4.68 (s, 2H), 3.48 (d, J=7.5 Hz, 4H), 2.29-2.15 (m, 2H), 0.94 (d, J=6.6 Hz, 12H).

Example 81

[2-(2,6-Dichloro-benzyl)-5-piperidin-1-yl-thiazolo[5,4-d]pyrimidin-7-yl]-(4-trifluoromethyl-phenyl)-amine

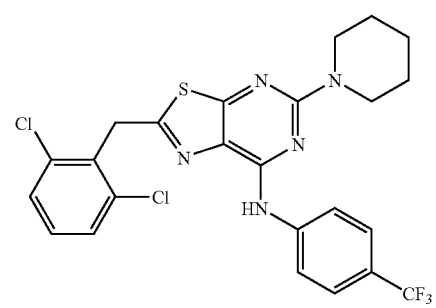

MS (ESI): mass calcd. for $C_{24}H_{20}Cl_2F_3N_5S$, 537.0; m/z found, 538.1 [M+H]⁺. ¹H NMR ((CD₃)₂SO): 10.04 (s, 1H), 8.09 (d, J=8.6 Hz, 2H), 7.69 (d, J=8.7 Hz, 2H), 7.60 (d, J=8.1 Hz, 2H), 7.48-7.42 (m, 1H), 4.67 (s, 2H), 3.75-3.68 (m, 4H), 1.68-1.57 (m, 2H), 1.56-1.48 (m, 4H).

Example 82

2-(2,6-Dichloro-benzyl)-N⁵-(2-pyrrolidin-1-yl-ethyl)-N⁷-(4-trifluoromethyl-phenyl)-thiazolo[5,4-d]pyrimidine-5,7-diamine trifluoroacetic acid salt

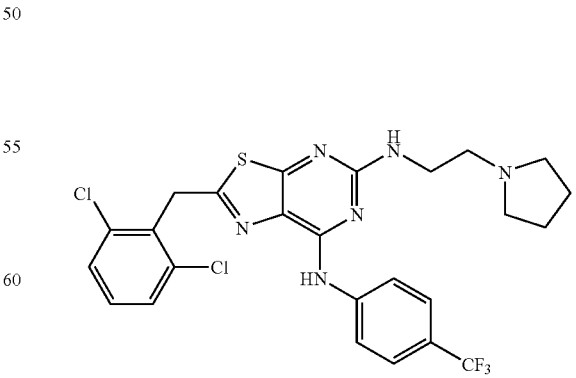

MS (ESI): mass calcd. for $C_{25}H_{23}Cl_2F_3N_6S$, 566.1; m/z found, 567.1 [M+H]⁺. ¹H NMR (CDCl₃): 7.86 (d, J=8.2 Hz, 2H), 7.73-7.59 (m, 2H), 7.41 (d, J=8.1 Hz, 1(, 7.30-7.25 (m, 1H), 4.69 (s, 2H), 3.98-3.75 (m, 4H), 3.45-3.33 (m, 2H), 2.84 (s, 2H), 2.24-1.89 (m, 4H).

Example 83

[2-(2,6-Dichloro-benzyl)-5-(4-isobutyl-piperazin-1-yl)-thiazolo[5,4-d]pyrimidin-7-yl]-(4-trifluoromethyl-phenyl)-amine trifluoroacetic acid salt

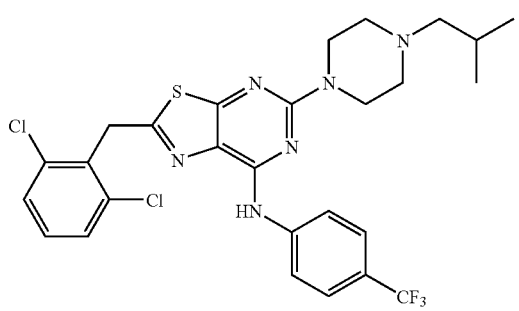

MS (ESI): mass calcd. for $C_{27}H_{27}Cl_2F_3N_6S$, 594.1; m/z found, 595.1 [M+H]$^+$. $^1$H NMR ((CD$_3$)$_2$SO): 10.24 (s, 1H), 8.07 (d, J=8.5 Hz, 2H), 7.71 (d, J=8.7 Hz, 2 H), 7.61 (d, J=8.1 Hz, 2H), 7.49-7.43 (m, 1H), 4.71 (s, 2H), 4.57 (d, J=13.2 Hz, 2H), 3.63-3.49 (m, 2H), 3.47-3.34 (m, 2H), 3.15-3.00 (m, 2H), 3.00-2.93 (m, 2H), 2.19-2.00 (m, 1H), 0.97 (d, J=6.5 Hz, 6H).

Example 84

2-(2,6-Dichloro-benzyl)-N$^5$-pyridin-2-ylmethyl-N$^7$-(4-trifluoromethyl-phenyl)-thiazolo[5,4-d]pyrimidine-5,7-diamine trifluoroacetic acid salt

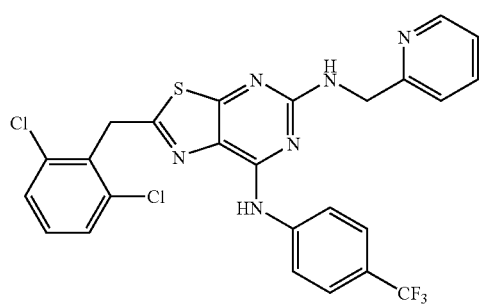

MS (ESI): mass calcd. for $C_{25}H_{17}Cl_2F_3N_6S$, 560.0; m/z found, 561.1 [M+H]$^+$. $^1$H NMR ((CD$_3$)$_2$SO): 10.08 (s, 1H), 8.69-8.62 (m, 1H), 8.43-8.02 (m, 2H), 8.02-7.73 (m, 2H), 7.73-7.63 (m, 1H), 7.64-7.53 (m, 3H), 7.48-7.43 (m, 2H), 4.75-4.69 (m, 2H), 4.68 (s, 2H).

Example 85

2-(2,6-Dichloro-benzyl)-N$^5$-pyridin-3-ylmethyl-N$^7$-(4-trifluoromethyl-phenyl)-thiazolo[5,4-d]pyrimidine-5,7-diamine trifluoroacetic acid salt MS (ESI): mass calcd. for $C_{25}H_{17}Cl_2F_3N_6S$, 560.0; m/z found, 561.1 [M+H]$^+$. $^1$H NMR (CDCl$_3$): 11.53 (s, 1H), 8.80 (s, 1H), 8.69 (d, J=5.0 Hz, 1H), 8.50 (s, 1 H), 8.22 (d, J=6.3 Hz, 1H), 7.80-7.54 (m, 4H), 7.42 (d, J=8.0 Hz, 2H), 7.32-7.26 (m, 1H), 4.84-4.77 (m, 2H), 4.71 (s, 2H).

Example 86

2-(2,6-Dichloro-benzyl)-N$^5$-pyridin-4-ylmethyl-N$^7$-(4-trifluoromethyl-phenyl)-thiazolo[5,4-d]pyrimidine-5,7-diamine trifluoroacetic acid salt

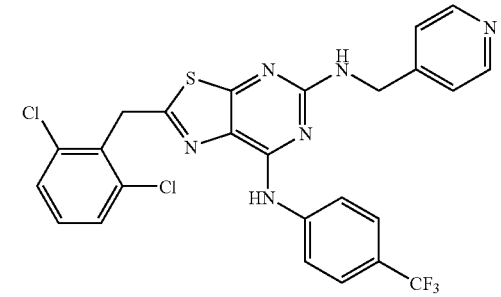

MS (ESI): mass calcd. for $C_{25}H_{17}Cl_2F_3N_6S$, 560.0; m/z found, 561.1 [M+H]$^+$. $^1$H NMR (CDCl$_3$): 8.73 (d, J=6.2 Hz, 2H), 8.39-8.04 (m, 1H), 7.80-7.54 (m, 5H), 7.43 (d, J=8.0 Hz, 2H), 7.34-7.27 (m, 1H), 4.84 (d, J=5.5 Hz, 2H), 4.72 (s, 2H).

Example 87

2-(2,6-Dichlorobenzyl)-N$^5$-(1-pyridin-2-ylethyl)-N$^7$-[4-(trifluoromethyl)phenyl][1,3]thiazolo[5,4-d]pyrimidine-5,7-diamine

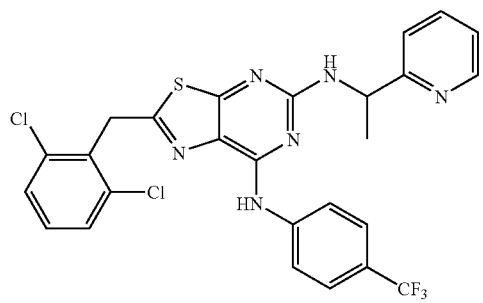

MS (ESI): mass calcd. for $C_{26}H_{19}Cl_2F_3N_6S$, 574.1; m/z found, 575.1 [M+H]$^+$. $^1$H NMR ((CD$_3$)$_2$SO): 9.97 (s, 1H), 8.62 (d, J=4.4 Hz, 1H), 8.12-7.90 (m, 2H), 7.87-7.79 (m, 2H), 7.70-7.54 (m, 5H), 7.51-7.41 (m, 2H), 5.16-5.11 (m, 1H), 4.66 (s, 2H), 1.52 (d, J=7.0 Hz, 3H).

Example. 88

2-(2,6-Dichlorobenzyl)-N$^5$-[(1-ethylpyrrolidin-2-yl)methyl]-N$^7$-[4-(trifluoromethyl)phenyl][1,3]thiazolo[5,4-d]pyrimidine-5,7-diamine

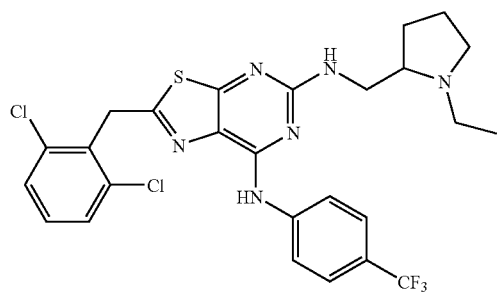

MS (ESI): mass calcd. for $C_{26}H_{25}Cl_2F_3N_6S$, 580.1; m/z found, 581.1 [M+H]$^+$. $^1$H NMR ((CD$_3$)$_2$SO): 10.16 (s, 1H), 9.01 (s, 1H), 8.28-8.05 (m, 2H), 7.71-7.64 (m, 1H), 7.61 (d, J=8.0 Hz, 2H), 7.50-7.43 (m, 2H), 4.69 (s, 2H), 3.98-3.32 (m, 5 H), 3.17-2.90 (m, 2H), 2.24-1.72 (m, 4H), 1.29-1.03 (m, 3H).

Example 89

2-(2,6-Dichlorobenzyl)-N$^5$-[(3R)-pyrrolidin-3-ylmethyl]-N$^7$-[4-(trifluoromethyl)phenyl][1,3]thiazolo[5,4-d]pyrimidine-5,7-diamine hydrochloride salt

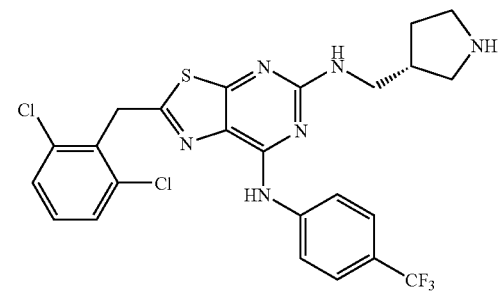

Step A. 3-{[2-(2,6-Dichloro-benzyl)-7-(4-trifluoromethyl-phenylamino)-thiazolo[5,4-d]pyrimidin-5-ylamino]-methyl}-pyrrolidine-1-carboxylic acid tert-butyl ester The title compound was prepared using methods analogous to those described for Example 63. MS (ESI): mass calcd. for $C_{29}H_{29}Cl_2F_3N_6O_2S$, 652.1; m/z found, 653.1 [M+H]$^+$.

Step B

A solution of HCl (4 N in dioxane; 2 mL) and 3-{[2-(2,6-dichloro-benzyl)-7-(4-trifluoromethyl-phenylamino)-thiazolo[5,4-d]pyrimidin-5-ylamino]-methyl}-pyrrolidine-1-carboxylic acid tert-butyl ester (50 mg, 0.08 mmol) was stirred at rt for 6 h. The mixture was filtered and the resulting solid was washed with Et$_2$O (10 mL) to provided the title compound as yellow solid (19 mg, 43%). MS (ESI): mass calcd. for $C_{24}H_{21}Cl_2F_3N_6S$, 552.1; m/z found, 553.1 [M+H]$^+$. $^1$H NMR ((CD$_3$)$_2$SO): 9.98 (s, 1H), 8.89 (s, 1H), 8.21 (d, J=8.6 Hz, 2H), 7.77-7.32 (m, 5H), 5.87-5.78 (m, 1 H), 4.67 (s, 2H), 4.17-3.93 (m, 4H), 3.77-3.63 (m, 2H), 2.96-2.84 (m, 1H), 2.05-1.95 (m, 1H), 1.73-1.59 (m, 1H).

The compounds in Examples 90-92 were prepared using methods analogous to those described for Example 89.

Example 90

2-(2,6-Dichlorobenzyl)-$N^5$-(piperidin-2-ylmethyl)-$N^7$-[4-(trifluoromethyl)phenyl][1,3]thiazolo[5,4-d]pyrimidine-5,7-diamine hydrochloride salt

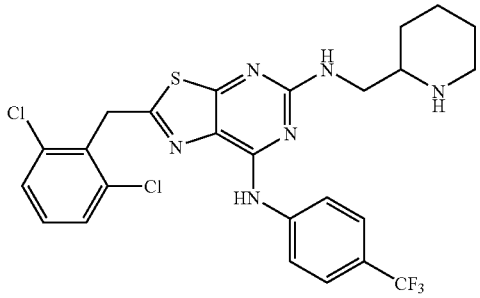

Step A. 2-{[2-(2,6-Dichloro-benzyl)-7-(4-trifluoromethyl-phenylamino)-thiazolo[5,4-d]pyrimidin-5-ylamino]-methyl}-piperidine-1-carboxylic acid tert-butyl ester MS (ESI): mass calcd. for $C_{30}H_{31}Cl_2F_3N_6O_2S$, 666.1; m/z found, 667.1 [M+H]$^+$.

Step B

MS (ESI): mass calcd. for $C_{25}H_{23}Cl_2F_3N_6S$, 566.1; m/z found, 567.1 [M+H]$^+$. $^1$H NMR ((CD$_3$)$_2$SO): 10.04 (m, 1H), 8.80-8.52 (m, 2H), 8.23-8.18 (m, 2H), 7.75-7.56 (m, 3H), 7.50-7.37 (m, 2H), 4.69 (s, 2H), 3.53-3.44 (m, 2H), 3.29-3.14 (m, 2H), 2.90-2.73 (m, 1H), 1.96-1.29 (m, 6H).

Example 91

2-(2,6-Dichlorobenzyl)-$N^5$-(piperidin-3-ylmethyl)-$N^7$-[4-(trifluoromethyl)phenyl][1,3]thiazolo[5,4-d]pyrimidine-5,7-diamine hydrochloride salt

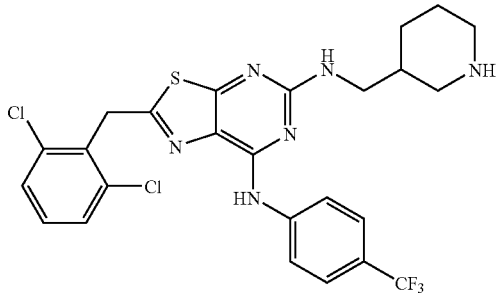

Step A. 3-{[2-(2,6-Dichloro-benzyl)-7-(4-trifluoromethyl-phenylamino)-thiazolo[5,4-d]pyrimidin-5-ylamino]-methyl}-piperidine-1-carboxylic acid tert-butyl ester MS (ESI): mass calcd. for $C_{30}H_{31}Cl_2F_3N_6O_2S$, 666.1; m/z found, 667.1 [M+H]$^+$.

Step B

MS (ESI): mass calcd. for $C_{25}H_{23}Cl_2F_3N_6S$, 566.1; m/z found, 567.1 [M+H]$^+$. $^1$H NMR ((CD$_3$)$_2$SO): 9.96 (m, 1H), 8.71-8.62 (m, 1H), 8.45-8.31 (m, 1H), 8.25-8.15 (m, 2H), 7.75-7.55 (m, 3H), 7.49-7.37 (m, 2H), 4.67 (s, 2H), 3.35-3.09 (m, 4H), 2.83-2.55 (m, 2H), 2.20-1.96 (m, 1H), 1.85-1.71 (m, 2H), 1.66-1.48 (m, 1H), 1.31-1.12 (m, 1H).

Example 92

2-(2,6-Dichlorobenzyl)-$N^5$-(Piperidin-4-ylmethyl)-$N^7$-[4-(trifluoromethyl)phenyl][1,3]thiazolo[5,4-d]pyrimidine-5,7-diamine hydrochloride salt

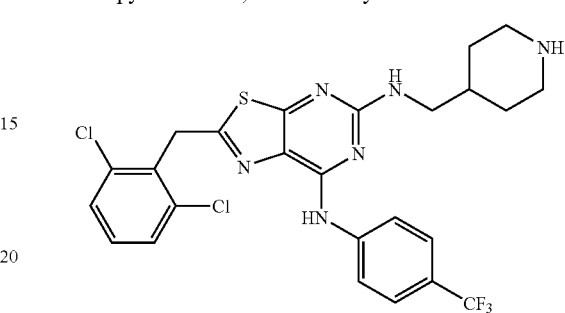

Step A. 4-{[2-(2,6-Dichloro-benzyl)-7-(4-trifluoromethyl-phenylamino)-thiazolo[5,4-d]pyrimidin-5-ylamino]-methyl}-piperidine-1-carboxylic acid tert-butyl ester MS (ESI): mass calcd. for $C_{30}H_{31}Cl_2F_3N_6O_2S$, 666.1; m/z found, 667.1 [M+H]$^+$.

Step B

MS (ESI): mass calcd. for $C_{25}H_{23}Cl_2F_3N_6S$, 566.1; m/z found, 567.1 [M+H]$^+$. $^1$H NMR ((CD$_3$)$_2$SO): 9.96 (m, 1H), 8.67-8.36 (m, 1H), 8.32-8.07 (m, 2H), 7.74-7.53 (m, 3H), 7.49-7.30 (m, 2H), 4.67 (s, 2H), 3.29-3.16 (m, 3H), 2.90-2.73 (m, 2H), 2.47-2.40 (m, 2H), 2.35-2.30 (m, 3H), 1.92-1.71 (m, 2H).

Example 93

[2-(2,6-Dichloro-benzyl)-thiazolo[5,4-d]pyrimidin-7-yl]-(5-trifluoromethyl-pyrazin-2-yl)-amine

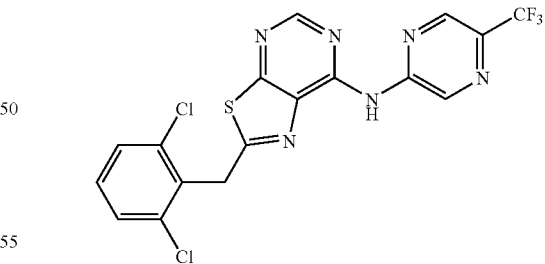

To a mixture of 7-chloro-2-(2,6-dichloro-benzyl)-thiazolo[5,4-d]pyrimidine (113 mg, 0.34 mmol), 1,2,3,4,5-pentaphenyl-1-(di-t-butylphosphino)ferrocene (49 mg, 0.07 mmol), tris(dibenzylideneacetone)dipalladium (0) (31 mg, 0.03 mmol), and 5-trifluoromethyl-pyrazin-2-ylamine (66 mg, 0.41 mmol) in toluene (3 mL) was added NaOtBu (40 mg, 0.41 mmol) at rt. The mixture was heated to 90° C. under N$_2$. After 18 h, the reaction mixture was cooled and filtered through a pad of diatomaceous earth, eluting with MeOH (30 mL). The filtrate was concentrated and the crude residue was purified using preparative reverse-phase HPLC to afford the title compound a colorless solid (43 mg, 28%). MS (ESI): mass calcd. for $C_{17}H_9Cl_2F_3N_6S$, 455.9; m/z found, 457.0 [M+H]$^+$. $^1$H NMR ((CD$_3$)$_2$SO): 10.77 (s, 1H), 9.49 (s, 1H), 8.88-8.87 (m, 1H), 8.75 (s, 1H), 7.59 (d, J=8.0 Hz, 2H), 7.45 (dd, J=8.5, 7.7 Hz, 1H), 4.83 (s, 2H).

Example 94

[2-(2,6-Dichloro-benzyl)-thiazolo[5,4-d]pyrimidin-7-yl]-(5-trifluoromethyl-pyridin-2-yl)-amine

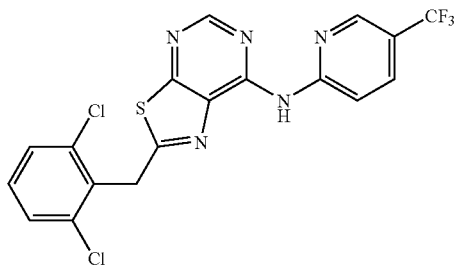

To a mixture of 7-chloro-2-(2,6-dichloro-benzyl)-thiazolo[5,4-d]pyrimidine (120 mg, 0.36 mmol), 2-(dicyclohexylphosphino)biphenyl (25 mg, 0.07 mmol), palladium acetate (8.0 mg, 0.04 mmol), and 5-trifluoromethyl-pyridin-2-ylamine (88 mg, 0.54 mmol) in toluene (3 mL) was added NaOtBu (49 mg, 0.51 mmol) at rt. The mixture was heated to 90° C. for 18 h under N$_2$. The reaction mixture was cooled and filtered through a pad of diatomaceous earth, eluting with EtOAc (30 mL). The filtrate was concentrated and the crude residue was purified using preparative reverse-phase HPLC to afford the title compound a colorless solid (95 mg, 58%). MS (ESI): mass calcd. for $C_{18}H_{10}Cl_2F_3N_5S$, 455.0; m/z found, 456.0 [M+H]$^+$. $^1$H NMR ((CD$_3$)$_2$SO): 9.76 (s, 1H), 8.73-8.71 (m, 2H), 8.50 (d, J=8.8 Hz, 1H), 8.23 (dd, J=8.9, 2.4 Hz, 1H), 7.60 (d, J=8.1 Hz, 2H), 7.45 (dd, J=8.5, 7.7 Hz, 1H), 4.83 (s, 2H).

The compounds in Examples 95-97 were prepared using methods analogous to those described for Example 94.

Example 95

2-[2-(Trifluoromethyl)benzyl]-N-[5-(trifluoromethyl)pyridin-2-yl][1,3]thiazolo[5,4-d]pyrimidin-7-amine

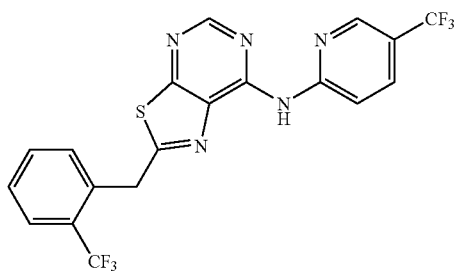

MS (ESI): mass calcd. for $C_{19}H_{11}F_6N_5S$, 455.1; m/z found, 456.1 [M+H]$^+$. $^1$H NMR ((CD$_3$)$_2$SO): 8.95-8.79 (m, 2H), 8.71 (s, 1H), 8.61 (s, 1H), 8.02-7.96 (m, 1H), 7.80-7.70 (m, 1H), 7.63-7.42 (m, 3H), 4.63 (s, 2H).

Example 96

[2-(2-Chloro-benzyl)-thiazolo[5,4-d]pyrimidin-7-yl]-(5-trifluoromethyl-pyridin-2-yl)-amine

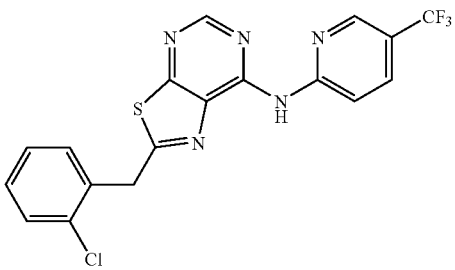

MS (ESI): mass calcd. for $C_{18}H_{11}ClF_3N_5S$, 421.0; m/z found, 422.1 [M+H]$^+$. $^1$H NMR ((CD$_3$)$_2$SO): 9.85 (s, 1H), 8.74-8.72 (m, 1H), 8.72 (s, 1H), 8.54 (d, J=8.9 Hz, 1H), 8.26-8.22 (m, 1H), 7.64-7.59 (m, 1H), 7.56-7.52 (m, 1H), 7.42-7.38 (m, 2H), 4.67 (s, 2H).

Example 97

[2-(2,6-Dichloro-benzyl)-5-methyl-thiazolo[5,4-d]pyrimidin-7-yl]-(5-trifluoromethyl-pyridin-2-yl)-amine

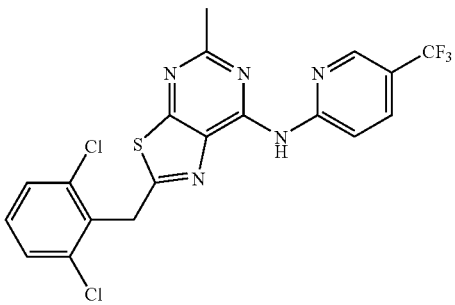

MS (ESI): mass calcd. for $C_{19}H_{12}Cl_2F_3N_5S$, 469.0; m/z found, 470.0 [M+H]$^+$. $^1$H NMR ((CD$_3$)$_2$SO): 9.55 (s, 1H), 8.70-8.69 (m, 1H), 8.55 (d, J=8.8 Hz, 1H), 8.22 (dd, J=8.9, 2.3 Hz, 1H), 7.59 (d, J=8.0 Hz, 2H), 7.44 (dd, J=8.5, 7.7 Hz, 1H), 4.79 (s, 2H), 2.63 (s, 3H).

Example 98

2-(2,6-Dichlorobenzyl)-N-[5-(trifluoromethyl)-1,3,4-thiadiazol-2-yl][1,3]thiazolo[5,4-d]pyrimidin-7-amine

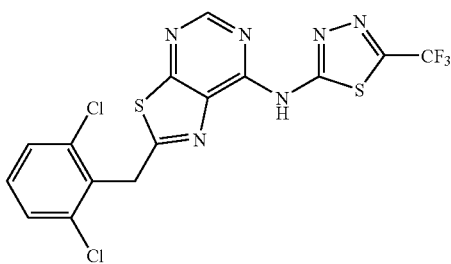

To a solution of 7-chloro-2-(2,6-dichloro-benzyl)-thiazolo[5,4-d]pyrimidine (83 mg, 0.3 mmol) and 5-trifluoromethyl-

[1,3,4]thiadiazol-2-ylamine (63 mg, 0.4 mmol) in DMF (1 mL) was added NaH (60% dispersion in oil; 20 mg, 0.5 mmol) at rt. After 12 h, the reaction mixture was poured into H$_2$O (5 mL) and the resulting solid was collected by vacuum filtration and washed with 1:1 (IPA-H$_2$O) to afford the title compound as a yellow solid (48 mg, 41%). MS (ESI): mass calcd. for C$_{15}$H$_7$Cl$_2$F$_3$N$_6$S$_2$, 462.0; m/z found, 462.9 [M+H]$^+$. $^1$H NMR ((CD$_3$)$_2$SO): 8.45 (s, 1H), 7.58 (d, J=8.0 Hz, 2H), 7.46-7.41 (m, 1H), 4.72 (s, 2H).

Example 99

N-(5-tert-Butyl-1,3,4-thiadiazol-2-yl)-2-(2,6-dichlorobenzyl)[1,3]thiazolo[5,4-d]pyrimidin-7-amine

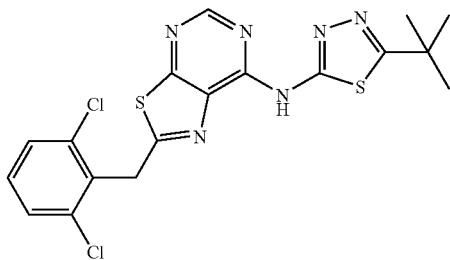

The title compound was prepared using methods analogous to those described for Example 98. MS (ESI): mass calcd. for C$_{18}$H$_{16}$Cl$_2$N$_6$S$_2$, 450.0; m/z found, 451.1 [M+H]$^+$. $^1$H NMR ((CD$_3$)$_2$SO): 8.75 (s, 1H), 7.61 (d, J=8.1 Hz, 2H), 7.49-7.44 (m, 1H), 4.81 (s, 2H), 1.42 (s, 9H).

Example 100

2-[7-(4-Trifluoromethyl-phenylamino)-thiazolo[5,4-d]pyrimidin-2-ylmethyl]-benzonitrile

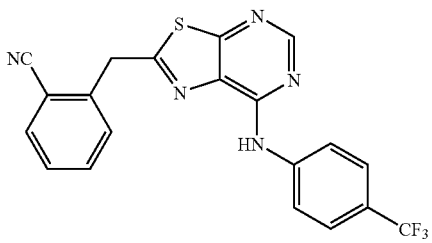

To a solution of [2-(2-iodo-benzyl)-thiazolo[5,4-d]pyrimidin-7-yl]-(4-trifluoromethyl-phenyl)-amine (0.20 g, 0.39 mmol) in anhydrous DMF (3.9 mL) was added copper cyanide (0.24, 2.73 mmol). The resulting suspension was heated to 100° C. in a sealed tube for 5 h. The reaction mixture was cooled to rt, diluted with H$_2$O (20 mL) and extracted with EtOAc (2×10 mL). The organic layers were combined, washed with 10% aq. HCl (2×5 mL) and satd. aq. NaCl (2×5 mL), dried, filtered, concentrated and purified by FCC to provide the title compound as a colorless solid (0.15 g, 94%). MS (ESI): mass calcd. for C$_{20}$H$_{12}$F$_3$N$_5$S, 411.1; m/z found 412.1 [M+H]$^+$. $^1$H NMR (CDCl$_3$): 8.63 (s, 1H), 8.18 (s, 1H), 7.97 (d, J=8.5 Hz, 2H), 7.75-7.72 (d, J=8.5 Hz, 2H), 7.65-7.61 (m, 1H), 7.52-7.49 (m, 1H), 7.48-7.44 (m, 2H), 4.66 (s, 2H).

Example 101

[2-(2,6-Dichloro-benzyl)-5-methoxy-thiazolo[5,4-d]pyrimidin-7-yl]-(4-trifluoromethyl-phenyl)-amine

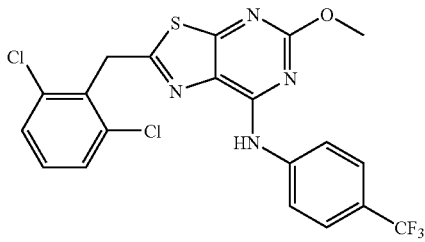

To solution of NaOMe (15 mg, 0.3 mmol) and MeOH (1.5 mL) was added [2-(2,6-dichloro-benzyl)-5-methanesulfonyl-thiazolo[5,4-d]pyrimidin-7-yl]-(4-trifluoromethyl-phenyl)-amine (25 mg, 0.05 mmol) and the resulting mixture was heated to 60° C. After 4 h, the resulting solution was acidified with 1 drop of acetic acid and purified directly by reverse phase HPLC to afford a colorless solid (10.3 mg, 45%). MS (ESI): mass calcd. for C$_{20}$H$_{13}$Cl$_2$F$_3$N$_4$OS, 484.0; m/z found, 485.0 [M+H]$^+$. $^1$H NMR (CDCl$_3$): 8.01 (s, 1H), 7.95 (d, J=8.5 Hz, 2H), 7.65 (d, J=8.6 Hz, 2H), 7.43 (d, J=8.1 Hz, 2H), 7.30-7.25 (m, 1H), 4.74 (s, 2H), 4.05 (s, 3H).

Example 102

[2-(2,6-Dichloro-benzyl)-5-isopropoxy-thiazolo[5,4-d]pyrimidin-7-yl]-(4-trifluoromethyl-phenyl)-amine

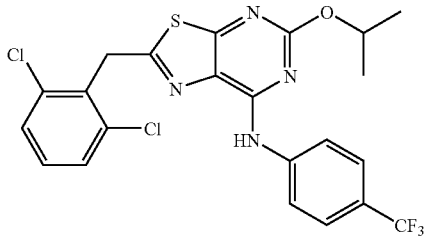

Sodium hydride (60% dispersion in mineral oil; 22.5 mg, 0.56 mmol) was added portionwise to IPA (3 mL) at rt. The resulting mixture was treated with [2-(2,6-dichloro-benzyl)-5-methanesulfonyl-thiazolo[5,4-d]pyrimidin-7-yl]-(4-rifluoromethyl-phenyl)-amine (50 mg, 0.09 mmol) and heated to 60° C. After 12 h, the resulting mixture was cooled to rt and purified by reverse phase HPLC to afford a colorless solid (40 mg, 83%). MS (ESI): mass calcd. for C$_{22}$H$_{17}$Cl$_2$F$_3$N$_4$OS, 512.0; m/z found, 513.0 [M+H]$^+$. $^1$H NMR ((CD$_3$)$_2$SO): 10.35 (s, 1H), 8.13 (d, J=8.6 Hz, 2H), 7.75-7.70 (m, 1H), 7.61

(d, J=8.0 Hz, 2H), 7.50-7.43 (m, 1H), 5.23-5.10 (m, 1H), 4.75 (s, 2H), 1.31 (d, J=6.2 Hz, 6H).

Example 103

[2-(2,6-Dichloro-benzyl)-5-isobutoxy-thiazolo[5,4-d]pyrimidin-7-yl]-(4-trifluoromethyl-phenyl)-amine

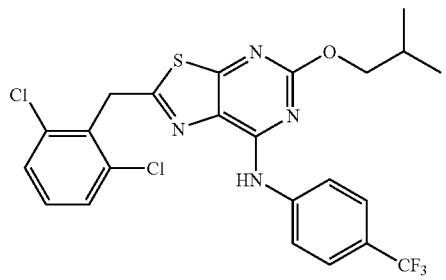

The title compound was prepared using methods analogous to those described for Example 102. MS (ESI): mass calcd. for $C_{23}H_{19}Cl_2F_3N_4OS$, 526.0; m/z found, 527.1 [M+H]$^+$. $^1$H NMR ((CD$_3$)$_2$SO): 10.44 (s, 1H), 8.15 (d, J=8.6 Hz, 2H), 7.72 (d, J=8.7 Hz, 2H), 7.62 (d, J=8.1 Hz, 2H), 7.50-7.44 (m, 1H), 4.75 (s, 2H), 4.07 (d, J=6.7 Hz, 2H), 2.13-1.96 (m, 1H), 0.96 (d, J=6.7 Hz, 6H).

Example 104

(4-Trifluoromethyl-phenyl)-[2-(2-triisopropylsilanyl-sulfanyl-benzyl)-thiazolo[5,4-d]pyrimidin-7-yl]-amine

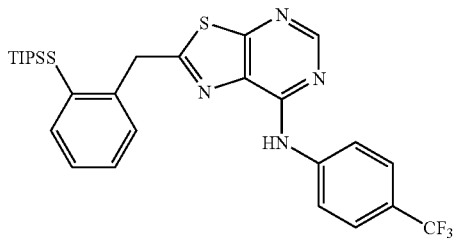

[2-(2-Iodo-benzyl)-thiazolo[5,4-d]pyrimidin-7-yl]-(4-trifluoromethyl-phenyl)-amine (0.26, 0.50 mmol), palladium acetate (5.7 mg, 0.03 mmol), PPh$_3$ (0.03 g, 0.10 mmol), and Cs$_2$CO$_3$ (0.21 g, 0.65 mmol) were combined in a sealed tube and placed under N$_2$ atmosphere. Toluene (5 mL) was added followed by triisopropylsilanethiol (0.11, 0.55 mmol) and the resulting suspension was heated to 100° C. for 8 h. The reaction mixture was cooled to rt and filtered through a pad of diatomaceous earth. The filtrate was concentrated and purified by FCC to provide the title compound as a colorless solid (0.15 g, 60%). MS (ESI): mass calcd. for $C_{28}H_{33}F_3N_4S_2Si$, 574.8; m/z found, 575.2 [M+H]$^+$. $^1$H NMR (CDCl$_3$): 8.65-8.60 (m, 1H), 8.14 (s, 1H), 7.99 (d, J=8.5 Hz, 2H), 7.65 (d, J=8.6 Hz, 2H), 7.57-7.53 (m, 1H), 7.35-7.32 (m, 1H), 7.25-7.18 (m, 2H), 4.79 (s, 2H)

Example 105

(2-Biphenyl-2-ylmethylthiazolo[5,4-d]pyrimidin-7-yl)-(4-trifluoromethylphenyl)-amine

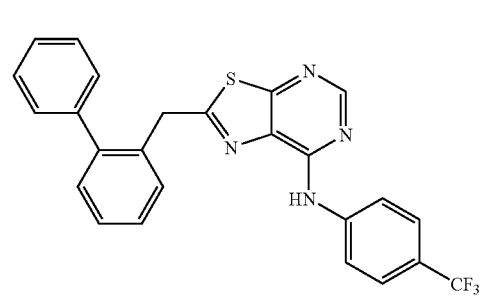

2-(2-Iodo-benzyl)-thiazolo[5,4-d]pyrimidinyl-7-yl]-(4-trifluoromethyl-phenyl)-amine (50 mg, 0.10 mmol), phenylboronic acid (13 mg, 0.11 mmol), tetrakis palladium triphenylphosphine (6 mg, 0.005 mmol), and K$_3$PO$_4$ (37 mg, 0.18 mmol) were combined in a sealed microwave tube and placed under N$_2$ atmosphere. Dimethoxyethane (0.8 mL) and H$_2$O (0.2 mL) were added and the reaction mixture was heated via microwave irradiation to 180° C. for 20 min. The reaction mixture was diluted with CH$_2$Cl$_2$ (5 mL) and filtered through a Na$_2$SO$_4$ plug. The filtrate was concentrated and purified by HPLC to afford a white solid (37 mg, 73%). MS (ESI): mass calcd. for $C_{25}H_{17}F_3N_4S$, 462.50; m/z found, 463.10 [M+H]$^+$. $^1$H NMR (CDCl$_3$): 8.61 (s, 1H), 7.99-7.93 (m, 3H), 7.65 (d, J=8.5 Hz, 1H), 7.45-7.27 (m, 9H), 4.41 (s, 2H).

The compounds in Examples 106-107 were prepared using methods analogous to those described for Example 105.

Example 106

2'-[7-(4-Trifluoromethylphenylamino)-thiazolo[5,4-d]pyrimidin-2-ylmethyl]-biphenyl-2-ol

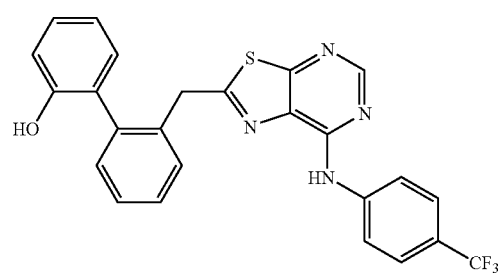

MS (ESI): mass calcd. for $C_{25}H_{17}F_3N_4OS$, 478.50; m/z found, 479.1 [M+H]$^+$. $^1$H NMR (CDCl$_3$): 8.61 (s, 1H), 8.50 (s, 1H), 8.03 (d, J=8.5 Hz, 2H), 7.66 (d, J=8.5 Hz, 2H), 7.48-7.42 (m, 2H), 7.40-7.31 (m, 2H), 7.31-7.26 (m, 1H), 7.14 (dd, J=7.5, 1.6 Hz, 1H), 7.03-6.95 (m, 2H), 4.44 (d, J=15.9 Hz, 1H), 4.35 (bs, 1H), 4.27 (d, J=15.9 Hz, 1H).

Example 107

2'-[7-(4-Trifluoromethylphenylamino)-thiazolo[5,4-d]pyrimidin-2-ylmethyl]-biphenyl-4-carboxylic acid amide

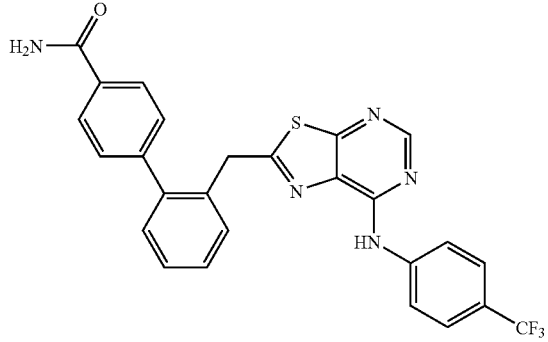

MS (ESI): mass calcd. for $C_{26}H_{18}F_3N_5OS$, 505.6; m/z found, 506.1 [M+H]$^+$. $^1$H NMR (CDCl$_3$): 8.62 (s, 1H), 8.05 (s, 1H), 7.95 (d, J=8.5 Hz, 2H), 7.88-7.82 (m, 2H), 7.65 (d, J=8.6 Hz, 2H), 7.49-7.37 (m, 5H), 7.35-7.29 (m, 1H), 6.67-6.14 (m, 2H), 4.39 (s, 2H).

Example 108

1-{2-[7-(4-Trifluoromethylphenylamino)-thiazolo[5,4-d]pyrimidin-2-ylmethyl]-phenyl}-ethanone

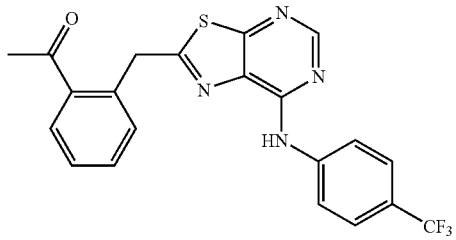

Step A: {2-[2-(1-Ethoxy-vinyl)-benzyl]-thiazolo[5,4-d]pyrimidin-7-yl}-(4-trifluoromethyl-phenyl)-amine 2-(2-Iodo-benzyl)-thiazolo[5,4-d]pyrimidinyl-7-yl]-(4-trifluoromethyl-phenyl)-amine (0.40 g, 0.78 mmol), tetrakis palladium triphenylphosphine (45 mg, 0.04 mmol), and LiCl (50 mg, 1.17 mmol) were combined in a sealed tube and placed under N$_2$ atmosphere. Tributyl(1-ethoxyvinyl)tin (0.42, 1.17 mmol) and DMF (5 mL) were added and the reaction mixture was heated to 120° C. for 8 h. The mixture was cooled to rt, diluted with H$_2$O (10 mL), and extracted with EtOAc (3×5 mL). The combined organic layers were dried (Na$_2$SO$_4$) and concentrated. The residue was purified by FCC to afford the title compound, which was carried into the next step. MS (ESI): mass calcd. for $C_{23}H_{19}F_3N_4OS$, 456.48; m/z found, 457.2 [M+H]$^+$.

Step B

{2-[2-(1-Ethoxy-vinyl)-benzyl]-thiazolo[5,4-d]pyrimidin-7-yl}-(4-trifluoromethyl-phenyl)-amine (230 mg, 0.62 mmol) was dissolved in THF (5 mL) and 2 N HCl (2 mL) and the reaction mixture was stirred at rt for 1.5 h. The reaction mixture was diluted with EtOAc (20 mL), washed with satd. aq. NaCl (2×5 mL), dried (Na$_2$SO$_4$), and concentrated to provide a white solid (0.23 g, 69%). MS (ESI): mass calcd. for $C_{21}H_{15}F_3N_4OS$, 428.4; m/z found, 429.1 [M+H]$^+$. $^1$H NMR (CDCl$_3$): 8.61 (s, 1H), 8.08 (s, 1H), 7.98 (d, J=8.5 Hz, 2H), 7.91 (dd, J=8.0, 1.2 Hz, 1H), 7.64 (d, J=8.6 Hz, 2H), 7.58-7.54 (m, 1H), 7.50-7.46 (m, 2H), 4.75 (s, 2H), 2.64 (s, 3H).

Example 109

[8-(2,6-Dichloro-benzyl)-9H-purin-6-yl]-(4-trifluoromethyl-phenyl)-amine trifluoroacetic acid salt

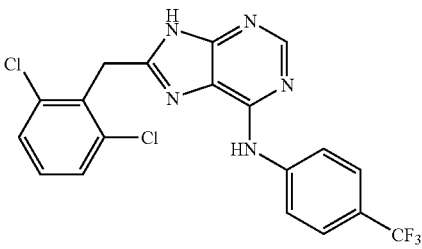

A solution of [8-(2,6-dichloro-benzyl)-9H-purin-6-yl]-(4-trifluoromethyl-phenyl)-amine (20 mg, 0.06 mmol), 4-trifluoromethylaniline (31.0 mg, 0.19 mmol) and tert-amyl alcohol (1 mL) was heated to 130° C. in a sealed tube. After 12 h, the mixture was cooled to rt and the resulting mixture was purified directly by preparative reverse-phase HPLC to a afford the title compound as a solid (13 mg, 45%). MS (ESI): mass calcd. for $C_{19}H_{12}Cl_2F_3N_5$, 437.0; m/z found, 438.1 [M+H]$^+$. $^1$H NMR ((CD$_3$)$_2$SO): 9.97 (s, 1H), 8.42 (s, 1H), 8.14 (d, J=8.6 Hz, 2H), 7.64 (d, J=8.71 Hz, 2H), 7.54 (d, J=8.0 Hz, 2H), 7.43-7.37 (m, 1H), 4.55 (s, 2H).

Example 110

(4-tert-Butyl-phenyl)-[8-(2,6-dichloro-benzyl)-9H-purin-6-yl]-amine trifluoroacetic acid salt

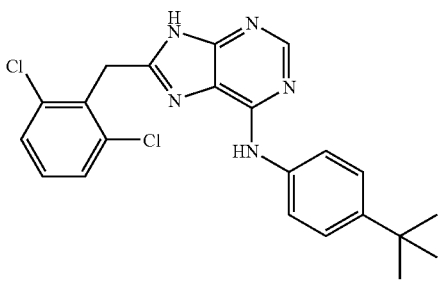

The title compound was prepared using a method analogous to that described for Example 109. MS (ESI): mass calcd. for $C_{22}H_{21}Cl_2N_5$, 425.1; m/z found, 426.2 [M+H]$^+$. $^1$H NMR ((CD)$_3$SO$_2$): 8.35 (s, 1H), 7.67 (d, J=8.6 Hz, 2H), 7.55 (d, J=8.0 Hz, 2H), 7.44-7.38 (m, 1H), 7.35 (d, J=8.61 Hz, 2H), 4.55 (s, 2H), 1.28 (s, 9H).

The compounds in Examples 111-128 may be prepared using methods analogous to those described for the preceding examples.

Example 111

[2-(2,6-Dimethyl-benzyl)-oxazolo[5,4-d]pyrimidin-7-yl]-(4-trifluoromethyl-phenyl)-amine

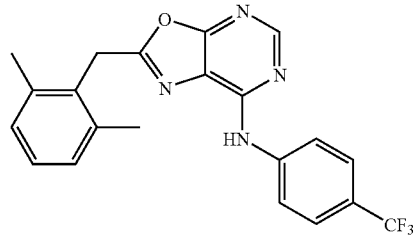

Example 112

[2-(2-Methyl-benzyl)-oxazolo[5,4-d]pyrimidin-7-yl]-(4-trifluoromethyl-phenyl)-amine

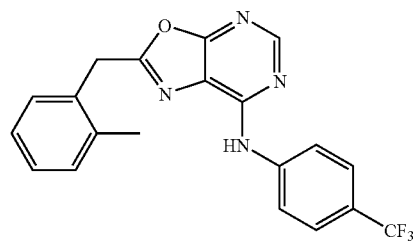

Example 113

[2-(2,6-Dichloro-benzyl)-5-methyl-oxazolo[5,4-d]pyrimidin-7-yl]-(4-trifluoromethyl-phenyl)-amine

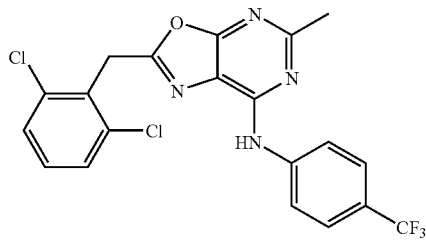

Example 114

[8-(2,6-Dimethyl-benzyl)-9H-purin-6-yl]-(4-trifluoromethyl-phenyl)-amine

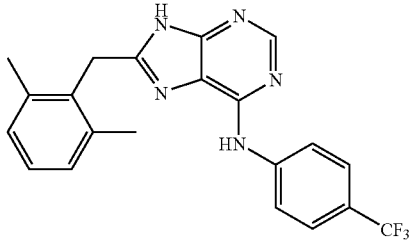

Example 115

[8-(2-Methyl-benzyl)-9H-purin-6-yl]-(4-trifluoromethyl-phenyl)-amine

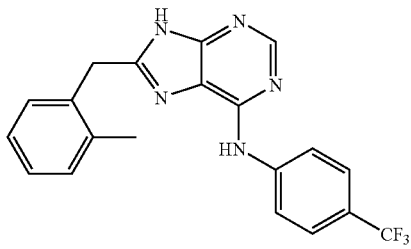

Example 116

[8-(2,6-Dimethyl-benzyl)-2-methyl-9H-purin-6-yl]-(4-trifluoromethyl-phenyl)-amine

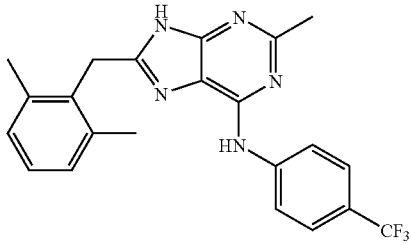

Example 117

[8-(2,6-Dichloro-benzyl)-2-methylsulfanyl-9H-Purin-6-yl]-(4-trifluoromethyl-phenyl)-amine

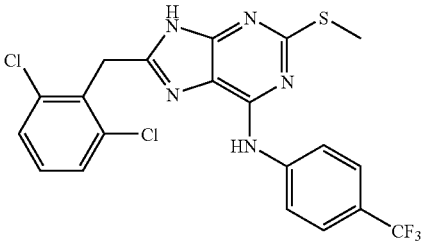

Example 118

[8-(2,6-Dichloro-benzyl)-2-methanesulfonyl-9H-Purin-6-yl]-(4-trifluoromethyl-phenyl)-amine

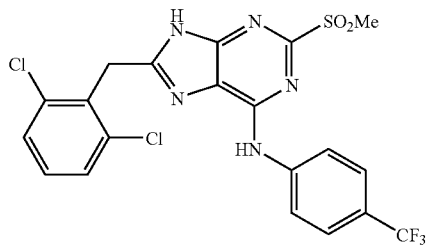

Example 119

[8-(2,6-Dichloro-benzyl)-2-methoxy-9H-purin-6-yl]-(4-trifluoromethyl-phenyl)-amine

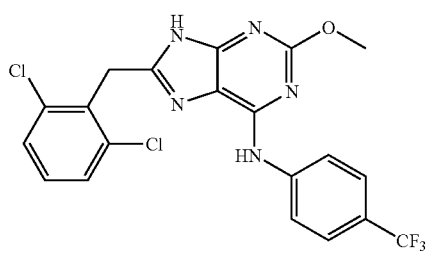

Example 120

[8-(2,6-Dichloro-benzyl)-2-(4-methyl-piperazin-1-yl)-9H-purin-6-yl]-(4-trifluoromethyl-phenyl)-amine

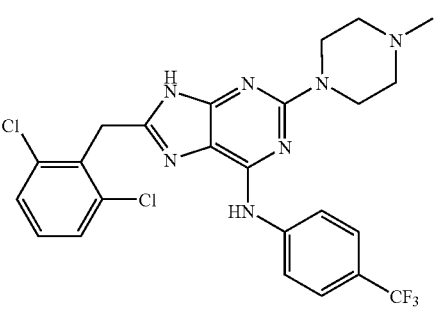

Example 121

[8-(2,6-Dichloro-benzyl)-2-(4-isobutyl-piperazin-1-yl)-9H-purin-6-yl]-(4-trifluoromethyl-phenyl)-amine

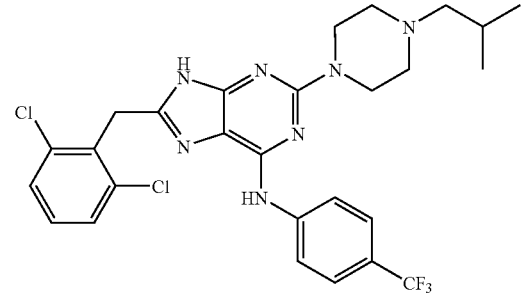

Example 122

[8-(2,6-Dichloro-benzyl)-2-morpholin-4-yl-9H-purin-6-yl]-(4-trifluoromethyl-phenyl)-amine

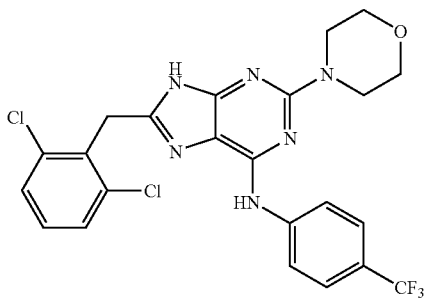

Example 123

[8-(2,6-Dichloro-benzyl)-2-piperidin-1-yl-9H-purin-6-yl]-(4-trifluoromethyl-phenyl)-amine

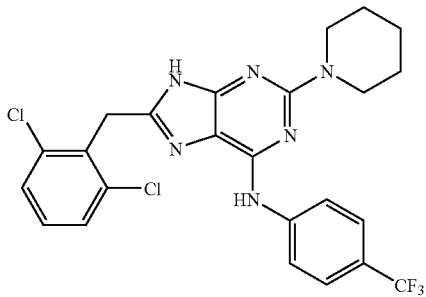

Example 124

8-(2,6-Dichloro-benzyl)-N²-isobutyl-N⁶-(4-trifluoromethyl-phenyl)-9H-purine-2,6-diamine

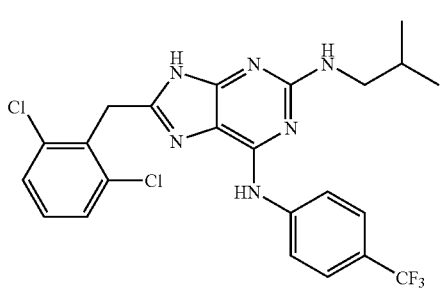

Example 125

8-(2,6-Dichloro-benzyl)-N²-isopropyl-N⁶-(4-trifluoromethyl-phenyl)-9H-purine-2,6-diamine

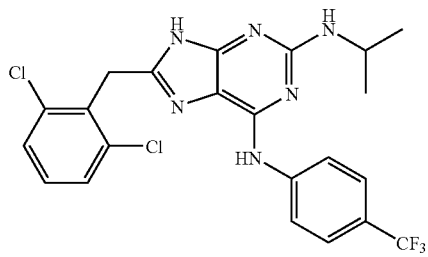

Example 126

[8-(2,6-Dichloro-benzyl)-2-pyrrolidin-1-yl-9H-purin-6-yl]-(4-trifluoromethyl-phenyl)-amine

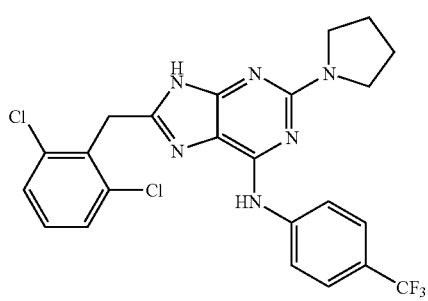

Example 127

{3,5-Dichloro-4-[7-(4-trifluoromethyl-phenylamino)-thiazolo[5,4-d]pyrimidin-2-ylmethyl]-phenyl}-methanol

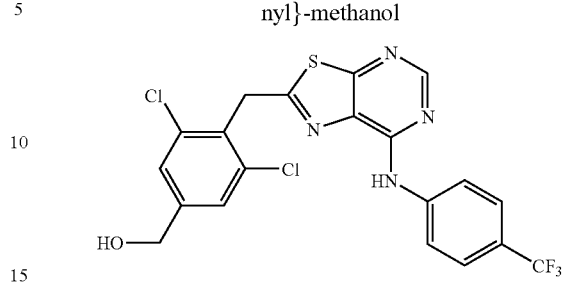

Example 128

{2-[2-(1-Dimethylamino-ethyl)-benzyl]-thiazolo[5,4-d]pyrimidin-7-yl}-(4-trifluoromethyl-phenyl)-amine

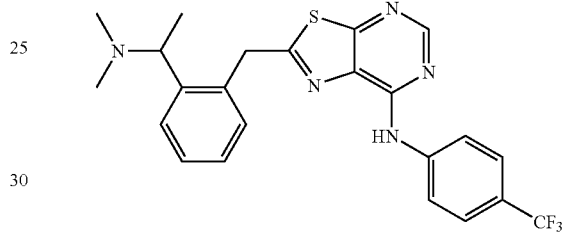

Example 129

{2-[2-(1-Morpholin-4-yl-ethyl)-benzyl]-thiazolo[5,4-d]pyrimidin-7-yl}-(4-trifluoromethyl-phenyl)-amine

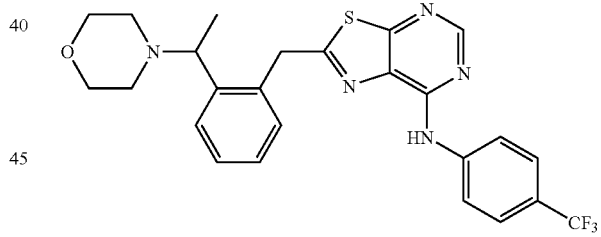

Biological Testing:
Functional Assay: Block of Capsaicin-Induced $Ca^{2+}$ Influx
A. Human Assay HEK293 cells were transfected with human TRPV1 cloned in pcDNA3.1zeo(+) using the Effectene non-liposomal lipid based transfection kit (Qiagen) (hTRPV1/HEK293). hTRPV1/HEK293 cells were routinely grown as monolayers under selection in zeocin (200 μg/mL; Invitrogen) in Dulbecco's Modified Eagle Medium (DMEM, Gibco BRL) supplemented with 10% fetal bovine serum, and penicillin/streptomycin (50 units/mL) in 5% $CO_2$ at 37° C. Cells were passaged frequently, every 3-5 days, to avoid overgrowth, depletion of essential medium components, or acidic medium exposure. Cells were passaged using a brief wash in 0.05% trypsin with 1 mM EDTA, followed by dissociation in divalent-free phosphate-buffered saline (Hyclone #SH30028.02). Dissociated cells were seeded onto poly-D-lysine coated black-walled 96-well plates (Biocoat; Becton Dickinson #354640) at about 40,000 cells per well and grown for approximately 1 day in culture medium to near confluency. The assay buffer was composed of 130 mM NaCl, 2 mM KCl, 2 mM $MgCl_2$, 10 mM HEPES, 5 mM glucose, and either 2 mM or 20 μM $CaCl_2$. On the day of the experiment, the culture medium was replaced with 2 mM calcium assay buffer using an automated plate washer (ELx405; Biotek, VT). The cells were incubated in 100 μL/well Fluo-3/AM (2 μM; TEFLabs #0116) with Pluronic F127 (100 μg/mL; Sigma #P2443) for 1 h at rt in the dark. After loading the cells, the dye solution was replaced with 50 μL/well of 20 μM calcium assay buffer using the ELx405 plate washer. Test compounds (50 μL/well) were added to the plate and incubated for 30 min. Intracellular $Ca^{2+}$ levels were subsequently assayed using a Fluorometric Imaging Plate Reader (FLIPR™ instrument, Molecular Devices, CA) to simultaneously monitor Fluo-3 fluorescence in all wells ($\lambda_{excitation}$=488 nm, $\lambda_{emission}$=540 nm) during challenge with agonist (capsaicin). The $IC_{50}$ values were determined. Cells were challenged with 150 nM capsaicin and the fluorescence counts were captured following agonist addition at a sampling rate of 0.33 Hz. The contents of the wells were mixed 3 times (40 μL mix volume) immediately after the additions were made. Concentration-dependence of block was determined by exposing each well of cells in duplicate rows of a 96-well plate to a serial dilution of test compound. The concentration series usually started at 10 μM with a three-fold serial decrement in concentration. The magnitude of the capsaicin response was determined by measuring the change in fluo3 fluorescence before and 100 seconds after the addition of the agonist. Data were analyzed using a non-linear regression program (Origin; OriginLab, MA).

B. Rat Assay

This assay was performed similarly to the human assay described above, but using HEK293 cells transfected with rat TRPV1 (rTRPV1/HEK293). These cells had a geneticin selection marker and were grown in Dulbecco's Modified Eagle Medium (DMEM, Gibco BRL) supplemented with 10% fetal bovine serum, penicillin/streptomycin (50 units/mL), and 500 μg/mL geneticin in 5% $CO_2$ at 37° C.

Results for the compounds tested in these assays are presented in Table 1. $IC_{50}$ values shown are the average (mean) of the results obtained. Where activity is shown as greater than (>) a particular value, the value is the solubility limit of the compound in the assay medium. Compounds were tested as in the free base, trifluoroacetic acid salt, or hydrochloride salt form.

TABLE 1

| Ex. | Human $IC_{50}$ (nM) | Rat $IC_{50}$ (nM) |
|---|---|---|
| 1 | 136 | 58 |
| 2 | 75 | 30 |
| 3 | 48 | 30 |
| 4 | 22 | 8 |
| 5 | NA | >6670 |
| 6 | 23 | 15 |
| 7 | NA | NA |
| 8 | 30 | 55 |
| 9 | 40 | 74 |
| 10 | NA | NA |
| 11 | NA | NA |
| 12 | 23 | 15 |
| 13 | 190 | 57 |
| 14 | 34 | 68 |
| 15 | 33 | 54 |
| 16 | 416 | 1090 |
| 17 | 147 | 146 |
| 18 | 85 | 154 |

TABLE 1-continued

| Ex. | Human $IC_{50}$ (nM) | Rat $IC_{50}$ (nM) |
|---|---|---|
| 19 | 471 | 247 |
| 20 | 40 | 32 |
| 21 | 79 | 54 |
| 22 | 280 | 33 |
| 23 | >6670 | 1790 |
| 24 | 840 | 196 |
| 25 | 54 | 11 |
| 26 | NA | 74 |
| 27 | NA | 43 |
| 28 | NA | >2220 |
| 29 | NA | 600 |
| 30 | NA | 4 |
| 31 | NA | 13 |
| 32 | 2923 | 55 |
| 33 | 813 | 111 |
| 34 | 3309 | 1458 |
| 35 | 988 | 42 |
| 36 | 2299 | 80 |
| 37 | 328 | 241 |
| 38 | NA | 99 |
| 39 | 225 | 189 |
| 40 | 49 | 51 |
| 41 | 32 | 29 |
| 42 | 99 | 56 |
| 43 | 269 | 167 |
| 44 | 193 | 44 |
| 45 | 274 | 183 |
| 46 | >6670 | 52 |
| 47 | 8900 | 4494 |
| 48 | 852 | 410 |
| 49 | 59 | 16 |
| 50 | 34 | 6 |
| 51 | 202 | 39 |
| 52 | 59 | 44 |
| 53 | 336 | 118 |
| 54 | 252 | 88 |
| 55 | 3440 | 2864 |
| 56 | 714 | 475 |
| 57 | 252 | 51 |
| 58 | 75 | 82 |
| 59 | 139 | 183 |
| 60 | 209 | 204 |
| 61 | 496 | 253 |
| 62 | 72 | 32 |
| 63 | >6670 | 3560 |
| 64 | 466 | 323 |
| 65 | 461 | 266 |
| 66 | 249 | 103 |
| 67 | NA | NA |
| 68 | 2320 | 1688 |
| 69 | 31 | 14 |
| 70 | NA | 1020 |
| 71 | NA | 2450 |
| 72 | NA | 72 |
| 73 | NA | 63 |
| 74 | NA | >6670 |
| 75 | NA | 132 |
| 76 | 310 | 74 |
| 77 | 1120 | 4338 |
| 78 | 316 | 215 |
| 79 | 104 | 32 |
| 80 | 4651 | 4036 |
| 81 | NA | 14 |
| 82 | NA | 959 |
| 83 | 136 | 12 |
| 84 | 263 | 38 |
| 85 | 433 | 112 |
| 86 | 1071 | 187 |
| 87 | 50 | 21 |
| 88 | 964 | 1043 |
| 89 | NA | NA |
| 90 | 6051 | 9710 |
| 91 | 4050 | 3160 |
| 92 | 4720 | 4335 |
| 93 | 276 | 231 |
| 94 | 924 | 246 |
| 95 | 292 | 119 |

TABLE 1-continued

| Ex. | Human IC$_{50}$ (nM) | Rat IC$_{50}$ (nM) |
|---|---|---|
| 96 | 466 | 224 |
| 97 | 1032 | 158 |
| 98 | NA | 1049 |
| 99 | NA | 195 |
| 100 | 126 | 62 |
| 101 | 207 | 34 |
| 102 | 188 | 74 |
| 103 | NA | 16 |
| 104 | 125 | 69 |
| 105 | 1640 | 1234 |
| 106 | 1007 | 343 |
| 107 | 6963 | 1533 |
| 108 | NA | NA |
| 109 | 716 | 116 |
| 110 | NA | NA |

NA = data not available

While the invention has been illustrated by reference to exemplary and preferred embodiments, it will be understood that the invention is intended not to be limited by the foregoing detailed description, but to be defined by the appended claims as properly construed under principles of patent law.

What is claimed is:

1. A compound selected from the group consisting of:
(a) compounds of Formula (I):

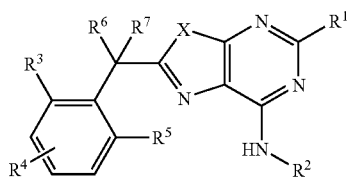

(I)

wherein:
$R^1$ is —H; —NR$^a$R$^b$; a —C$_{1-6}$alkyl, —OC$_{1-6}$alkyl, —S—C$_{1-6}$alkyl, or —SO$_2$—C$_{1-6}$alkyl group unsubstituted or substituted with an —OH, —OC$_{1-4}$alkyl, or —NR$^c$R$^d$ substituent;
where R$^a$ and R$^b$ are each independently —H; —C$_{1-6}$alkyl; a —C$_{2-4}$alkyl group substituted with a —OH, —OC$_{1-4}$alkyl, or —NR$^e$R$^f$ substituent; or a saturated monocyclic cycloalkyl, —C$_1$alkyl-(saturated monocyclic cycloalkyl), —C$_1$alkyl-(carbon-linked, saturated monocyclic heterocycloalkyl), benzyl, or —C$_1$alkyl-(monocyclic heteroaryl) group, each unsubstituted or substituted with a —C$_{1-6}$alkyl, —OH, —OC$_{1-4}$-alkyl, —NR$^p$R$^q$, or fluoro substituent;
or, R$^a$ and R$^b$ taken together with the nitrogen of attachment in —NR$^a$R$^b$ form a saturated monocyclic heterocycloalkyl group unsubstituted or substituted with one, two, or three moieties independently selected from the group consisting of —C$_{1-6}$alkyl, —C$_{1-2}$alkyl-OH, —C$_{1-2}$alkyl-OC$_{1-2}$alkyl, —OH, —OC$_{1-4}$alkyl, —NR$^p$R$^q$, fluoro, —CO$_2$H, oxo, dioxo and monocyclic cycloalkyl substituents;
where R$^c$ and R$^d$ are each independently —H or —C$_{1-6}$ alkyl;
or R$^c$ and R$^d$ taken together with the nitrogen of attachment in —NR$^c$R$^d$ form a saturated monocyclic heterocycloalkyl group unsubstituted or substituted with methyl;
R$^e$ and R$^f$ are each independently —H or —C$_{1-6}$alkyl;
or R$^e$ and R$^f$ taken together with their nitrogen of attachment in —NR$^e$R$^f$ form a saturated monocyclic heterocycloalkyl group unsubstituted or substituted with methyl; and
R$^p$ and R$^q$ are each independently —H or —C$_{1-6}$alkyl;
or R$^p$ and R$^q$ taken together with the nitrogen of attachment in —NR$^p$R$^q$ form a saturated monocyclic heterocycloalkyl group unsubstituted or substituted with methyl;

$R^2$ is:
1) a phenyl group unsubstituted or substituted with one, two, or three R$^g$ substituents;
where each R$^g$ substituent is —C$_{1-6}$alkyl, —OH, —OC$_{1-6}$alkyl, —CN, —NO$_2$, —N(R$^h$)R$^i$, —C(O)N(R$^h$)R$^i$, —C(O)C$_{1-6}$alkyl, —S(O)$_{0-2}$—C$_{1-6}$alkyl, —SO$_2$CF$_3$, —SO$_2$N(R$^h$)R$^i$, —SCF$_3$, halo, —CF$_3$, -OCF$_3$, —CO$_2$H, —CO$_2$C$_{1-6}$alkyl, —C(R$^j$)$_2$—CN, —C(R$^j$)$_2$—CO$_2$C$_{1-4}$alkyl, —C(R$^j$)$_2$—CO$_2$H, —C(R$^j$)$_2$—CON(R$^h$)R$^i$, —C(R$^j$)$_2$—CH$_2$N(R$^h$)R$^i$, or —C(R$^j$)$_2$—OH;
or two adjacent R$^g$ substituents taken together form —OC$_{1-2}$alkylO—, —C$_{2-6}$alkylO—, or —C$_{2-6}$alkylN(R$^h$)—;
where R$^h$ and R$^i$ are each independently —H or —C$_{1-6}$ alkyl;
or R$^h$ and R$^i$ taken together with their nitrogen of attachment in —NR$^h$R$^i$ form a saturated monocyclic heterocycloalkyl group unsubstituted or substituted with methyl;
where each R$^j$ is independently —H, —C$_{1-6}$alkyl, or —CF$_3$;
or both R$^j$ substituents taken together with the carbon to which they are attached form a monocyclic cycloalkyl ring; or
2) a thiadiazolyl or six-membered monocyclic heteroaryl ring, each substituted with —CF$_3$ or tert-butyl;

$R^3$ is —H, —CH$_3$, —CF$_3$, halo, —CN, —COC$_{1-6}$alkyl, —CO$_2$H, —CO$_2$C$_{1-6}$alkyl, —C(O)N(R$^k$)R$^l$, —CH$_2$N(R$^k$)R$^l$, —S(O)$_{0-2}$—C$_{1-6}$alkyl, —S—Si(C$_{1-6}$alkyl)$_3$, —SO$_2$CF$_3$, or —SO$_2$N(R$^k$)R$^l$; or a phenyl or 6-membered heteroaryl ring, each unsubstituted or substituted with —OH, —CH$_2$N(R$^k$)R$^l$, —C(O)N(R$^k$)R$^l$, —SO$_2$N(R$^k$)R$^l$, or —CO$_2$H;
where R$^k$ and R$^l$ are each independently —H or —C$_{1-6}$ alkyl; or R$^k$ and R$^l$ taken together with their nitrogen of attachment in —NR$^k$R$^l$ form a saturated monocyclic heterocycloalkyl group unsubstituted or substituted with methyl;

$R^4$ is —H, —CF$_3$, halo, —CN, —CO$_2$H, —CO$_2$C$_{1-6}$alkyl, —C(O)N(R$^n$)R$^o$, —C$_{1-4}$alkyl-OH, —C$_{1-4}$alkyl-N(R$^n$)R$^o$, —S(O)$_{0-2}$—C$_{1-6}$alkyl, —SO$_2$CF$_3$, or —SO$_2$N(R$^n$)R$^o$;
where R$^n$ and R$^o$ are each independently —H or —C$_{1-6}$ alkyl;

X is S;
$R^5$ is —H, —CH$_3$, halo, or —CF$_3$; and
$R^6$ and $R^7$ are each independently —H or methyl; or $R^6$ and $R^7$ taken together with the carbon to which they are attached form a monocyclic cycloalkyl ring;
and (b) pharmaceutically acceptable salts of the compounds of Formula (I).

2. A compound as defined in claim 1 selected from the group consisting of:
(a) the compounds of Formula (I) wherein $R^1$ is —H, methyl, —OC$_{1-4}$alkyl, —SC$_{1-4}$alkyl, or —SO$_2$—C$_{1-6}$ alkyl;
and (b) pharmaceutically acceptable salts of said compounds.

3. A compound as defined in claim 1 selected from the group consisting of:
(a) the compounds of Formula (I) wherein $R^1$ is —H;
and (b) pharmaceutically acceptable salts of said compounds.

4. A compound as defined in claim 1 selected from the group consisting of:
(a) the compounds of Formula (I) wherein $R^1$ is —$NR^aR^b$;
and (b) pharmaceutically acceptable salts of said compounds.

5. A compound as defined in claim 1 selected from the group consisting of:
(a) the compounds of Formula (I) wherein $R^1$ is isopropylamino, isobutylamino, diisopropylamino, 2-hydroxy-1-methyl-ethylamino, 2-morpholin-4-yl-ethyl, 2-pyrrolidin-1-yl-ethyl, cyclopropylmethylamino, azetidinyl, pyrrolidinyl, 2-methylpyrrolidinyl, 2-isopropyl-pyrrolidinyl, 2-methoxymethyl-pyrrolidinyl, 4-pyrrolidin-1-yl-piperidin-1-yl, piperazinyl, 4-methyl-piperazinyl, 4-isopropyl-piperazinyl, 4-isobutyl-piperazinyl, 4-cyclopentyl-piperazinyl, or morpholinyl;
and (b) pharmaceutically acceptable salts of said compounds.

6. A compound as defined in claim 1 selected from the group consisting of:
(a) the compounds of Formula (I) wherein $R^a$ and $R^b$ are each independently —H; methyl, ethyl, propyl, isopropyl, butyl, isobutyl, sec-butyl, tert-butyl, pentyl, isopentyl, or hexyl; an ethyl or propyl group substituted with an —OH or —$NR^eR^f$ substituent; or a cyclopropyl, cyclobutyl, cyclopentyl, cyclohexyl, cycloheptyl, cyclopropylmethyl, cyclopentylmethyl, pyridylmethyl, pyrrolidinylmethyl, or piperidinylmethyl group, each unsubstituted or substituted with a methyl, methoxy, or fluoro substituent;
and (b) pharmaceutically acceptable salts of said compounds.

7. A compound as defined in claim 1 selected from the group consisting of:
(a) the compounds of Formula (I) wherein $R^a$ and $R^b$ taken together with the nitrogen of attachment form an azetidinyl, pyrrolidinyl, piperidinyl, 2-oxo-piperidin-1-yl, piperazinyl, oxo-piperazinyl, morpholinyl, thiomorpholinyl, 1,1-dioxo-1-thiomorpholin-4-yl, or azepanyl group, each unsubstituted or substituted with a —$C_{1-4}$alkyl, —OH, —$CH_2$—$OC_{1-2}$alkyl, —$CO_2H$, or monocyclic cycloalkyl substituent;
and (b) pharmaceutically acceptable salts of said compounds.

8. A compound as defined in claim 1 selected from the group consisting of:
(a) the compounds of Formula (I) wherein $R^2$ is a phenyl group unsubstituted or substituted with one or two $R^g$ substituents;
and (b) pharmaceutically acceptable salts of said compounds.

9. A compound as defined in claim 1 selected from the group consisting of:
(a) the compounds of Formula (I) wherein $R^2$ is a thiadiazolyl, pyridinyl, or pyrazinyl ring substituted with —$CF_3$ or tert-butyl;
and (b) pharmaceutically acceptable salts of said compounds.

10. A compound as defined in claim 1 selected from the group consisting of:
(a) the compounds of Formula (I) wherein each $R^g$ substituent is independently methyl, isopropyl, tert-butyl, —$OCH_3$, —$SO_2CH_3$, —$SO_2CF_3$, —$SO_2NH_2$, —$SO_2$(morpholinyl), —$SO_2$(piperazinyl), fluoro, chloro, —$CF_3$, —$OCF_3$, —$CO_2CH_3$, —$C(CH_3)_2$—CN, —$C(CH_3)_2$—$CO_2CH_3$, —$C(CH_3)_2$—$CONH_2$, or —$C(CH_3)_2$—OH; or two adjacent $R^g$ substituents taken together form —$OC_{1-2}$alkylO—;
and (b) pharmaceutically acceptable salts of said compounds.

11. A compound as defined in claim 1 selected from the group consisting of:
(a) the compounds of Formula (I) wherein each $R^g$ substituent is independently tert-butyl or —$CF_3$;
and (b) pharmaceutically acceptable salts of said compounds.

12. A compound as defined in claim 1 selected from the group consisting of:
(a) the compounds of Formula (I) wherein $R^3$ is —H, chloro, iodo, methyl, —$CF_3$, —CN, or —S—Si(iPr)$_3$;
and (b) pharmaceutically acceptable salts of said compounds.

13. A compound as defined in claim 1 selected from the group consisting of:
(a) the compounds of Formula (I) wherein $R^3$ is —H, chloro, or —$CF_3$;
and (b) pharmaceutically acceptable salts of said compounds.

14. A compound as defined in claim 1 selected from the group consisting of:
(a) the compounds of Formula (I) wherein $R^4$ is —H, —CN, —$C(O)N(R'')R^o$, —$CH_2OH$, or —$CH_2N(R'')R^o$;
and (b) pharmaceutically acceptable salts of said compounds.

15. A compound as defined in claim 1 selected from the group consisting of:
(a) the compounds of Formula (I) wherein $R^4$ is —H or chloro;
and (b) pharmaceutically acceptable salts of said compounds.

16. A compound as defined in claim 1 selected from the group consisting of:
(a) the compounds of Formula (I) wherein X is S;
and (b) pharmaceutically acceptable salts of said compounds.

17. A compound as defined in claim 1 selected from the group consisting of:
(a) the compounds of Formula (I) wherein $R^5$ is —H, chloro, or —$CF_3$;
and (b) pharmaceutically acceptable salts of said compounds.

18. A compound as defined in claim 1, selected from the group consisting of:
[2-(2,6-Dichloro-benzyl)-thiazolo[5,4-d]pyrimidin-7-yl]-(4-trifluoromethyl-phenyl)-amine;
[2-(2-Iodo-benzyl)-thiazolo[5,4-d]pyrimidin-7-yl]-(4-trifluoromethyl-phenyl)-amine;
[2-(2,6-Dichloro-benzyl)-5-methylsulfanyl-thiazolo[5,4-d]pyrimidin-7-yl]-(4-trifluoromethyl-phenyl)-amine;
[2-(2,6-Dichloro-benzyl)-5-methyl-thiazolo[5,4-d]pyrimidin-7-yl]-(4-trifluoromethyl-phenyl)-amine;
[2-(2,6-Dichloro-benzyl)-5-methyl-thiazolo[5,4-d]pyrimidin-7-yl]-(6-trifluoromethyl-pyridin-3-yl)-amine;
[2-(2,6-Dichloro-benzyl)-thiazolo[5,4-d]pyrimidin-7-yl]-(6-trifluoromethyl-pyridin-3-yl)-amine;
(3-Chloro-4-trifluoromethyl-phenyl)-[2-(2,6-dichloro-benzyl)-thiazolo[5,4-d]pyrimidin-7-yl]-amine;
2-{4-[2-(2,6-Dichloro-benzyl)-5-methyl-thiazolo[5,4-d]pyrimidin-7-ylamino]-phenyl}-2-methyl-propionitrile;

[2-(2,6-Dichloro-benzyl)-5-methyl-thiazolo[5,4-d]pyrimidin-7-yl]-(3-fluoro-4-methanesulfonyl-phenyl)-amine;
[2-(2,6-Dichloro-benzyl)-5-methyl-thiazolo[5,4-d]pyrimidin-7-yl]-(4-trifluoromethyl-phenyl)-amine;
[2-(2,6-Dichloro-benzyl)-thiazolo[5,4-d]pyrimidin-7-yl]-(4-methanesulfonyl-phenyl)-amine;
[2-(2,6-Dichloro-benzyl)-thiazolo[5,4-d]pyrimidin-7-yl]-(4-trifluoromethanesulfonyl-phenyl)-amine;
[2-(2,6-Dichloro-benzyl)-thiazolo[5,4-d]pyrimidin-7-yl]-[4-(morpholine-4-sulfonyl)-phenyl]-amine;
[2-(2,6-Dichloro-benzyl)-thiazolo[5,4-d]pyrimidin-7-yl]-[4-(4-methyl-piperazine-1-sulfonyl)-phenyl]-amine;
2-(2-Methylbenzyl)-N-[4-(trifluoromethyl)phenyl][1,3]thiazolo[5,4-d]pyrimidin-7-amine;
2-(2-Methylbenzyl)-N-[6-(trifluoromethyl)pyridin-3-yl][1,3]thiazolo[5,4-d]pyrimidin-7-amine;
2-(2-Methylbenzyl)-N-[4-(methylsulfonyl)phenyl][1,3]thiazolo[5,4-d]pyrimidin-7-amine;
2-(2-Chlorobenzyl)-N-[4-(trifluoromethyl)phenyl][1,3]thiazolo[5,4-d]pyrimidin-7-amine;
2-(2-Chlorobenzyl)-N-[6-(trifluoromethyl)pyridin-3-yl][1,3]thiazolo[5,4-d]pyrimidin-7-amine;
2-(2-Chlorobenzyl)-N-[4-(methylsulfonyl)phenyl][1,3]thiazolo[5,4-d]pyrimidin-7-amine;
2-(2,6-Dichlorobenzyl)-N-[2-(trifluoromethyl)phenyl][1,3]thiazolo[5,4-d]pyrimidin-7-amine;
2-(2,6-Dichlorobenzyl)-N-[3-(trifluoromethyl)phenyl][1,3]thiazolo[5,4-d]pyrimidin-7-amine;
N-(4-tert-Butylphenyl)-2-(2,6-dichlorobenzyl)[1,3]thiazolo[5,4-d]pyrimidin-7-amine;
Methyl 2-(4-{[2-(2,6-dichlorobenzyl)[1,3]thiazolo[5,4-d]pyrimidin-7-yl]amino}phenyl)-2-methylpropanoate;
2-(2,4-Dichlorobenzyl)-N-[4-(trifluoromethyl)phenyl][1,3]thiazolo[5,4-d]pyrimidin-7-amine;
2-(2,6-Dichlorobenzyl)-N-[4-(piperazin-1-ylsulfonyl)phenyl][1,3]thiazolo[5,4-d]pyrimidin-7-amine;
2-(2,4-Dichlorobenzyl)-N-[6-(trifluoromethyl)pyridin-3-yl][1,3]thiazolo[5,4-d]pyrimidin-7-amine;
2-[2-(Trifluoromethyl)benzyl]-N-[4-(trifluoromethyl)phenyl][1,3]thiazolo[5,4-d]pyrimidin-7-amine;
2-[2-(Trifluoromethyl)benzyl]-N-[6-(trifluoromethyl)pyridin-3-yl][1,3]thiazolo[5,4-d]pyrimidin-7-amine;
2-Benzyl-N-[4-(trifluoromethyl)phenyl][1,3]thiazolo[5,4-d]pyrimidin-7-amine;
2-Benzyl-N-[6-(trifluoromethyl)pyridin-3-yl][1,3]thiazolo[5,4-d]pyrimidin-7-amine;
2-Benzyl-N-[4-(methylsulfonyl)phenyl][1,3]thiazolo[5,4-d]pyrimidin-7-amine;
2-(4-Chlorobenzyl)-N-[4-(trifluoromethyl)phenyl][1,3]thiazolo[5,4-d]pyrimidin-7-amine;
2-(4-Chlorobenzyl)-N-[6-(trifluoromethyl)pyridin-3-yl][1,3]thiazolo[5,4-d]pyrimidin-7-amine;
2-(2,6-Dichlorobenzyl)-N-(4-methoxyphenyl)[1,3]thiazolo[5,4-d]pyrimidin-7-amine;
2-(2,6-Dichlorobenzyl)-N-[6-(methylsulfanyl)pyridin-3-yl][1,3]thiazolo[5,4-d]pyrimidin-7-amine;
2-(2,6-Dichlorobenzyl)-N-(4-fluorophenyl)[1,3]thiazolo[5,4-d]pyrimidin-7-amine;
N-(4-Chlorophenyl)-2-(2,6-dichlorobenzyl)[1,3]thiazolo[5,4-d]pyrimidin-7-amine;
N-(4-Bromophenyl)-2-(2,6-dichlorobenzyl)[1,3]thiazolo[5,4-d]pyrimidin-7-amine;
2-(4-{[2-(2,6-Dichlorobenzyl)[1,3]thiazolo[5,4-d]pyrimidin-7-yl]amino}phenyl)-2-methylpropanenitrile;
2-(2,6-Dichlorobenzyl)-N-phenyl[1,3]thiazolo[5,4-d]pyrimidin-7-amine;
2-(2,6-Dichlorobenzyl)-N-[4-(trifluoromethoxy)phenyl][1,3]thiazolo[5,4-d]pyrimidin-7-amine;
2-(2,6-Dichlorobenzyl)-N-[3-fluoro-4-(methylsulfonyl)phenyl][1,3]thiazolo[5,4-d]pyrimidin-7-amine;
2-(2,6-Dichlorobenzyl)-N-(4-methylphenyl)[1,3]thiazolo[5,4-d]pyrimidin-7-amine;
2-(4-{[2-(2,6-Dichlorobenzyl)[1,3]thiazolo[5,4-d]pyrimidin-7-yl]amino}phenyl)-2-methylpropanamide;
N-Phenyl-2-[2-(trifluoromethyl)benzyl][1,3]thiazolo[5,4-d]pyrimidin-7-amine;
N-(4-Bromophenyl)-2-[2-(trifluoromethyl)benzyl][1,3]thiazolo[5,4-d]pyrimidin-7-amine;
N-(4-tert-Butylphenyl)-2-[2-(trifluoromethyl)benzyl][1,3]thiazolo[5,4-d]pyrimidin-7-amine;
N-[4-(Methylsulfonyl)phenyl]-2-[2-(trifluoromethyl)benzyl][1,3]thiazolo[5,4-d]pyrimidin-7-amine;
N-[4-(Morpholin-4-ylsulfonyl)phenyl]-2-[2-(trifluoromethyl)benzyl][1,3]thiazolo[5,4-d]pyrimidin-7-amine;
2-(3-Chlorobenzyl)-N-[6-(trifluoromethyl)pyridin-3-yl][1,3]thiazolo[5,4-d]pyrimidin-7-amine;
2-(3-Chlorobenzyl)-N-[4-(trifluoromethyl)phenyl][1,3]thiazolo[5,4-d]pyrimidin-7-amine;
2-(2,6-Dimethylbenzyl)-N-phenyl[1,3]thiazolo[5,4-d]pyrimidin-7-amine;
N-(4-Bromophenyl)-2-(2,6-dimethylbenzyl)[1,3]thiazolo[5,4-d]pyrimidin-7-amine;
N-(4-tert-Butylphenyl)-2-(2,6-dimethylbenzyl)[1,3]thiazolo[5,4-d]pyrimidin-7-amine;
2-(2,6-Dimethylbenzyl)-N-[4-(trifluoromethyl)phenyl][1,3]thiazolo[5,4-d]pyrimidin-7-amine;
2-(2,6-Dimethylbenzyl)-N-[6-(trifluoromethyl)pyridin-3-yl][1,3]thiazolo[5,4-d]pyrimidin-7-amine;
2-(2,6-Dimethylbenzyl)-N-[4-(morpholin-4-ylsulfonyl)phenyl][1,3]thiazolo[5,4-d]pyrimidin-7-amine;
2-(2,6-Dimethylbenzyl)-N-[4-(methylsulfonyl)phenyl][1,3]thiazolo[5,4-d]pyrimidin-7-amine;
[2-(2,6-Dichloro-benzyl)-5-methanesulfonyl-thiazolo[5,4-d]pyrimidin-7-yl]-(4-trifluoromethyl-phenyl)-amine;
[2-(2,6-Dichloro-benzyl)-5-morpholin-4-yl-thiazolo[5,4-d]pyrimidin-7-yl]-(4-trifluoromethyl-phenyl)-amine;
[2-(2,6-Dichloro-benzyl)-5-(2-methyl-pyrrolidin-1-yl)-thiazolo[5,4-d]pyrimidin-7-yl]-(4-trifluoromethyl-phenyl)-amine;
2-(2,6-Dichloro-benzyl)-$N^5$-(2-morpholin-4-yl-ethyl)-$N^7$-(4-trifluoromethyl-phenyl)-thiazolo[5,4-d]pyrimidine-5,7-diamine;
$N^5$-Cyclopropylmethyl-2-(2,6-dichloro-benzyl)-$N^7$-(4-trifluoromethyl-phenyl)-thiazolo[5,4-d]pyrimidine-5,7-diamine;
[2-(2,6-Dichloro-benzyl)-5-pyrrolidin-1-yl-thiazolo[5,4-d]pyrimidin-7-yl]-(4-trifluoromethyl-phenyl)-amine;
[2-(2,6-Dichloro-benzyl)-5-(2-isopropyl-pyrrolidin-1-yl)-thiazolo[5,4-d]pyrimidin-7-yl]-(4-trifluoromethyl-phenyl)-amine;
2-(2,6-Dichloro-benzyl)-$N^5$-isobutyl-$N^7$-(4-trifluoromethyl-phenyl)-thiazolo[5,4-d]pyrimidine-5,7-diamine;
2-[2-(2,6-Dichloro-benzyl)-7-(4-trifluoromethyl-phenylamino)-thiazolo[5,4-d]pyrimidin-5-ylamino]-propan-1-ol;
(S)-[2-(2,6-Dichloro-benzyl)-5-(2-rnethoxymethyl-pyrrolidin-1-yl)-thiazolo[5,4-d]pyrimidin-7-yl]-(4-trifluoromethyl-phenyl)-amine;
2-(2,6-Dichloro-benzyl)-$N^5$-isopropyl-$N^7$-(4-trifluoromethyl-phenyl)-thiazolo[5,4-d]pyrimidine-5,7-diamine;
[5-Azetidin-1-yl-2-(2,6-dichloro-benzyl)-thiazolo[5,4-d]pyrimidin-7-yl]-(4-trifluoromethyl-phenyl)-amine;

[2-(2,6-Dichloro-benzyl)-5-piperazin-1-yl-thiazolo[5,4-d]pyrimidin-7-yl]-(4-trifluoromethyl-phenyl)-amine;
[2-(2,6-Dichloro-benzyl)-5-(4-isopropyl-piperazin-1-yl)-thiazolo[5,4-d]pyrimidin-7-yl]-(4-trifluoromethyl-phenyl)-amine;
[5-(4-Cyclopentyl-piperazin-1-yl)-2-(2,6-dichloro-benzyl)-thiazolo[5,4-d]pyrimidin-7-yl]-(4-trifluoromethyl-phenyl)-amine;
[2-(2,6-Dichloro-benzyl)-5-(4-pyrrolidin-1-yl-pipendin-1-yl)-thiazolo[5,4-d]pyrimidin-7-yl]-(4-trifluoromethyl-phenyl)-amine;
$N^5$-Cyclopropyl-2-(2,6-dichloro-benzyl)-$N^7$-(4-trifluoromethyl-phenyl)-thiazolo[5,4-d]pyrimidine-5,7-diamine;
$N^5$-Cyclobutyl-2-(2,6-dichloro-benzyl)-$N^7$-(4-trifluoromethyl-phenyl)-thiazolo[5,4-d]pyrimidine-5,7-diamine;
2-(2,6-Dichloro-benzyl)-$N^5$,$N^5$-diisobutyl-$N^7$-(4-trifluoromethyl-phenyl)-thiazolo[5,4-d]pyrimidine-5,7-diamine;
[2-(2,6-Dichloro-benzyl)-5-pipendin-1-yl-thiazolo[5,4-d]pyrimidin-7-yl]-(4-trifluoromethyl-phenyl)-amine;
2-(2,6-Dichloro-benzyl)-$N^5$-(2-pyrrolidin-1-yl-ethyl)-$N^7$-(4-trifluoromethyl-phenyl)-thiazolo[5,4-d]pyrimidine-5,7-diamine;
[2-(2,6-Dichloro-benzyl)-5-(4-isobutyl-piperazin-1-yl)-thiazolo[5,4-d]pyrimidin-7-yl]-(4-trifluoromethyl-phenyl)-amine;
2-(2,6-Dichloro-benzyl)-$N^5$-pyridin-2-ylmethyl-$N^7$-(4-trifluoromethyl-phenyl)-thiazolo[5,4-d]pyrimidine-5,7-diamine;
2-(2,6-Dichloro-benzyl)-$N^5$-pyridin-3-ylmethyl-$N^7$-(4-trifluoromethyl-phenyl)-thiazolo[5,4-d]pyrimidine-5,7-diamine;
2-(2,6-Dichloro-benzyl)-$N^5$-pyridin-4-ylmethyl-$N^7$-(4-trifluoromethyl-phenyl)-thiazolo[5,4-d]pyrimidine-5,7-diamine;
2-(2,6-Dichlorobenzyl)-$N^5$-(1-pyridin-2-ylethyl)-$N^7$-(4-(trifluoromethyl)phenyl][1,3]thiazolo[5,4-d]pyrimidine-5,7-diamine;
2-(2,6-Dichlorobenzyl)-$N^5$-[(1-ethylpyrrolidin-2-yl)methyl]-$N^7$-[4-(trifluoromethyl)phenyl][1,3]thiazolo[5,4-d]pyrimidine-5,7-diamine;
2-(2,6-Dichlorobenzyl)-$N^5$-[(3R)-pyrrolidin-3-ylmethyl]-$N^7$-[4-(trifluoromethyl)phenyl][1,3]thiazolo[5,4-d]pyrimidine-5,7-diamine;
2-(2,6-Dichlorobenzyl)-$N^5$-(piperidin-2-ylmethyl)-$N^7$-[4-(trifluoromethyl)phenyl][1,3]thiazolo[5,4-d]pyrimidine-5,7-diamine;
2-(2,6-Dichlorobenzyl)-$N^5$-(piperidin-3-ylmethyl)-$N^7$-[4-(trifluoromethyl)phenyl][1,3]thiazolo[5,4-d]pyrimidine-5,7-diamine;
2-(2,6-Dichlorobenzyl)-$N^5$-(piperidin-4-ylmethyl)-$N^7$-[4-(trifluoromethyl)phenyl][1,3]thiazolo[5,4-d]pyrimidine-5,7-diamine;
[2-(2,6-Dichloro-benzyl)-thiazolo[5,4-d]pyrimidin-7-yl]-(5-trifluoromethyl-pyrazin-2-yl)-amine;
[2-(2,6-Dichloro-benzyl)-thiazolo[5,4-d]pyrimidin-7-yl]-(5-trifluoromethyl-pyridin-2-yl)-amine;
2-[2-(Trifluoromethyl)benzyl]-N-[5-(trifluoromethyl)pyridin-2-yl][1,3]thiazolo[5,4-d]pyrimidin-7-amine;
[2-(2-Chloro-benzyl)-thiazolo[5,4-d]pyrimidin-7-yl]-(5-trifluoromethyl-pyridin-2-yl)-amine;
[2-(2,6-Dichloro-benzyl)-5-methyl-thiazolo[5,4-d]pyrimidin-7-yl]-(5-trifluoromethyl-pyridin-2-yl)-amine;
2-(2,6-Dichlorobenzyl)-N-[5-(trifluoromethyl)-1,3,4-thiadiazol-2-yl][1,3]thiazolo[5,4-d]pyrimidin-7-amine;
N-(5-tert-Butyl-1,3,4-thiadiazol-2-yl)-2-(2,6-dichlorobenzyl)[1,3]thiazolo[5,4-d]pyrimidin-7-amine;
2-[7-(4-Trifluoromethyl-phenylamino)-thiazolo[5,4-d]pyrimidin-2-ylmethyl]-benzon itrile;
[2-(2,6-Dichloro-benzyl)-5-methoxy-thiazolo[5,4-d]pyrimidin-7-yl]-(4-trifluoromethyl-phenyl)-amine;
[2-(2,6-Dichloro-benzyl)-5-isopropoxy-thiazolo[5,4-d]pyrimidin-7-yl]-(4-trifluoromethyl-phenyl)-amine;
[2-(2,6-Dichloro-benzyl)-5-isobutoxy-thiazolo[5,4-d]pyrimidin-7-yl]-(4-trifluoromethyl-phenyl)-amine;
(4-Trifluoromethyl-phenyl)-[2-(2-triisopropylsilanylsulfanyl-benzyl)-thiazolo[5,4-d]pyrimidin-7-yl]-amine;
(2-Biphenyl-2-ylmethylthiazolo[5,4-d]pyrimidin-7-yl)-(4-trifluoromethylphenyl)-amine;
2'-[7-(4-Trifluoromethylphenylamino)-thiazolo[5,4-d]pyrimidin-2-ylmethyl]-biphenyl-2-ol;
2'-[7-(4-Trifluoromethylphenylamino)-thiazolo[5,4-d]pyrimidin-2-ylmethyl]-biphenyl-4-carboxylic acid amide;
1-{2-[7-(4-Trifluoromethylphenylamino)-thiazolo[5,4-d]pyrimidin-2-ylmethyl]-phenyl}-ethanone;
{3,5-Dichloro-4-[7-(4-trifluoromethyl-phenylamino)-thiazolo[5,4-d]pyrimidin-2-ylmethyl]-phenyl}-methanol;
{2-[2-(1-Dimethylamino-ethyl)-benzyl]-thiazolo[5,4-d]pyrimidin-7-yl}-(4-trifluoromethyl-phenyl)-amine; and
{2-[2-(1-Morpholin-4-yl-ethyl)-benzyl]-thiazolo[5,4-d]pyrimidin-7-yl}-(4-trifluoromethyl-phenyl)-amine;
and pharmaceutically acceptable salts thereof.

19. A pharmaceutical composition comprising:
(a) a therapeutically effective amount of at least one agent selected from compounds of Formula (I) and pharmaceutically acceptable salts of said compounds of Formula (I):

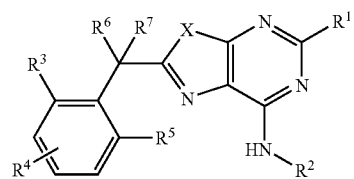

(I)

wherein:
$R^1$ is —H; —$NR^aR^b$; a —$C_{1-6}$alkyl, —$OC_{1-6}$alkyl, —S—$C_{1-6}$alkyl, or —$SO_2$—$C_{1-6}$alkyl group unsubstituted or substituted with an —OH, —$OC_{1-4}$alkyl, or —$NR^cR^d$ substituent;
where $R^a$ and $R^b$ are each independently —H; —$C_{1-6}$ alkyl; a —$C_{2-4}$alkyl group substituted with a —OH, —$OC_{1-4}$alkyl, or —$NR^eR^f$ substituent; or a saturated monocyclic cycloalkyl, —$C_1$alkyl-(saturated monocyclic cycloalkyl), —$C_1$alkyl-(carbon-linked, saturated monocyclic heterocycloalkyl), benzyl, or —$C_1$alkyl-(monocyclic heteroaryl) group, each unsubstituted or substituted with a —$C_{1-6}$alkyl, —OH, —$OC_{1-4}$-alkyl, —$NR^pR^q$, or fluoro substituent;
or, $R^a$ and $R^b$ taken together with the nitrogen of attachment in —$NR^aR^b$ form a saturated monocyclic heterocycloalkyl group unsubstituted or substituted with one, two, or three moieties independently selected from the group consisting of —$C_{1-6}$alkyl, —$C_{1-2}$alkyl-OH, —$C_{1-2}$alkyl-$OC_{1-2}$alkyl, —OH, —$OC_{1-4}$ alkyl, —$NR^pR^q$, fluoro, —$CO_2H$, oxo, dioxo and monocyclic cycloalkyl substituents;
where $R^c$ and $R^d$ are each independently —H or —$C_{1-6}$ alkyl;

or $R^c$ and $R^d$ taken together with the nitrogen of attachment in —$NR^cR^d$ form a saturated monocyclic heterocycloalkyl group unsubstituted or substituted with methyl;

$R^e$ and $R^f$ are each independently —H or —$C_{1-6}$alkyl;

or $R^e$ and $R^f$ taken together with their nitrogen of attachment in —$NR^eR^f$ form a saturated monocyclic heterocycloalkyl group unsubstituted or substituted with methyl; and $R^p$ and $R^q$ are each independently —H or —$C_{1-6}$alkyl;

or $R^p$ and $R^q$ taken together with the nitrogen of attachment in —$NR^pR^q$ form a saturated monocyclic heterocycloalkyl group unsubstituted or substituted with methyl;

$R^2$ is:
1) a phenyl group unsubstituted or substituted with one, two, or three $R^g$ substituents;
where each $R^g$ substituent is —$C_{1-6}$alkyl, —OH, —CN, —$NO_2$, —$N(R^h)R^i$, —$C(O)N(R^h)R^i$, —$C(O)C_{1-6}$alkyl, —$S(O)_{0-2}$—$C_{1-6}$alkyl, —$SO_2CF_3$, —$SO_2N(R^h)R^i$, —$SCF_3$, halo, —$CF_3$, —$CO_2H$, —$CO_2C_{1-6}$ alkyl, —$C(R^j)_2$—CN, —$C(R^j)_2$—$CO_2C_{1-4}$alkyl, —$C(R^j)_2$—$CO_2H$, —$C(R^j)_2$—$CON(R^h)R^i$, —$C(R^j)_2$—$CH_2N(R^h)R^i$, or —$C(R^j)_2$—OH;
or two adjacent $R^g$ substituents taken together form —$OC_{1-2}$alkylO—, —$C_{2-6}$alkylO—, or —$C_{2-6}$alkylN($R^h$)—;
where $R^h$ and $R^i$ are each independently —H or —$C_{1-6}$ alkyl;
or $R^h$ and $R^i$ taken together with their nitrogen of attachment in —$NR^hR^i$ form a saturated monocyclic heterocycloalkyl group unsubstituted or substituted with methyl;
where each $R^j$ is independently —H, —$C_{1-6}$alkyl, or —$CF_3$;
or both $R^j$ substituents taken together with the carbon to which they are attached form a monocyclic cycloalkyl ring; or
2) a thiadiazolyl or six-membered monocyclic heteroaryl ring, each substituted with —$CF_3$ or tert-butyl;

$R^3$ is —H, —$CH_3$, —$CF_3$, halo, —CN, —$CO_2H$, —$CO_2C_{1-6}$alkyl, —$C(O)N(R^k)R^l$, —$CH_2N(R^k)R^l$, —$S(O)_{0-2}$—$C_{1-6}$alkyl, —S—$Si(C_{1-6}$alkyl)$_3$, —$SO_2CF_3$, or —$SO_2N(R^k)R^l$; or a phenyl or 6-membered heteroaryl ring, each unsubstituted or substituted with —OH, —$CH_2N(R^k)R^l$, —$C(O)N(R^k)R^l$, —$SO_2N(R^k)R^l$, or —$CO_2H$;
where $R^k$ and $R^l$ are each independently —H or —$C_{1-6}$ alkyl; or $R^k$ and $R^l$ taken together with their nitrogen of attachment in —$NR^kR^l$ form a saturated monocyclic heterocycloalkyl group unsubstituted or substituted with methyl;

$R^4$ is —H, —$CF_3$, halo, —CN, —$CO_2H$, —$CO_2C_{1-6}$alkyl, —$C(O)N(R^n)R^o$, —$C_{1-4}$alkyl-OH, —$C_{1-4}$alkyl-N($R^n$)$R^o$, —$S(O)_{0-2}$—$C_{1-6}$alkyl, —$SO_2CF_3$, or —$SO_2N(R^n)R^o$;
where $R^n$ and $R^o$ are each independently —H or —$C_{1-6}$ alkyl;

X is S;

$R^5$ is —H, —$CH_3$, halo, or —$CF_3$; and $R^6$ and $R^7$ are each independently —H or methyl; or $R^6$ and $R^7$ taken together with the carbon to which they are attached form a monocyclic cycloalkyl ring;

and (b) a pharmaceutically acceptable excipient.

20. A pharmaceutical composition according to claim 19, wherein said agent is selected from the group consisting of:

[2-(2,6-Dichloro-benzyl)-thiazolo[5,4-d]pyrimidin-7-yl]-(4-trifluoromethyl-phenyl)-amine;

[2-(2-Iodo-benzyl)-thiazolo[5,4-d]pyrimidin-7-yl]-(4-trifluoromethyl-phenyl)-amine;

[2-(2,6-Dichloro-benzyl)-5-methylsulfanyl-thiazolo[5,4-d]pyrimidin-7-yl]-(4-trifluoromethyl-phenyl)-amine;

[2-(2,6-Dichloro-benzyl)-5-methyl-thiazolo[5,4-d]pyrimidin-7-yl]-(4-trifluoromethyl-phenyl)-amine;

[2-(2,6-Dichloro-benzyl)-5-methyl-thiazolo[5,4-d]pyrimidin-7-yl]-(6-trifluoromethyl-pyridin-3-yl)-amine;

[2-(2,6-Dichloro-benzyl)-thiazolo[5,4-d]pyrimidin-7-yl]-(6-trifluoromethyl-pyridin-3-yl)-amine;

(3-Chloro-4-trifluoromethyl-phenyl)-[2-(2,6-dichloro-benzyl)-thiazolo[5,4-d]pyrimidin-7-yl]-amine;

2-{4-[2-(2,6-Dichloro-benzyl)-5-methyl-thiazolo[5,4-d]pyrimidin-7-ylamino]-phenyl}-2-methyl-propionitrile;

[2-(2,6-Dichloro-benzyl)-5-methyl-thiazolo[5,4-d]pyrimidin-7-yl]-(3-fluoro-4-methanesulfonyl-phenyl)-amine;

[2-(2,6-Dichloro-benzyl)-5-methyl-thiazolo[5,4-d]pyrimidin-7-yl]-(4-trifluoromethyl-phenyl)-amine;

[2-(2,6-Dichloro-benzyl)-thiazolo[5,4-d]pyrimidin-7-yl]-(4-methanesulfonyl-phenyl)-amine;

[2-(2,6-Dichloro-benzyl)-thiazolo[5,4-d]pyrimidin-7-yl]-(4-trifluoromethanesulfonyl-phenyl)-amine;

[2-(2,6-Dichloro-benzyl)-thiazolo[5,4-d]pyrimidin-7-yl]-[4-(morpholine-4-sulfonyl)-phenyl]-amine;

[2-(2,6-Dichloro-benzyl)-thiazolo[5,4-d]pyrimidin-7-yl]-[4-(4-methyl-piperazine-1-sulfonyl)-phenyl]-amine;

2-(2-Methylbenzyl)-N-[4-(trifluoromethyl)phenyl][1,3]thiazolo[5,4-d]pyrimidin-7-amine;

2-(2-Methylbenzyl)-N-[6-(trifluoromethyl)pyridin-3-yl][1,3]thiazolo[5,4-d]pyrimidin-7-amine;

2-(2-Methylbenzyl)-N-[4-(methylsulfonyl)phenyl][1,3]thiazolo[5,4-d]pyrimidin-7-amine;

2-(2-Chlorobenzyl)-N-[4-(trifluoromethyl)phenyl][1,3]thiazolo[5,4-d]pyrimidin-7-amine;

2-(2-Chlorobenzyl)-N-[6-(trifluoromethyl)pyridin-3-yl][1,3]thiazolo[5,4-d]pyrimidin-7-amine;

2-(2-Chlorobenzyl)-N-[4-(methylsulfonyl)phenyl][1,3]thiazolo[5,4-d]pyrimidin-7-amine;

2-(2,6-Dichlorobenzyl)-N-[2-(trifluoromethyl)phenyl][1,3]thiazolo[5,4-d]pyrimidin-7-amine;

2-(2,6-Dichlorobenzyl)-N-[3-(trifluoromethyl)phenyl][1,3]thiazolo[5,4-d]pyrimidin-7-amine;

N-(4-tert-Butylphenyl)-2-(2,6-dichlorobenzyl)[1,3]thiazolo[5,4-d]pyrimidin-7-amine;

Methyl 2-(4-{[2-(2,6-dichlorobenzyl)[1,3]thiazolo[5,4-d]pyrimidin-7-yl]amino}phenyl)-2-methylpropanoate;

2-(2,4-Dichlorobenzyl)-N-[4-(trifluoromethyl)phenyl][1,3]thiazolo[5,4-d]pyrimidin-7-amine;

2-(2,6-Dichlorobenzyl)-N-[4-(piperazin-1-ylsulfonyl)phenyl][1,3]thiazolo[5,4-d]pyrimidin-7-amine;

2-(2,4-Dichlorobenzyl)-N-[6-(trifluoromethyl)pyridin-3-yl][1,3]thiazolo[5,4-d]pyrimidin-7-amine;

2-[2-(Trifluoromethyl)benzyl]-N-[4-(trifluoromethyl)phenyl][1,3]thiazolo[5,4-d]pyrimidin-7-amine;

2-[2-(Trifluoromethyl)benzyl]-N-[6-(trifluoromethyl)pyridin-3-yl][1,3]thiazolo[5,4-d]pyrimidin-7-amine;

2-Benzyl-N-[4-(trifluoromethyl)phenyl][1,3]thiazolo[5,4-d]pyrimidin-7-amine;

2-Benzyl-N-[6-(trifluoromethyl)pyridin-3-yl][1,3]thiazolo[5,4-d]pyrimidin-7-amine;

2-Benzyl-N-[4-(methylsulfonyl)phenyl][1,3]thiazolo[5,4-d]pyrimidin-7-amine;

2-(4-Chlorobenzyl)-N-[4-(trifluoromethyl)phenyl][1,3]thiazolo[5,4-d]pyrimidin-7-amine;

2-(4-Chlorobenzyl)-N-[6-(trifluoromethyl)pyridin-3-yl][1,3]thiazolo[5,4-d]pyrimidin-7-amine;

2-(2,6-Dichlorobenzyl)-N-(4-methoxyphenyl)[1,3]thiazolo[5,4-d]pyrimidin-7-amine;

2-(2,6-Dichlorobenzyl)-N-[6-(methylsulfanyl)pyridin-3-yl][1,3]thiazolo[5,4-d]pyrimidin-7-amine;

2-(2,6-Dichlorobenzyl)-N-(4-fluorophenyl)[1,3]thiazolo[5,4-d]pyrimidin-7-amine;

N-(4-Chlorophenyl)-2-(2,6-dichlorobenzyl)[1,3]thiazolo[5,4-d]pyrimidin-7-amine;

N-(4-Bromophenyl)-2-(2,6-dichlorobenzyl)[1,3]thiazolo[5,4-d]pyrimidin-7-amine;

2-(4-{[2-(2,6-Dichlorobenzyl)[1,3]thiazolo[5,4-d]pyrimidin-7-yl]amino}phenyl)-2-methylpropanenitrile;

2-(2,6-Dichlorobenzyl)-N-phenyl[1,3]thiazolo[5,4-d]pyrimidin-7-amine;

2-(2,6-Dichlorobenzyl)-N-[4-(trifluoromethoxy)phenyl][1,3]thiazolo[5,4-d]pyrimidin-7-amine;

2-(2,6-Dichlorobenzyl)-N-[3-fluoro-4-(methylsulfonyl)phenyl][1,3]thiazolo[5,4-d]pyrimidin-7-amine;

2-(2,6-Dichlorobenzyl)-N-(4-methylphenyl)[1,3]thiazolo[5,4-d]pyrimidin-7-amine;

2-(4-{[2-(2,6-Dichlorobenzyl)[1,3]thiazolo[5,4-d]pyrimidin-7-yl]amino}phenyl)-2-methylpropanamide;

N-Phenyl-2-[2-(trifluoromethyl)benzyl][1,3]thiazolo[5,4-d]pyrimidin-7-amine;

N-(4-Bromophenyl)-2-[2-(trifluoromethyl)benzyl][1,3]thiazolo[5,4-d]pyrimidin-7-amine;

N-(4-tert-Butylphenyl)-2-[2-(trifluoromethyl)benzyl][1,3]thiazolo[5,4-d]pyrimidin-7-amine;

N-[4-(Methylsulfonyl)phenyl]-2-[2-(trifluoromethyl)benzyl][1,3]thiazolo[5,4-d]pyrimidin-7-amine;

N-[4-(Morpholin-4-ylsulfonyl)phenyl]-2-[2-(trifluoromethyl)benzyl][1,3]thiazolo[5,4-d]pyrimidin-7-amine;

2-(3-Chlorobenzyl)-N-[6-(trifluoromethyl)pyridin-3-yl][1,3]thiazolo[5,4-d]pyrimidin-7-amine;

2-(3-Chlorobenzyl)-N-[4-(trifluoromethyl)phenyl][1,3]thiazolo[5,4-d]pyrimidin-7-amine;

2-(2,6-Dimethylbenzyl)-N-phenyl[1,3]thiazolo[5,4-d]pyrimidin-7-amine;

N-(4-Bromophenyl)-2-(2,6-dimethylbenzyl)[1,3]thiazolo[5,4-d]pyrimidin-7-amine;

N-(4-tert-Butylphenyl)-2-(2,6-dimethylbenzyl)[1,3]thiazolo[5,4-d]pyrimidin-7-amine;

2-(2,6-Dimethylbenzyl)-N-[4-(trifluoromethyl)phenyl][1,3]thiazolo[5,4-d]pyrimidin-7-amine;

2-(2,6-Dimethylbenzyl)-N-[6-(trifluoromethyl)pyridin-3-yl][1,3]thiazolo[5,4-d]pyrimidin-7-amine;

2-(2,6-Dimethylbenzyl)-N-[4-(morpholin-4-ylsulfonyl)phenyl][1,3]thiazolo[5,4-d]pyrimidin-7-amine;

2-(2,6-Dimethylbenzyl)-N-[4-(methylsulfonyl)phenyl][1,3]thiazolo[5,4-d]pyrimidin-7-amine;

[2-(2,6-Dichloro-benzyl)-5-methanesulfonyl-thiazolo[5,4-d]pyrimidin-7-yl]-(4-trifluoromethyl-phenyl)-amine;

[2-(2,6-Dichloro-benzyl)-5-morpholin-4-yl-thiazolo[5,4-d]pyrimidin-7-yl]-(4-trifluoromethyl-phenyl)-amine;

[2-(2,6-Dichloro-benzyl)-5-(2-methyl-pyrrolidin-1-yl)-thiazolo[5,4-d]pyrimidin-7-yl]-(4-trifluoromethyl-phenyl)-amine;

2-(2,6-Dichloro-benzyl)-$N^5$-(2-morpholin-4-yl-ethyl)-$N^7$-(4-trifluoromethyl-phenyl)-thiazolo[5,4-d]pyrimidine-5,7-diamine;

$N^5$-Cyclopropylmethyl-2-(2,6-dichloro-benzyl)-$N^7$-(4-trifluoromethyl-phenyl)-thiazolo[5,4-d]pyrimidine-5,7-diamine;

[2-(2,6-Dichloro-benzyl)-5-pyrrolidin-1-yl-thiazolo[5,4-d]pyrimidin-7-yl]-(4-trifluoromethyl-phenyl)-amine;

[2-(2,6-Dichloro-benzyl)-5-(2-isopropyl-pyrrolidin-1-yl)-thiazolo[5,4-d]pyrimidin-7-yl]-(4-trifluoromethyl-phenyl)-amine;

2-(2,6-Dichloro-benzyl)-$N^5$-isobutyl-$N^7$-(4-trifluoromethyl-phenyl)-thiazolo[5,4-d]pyrimidine-5,7-diamine;

2-[2-(2,6-Dichloro-benzyl)-7-(4-trifluoromethyl-phenylamino)-thiazolo[5,4-d]pyrimidin-5-ylamino]-propan-1-ol;

(S)-[2-(2,6-Dichloro-benzyl)-5-(2-methoxymethyl-pyrrolidin-1-yl)-thiazolo[5,4-d]pyrimidin-7-yl]-(4-trifluoromethyl-phenyl)-amine;

2-(2,6-Dichloro-benzyl)-$N^5$-isopropyl-$N^7$-(4-trifluoromethyl-phenyl)-thiazolo[5,4-d]pyrimidine-5,7-diamine;

[5-Azetidin-1-yl-2-(2,6-dichloro-benzyl)-thiazolo[5,4-d]pyrimidin-7-yl]-(4-trifluoromethyl-phenyl)-amine;

[2-(2,6-Dichloro-benzyl)-5-piperazin-1-yl-thiazolo[5,4-d]pyrimidin-7-yl]-(4-trifluoromethyl-phenyl)-amine;

[2-(2,6-Dichloro-benzyl)-5-(4-isopropyl-piperazin-1-yl)-thiazolo[5,4-d]pyrimidin-7-yl]-(4-trifluoromethyl-phenyl)-amine;

[5-(4-Cyclopentyl-piperazin-1-yl)-2-(2,6-dichloro-benzyl)-thiazolo[5,4-d]pyrimidin-7-yl]-(4-trifluoromethyl-phenyl)-amine;

[2-(2,6-Dichloro-benzyl)-5-(4-pyrrolidin-1-yl-pipendin-1-yl)-thiazolo[5,4-d]pyrimidin-7-yl]-(4-trifluoromethyl-phenyl)-amine;

$N^5$-Cyclopropyl-2-(2,6-dichloro-benzyl)-$N^7$-(4-trifluoromethyl-phenyl)-thiazolo[5,4-d]pyrimidine-5,7-diamine;

$N^5$-Cyclobutyl-2-(2,6-dichloro-benzyl)-$N^7$-(4-trifluoromethyl-phenyl)-thiazolo[5,4-d]pyrimidine-5,7-diamine;

2-(2,6-Dichloro-benzyl)-$N^5$,$N^5$-diisobutyl-$N^7$-(4-trifluoromethyl-phenyl)-thiazolo[5,4-d]pyrimidine-5,7-diamine;

[2-(2,6-Dichloro-benzyl)-5-pipendin-1-yl-thiazolo[5,4-d]pyrimidin-7-yl]-(4-trifluoromethyl-phenyl)-amine;

2-(2,6-Dichloro-benzyl)-$N^5$-(2-pyrrolidin-1-yl-ethyl)-$N^7$-(4-trifluoromethyl-phenyl)-thiazolo[5,4-d]pyrimidine-5,7-diamine;

[2-(2,6-Dichloro-benzyl)-5-(4-isobutyl-piperazin-1-yl)-thiazolo[5,4-d]pyrimidin-7-yl]-(4-trifluoromethyl-phenyl)-amine;

2-(2,6-Dichloro-benzyl)-$N^5$-pyridin-2-ylmethyl-$N^7$-(4-trifluoromethyl-phenyl)-thiazolo[5,4-d]pyrimidine-5,7-diamine;

2-(2,6-Dichloro-benzyl)-$N^5$-pyridin-3-ylmethyl-$N^7$-(4-trifluoromethyl-phenyl)-thiazolo[5,4-d]pyrimidine-5,7-diamine;

2-(2,6-Dichloro-benzyl)-$N^5$-pyridin-4-ylmethyl-$N^7$-(4-trifluoromethyl-phenyl)-thiazolo[5,4-d]pyrimidine-5,7-diamine;

2-(2,6-Dichlorobenzyl)-$N^5$-(1-pyridin-2-ylethyl)-$N^7$-[4-(trifluoromethyl)phenyl][1,3]thiazolo[5,4-d]pyrimidine-5,7-diamine;

2-(2,6-Dichlorobenzyl)-$N^5$-[(1-ethylpyrrolidin-2-yl)methyl]-$N^7$-(4-(trifluoromethyl)phenyl)[1,3]thiazolo[5,4-d]pyrimidine-5,7-diamine;

2-(2,6-Dichlorobenzyl)-$N^5$-[(3R)-pyrrolidin-3-ylmethyl]-$N^7$-[4-(trifluoromethyl)phenyl][1,3]thiazolo[5,4-d]pyrimidine-5,7-diamine;

2-(2,6-Dichlorobenzyl)-$N^5$-(piperidin-2-ylmethyl)-$N^7$-[4-(trifluoromethyl)phenyl][1,3]thiazolo[5,4-d]pyrimidine-5,7-diamine;

2-(2,6-Dichlorobenzyl)-$N^5$-(piperidin-3-ylmethyl)-$N^7$-[4-(trifluoromethyl)phenyl][1,3]thiazolo[5,4-d]pyrimidine-5,7-diamine;

2-(2,6-Dichlorobenzyl)-N$^5$-(piperidin-4-ylmethyl)-N$^7$-[4-(trifluoromethyl)phenyl][1,3]thiazolo[5,4-d]pyrimidine-5,7-diamine;

[2-(2,6-Dichloro-benzyl)-thiazolo[5,4-d]pyrimidin-7-yl]-(5-trifluoromethyl-pyrazin-2-yl)-amine;

[2-(2,6-Dichloro-benzyl)-thiazolo[5,4-d]pyrimidin-7-yl]-(5-trifluoromethyl-pyridin-2-yl)-amine;

2-[2-(Trifluoromethyl)benzyl]-N-[5-(trifluoromethyl)pyridin-2-yl][1,3]thiazolo[5,4-d]pyrimidin-7-amine;

[2-(2-Chloro-benzyl)-thiazolo[5,4-d]pyrimidin-7-yl]-(5-trifluoromethyl-pyridin-2-yl)-amine;

[2-(2,6-Dichloro-benzyl)-5-methyl-thiazolo[5,4-d]pyrimidin-7-yl]-(5-trifluoromethyl-pyridin-2-yl)-amine;

2-(2,6-Dichlorobenzyl)-N-[5-(trifluoromethyl)-1,3,4-thiadiazol-2-yl][1,3]thiazolo[5,4-d]pyrimidin-7-amine;

N-(5-tert-Butyl-1,3,4-thiadiazol-2-yl)-2-(2,6-dichlorobenzyl)[1,3]thiazolo[5,4-d]pyrimidin-7-amine;

2-[7-(4-Trifluoromethyl-phenylamino)-thiazolo[5,4-d]pyrimidin-2-ylmethyl]-benzonitrile;

[2-(2,6-Dichloro-benzyl)-5-methoxy-thiazolo[5,4-d]pyrimidin-7-yl]-(4-trifluoromethyl-phenyl)-amine;

[2-(2,6-Dichloro-benzyl)-5-isopropoxy-thiazolo[5,4-d]pyrimidin-7-yl]-(4-trifluoromethyl-phenyl)-amine;

[2-(2,6-Dichloro-benzyl)-5-isobutoxy-thiazolo[5,4-d]pyrimidin-7-yl]-(4-trifluoromethyl-phenyl)-amine;

(4-Trifluoromethyl-phenyl)-[2-(2-triisopropylsilanylsulfanyl-benzyl)-thiazolo[5,4-d]pyrimidin-7-yl]-amine;

(2-Biphenyl-2-ylmethylthiazolo[5,4-d]pyrimidin-7-yl)-(4-trifluoromethylphenyl)-amine;

2'-[7-(4-Trifluoromethylphenylamino)-thiazolo[5,4-d]pyrimidin-2-ylmethyl]-biphenyl-2-ol;

2'-[7-(4-Trifluoromethylphenylamino)-thiazolo[5,4-d]pyrimidin-2-ylmethyl]-biphenyl-4-carboxylic acid amide;

1-{2-[7-(4-Trifluoromethylphenylamino)-thiazolo[5,4-d]pyrimidin-2-ylmethyl]-phenyl}-ethanone;

{3,5-Dichloro-4-[7-(4-trifluoromethyl-phenylamino)-thiazolo[5,4-d]pyrimidin-2-ylmethyl]-phenyl}-methanol;

{2-[2-(1-Dimethylamino-ethyl)-benzyl]-thiazolo[5,4-d]pyrimidin-7-yl}-(4-trifluoromethyl-phenyl)-amine; and {2-[2-(1-Morpholin-4-yl-ethyl)-benzyl]-thiazolo[5,4-d]pyrimidin-7-yl}-(4-trifluoromethyl-phenyl)-amine;

and pharmaceutically acceptable salts thereof.

\* \* \* \* \*

UNITED STATES PATENT AND TRADEMARK OFFICE
CERTIFICATE OF CORRECTION

PATENT NO. : 8,288,397 B2
APPLICATION NO. : 12/316848
DATED : October 16, 2012
INVENTOR(S) : Branstetter et al.

Page 1 of 1

It is certified that error appears in the above-identified patent and that said Letters Patent is hereby corrected as shown below:

In the Claims

Claim 18, in column 97, line 9, 10, and 11 should read 2-(2,6-Dichloro-benzyl)-5-(4-pyrrolidin-1-yl-piperidin-1-yl)-thiazolo[5,4-d]pyrimidin-7-yl]-(4-trifluoromethyl-phenyl)-amine;

Claim 19, in column 99, line 18 should read where each $R^9$ substituent is $-C_{1-6}$alkyl, $-OH$, $-OC_{1-6}$alkyl, $-CN$, Claim 19, in column 99, line 21 should read $R^i$, $-SCF_3$, halo, $-CF_3$, $-OCF_3$, $-CO_2H$, $-CO_2C_{1-6}$alkyl, Claim 19, in column 99, line 42 should read $R^3$ is $-H$, $-CH_3$, $-CF_3$, halo, $-CN$, $-COC_{1-6}$alkyl, $-CO_2H$, Signed and Sealed this
Nineteenth Day of November, 2013

Teresa Stanek Rea
*Deputy Director of the United States Patent and Trademark Office*